United States Patent [19]

Takeuchi et al.

[11] Patent Number: 5,789,386
[45] Date of Patent: Aug. 4, 1998

[54] FLUORINE-CONTAINING ANTHRACYCLINE DERIVATIVES HAVING HYDROXYL GROUPS(S) MONO- OR DI-O-AMINOALKANOYLATED IN THE SUGAR MOIETY THEREOF

[75] Inventors: Tomio Takeuchi; Sumio Umezawa, both of Tokyo; Tsutomu Tsuchiya, Yokohama; Yasushi Takagi, Yokohama; Hiromi Sohtome, Kawasaki, all of Japan

[73] Assignee: Zaidan Hojin Biseibutsu Kagaku Kenkyu Kai, Tokyo, Japan

[21] Appl. No.: 709,297

[22] Filed: Sep. 9, 1996

[30] Foreign Application Priority Data

Sep. 8, 1995 [JP] Japan .................. 7-257152

[51] Int. Cl.$^6$ .................. A61K 31/70; C07H 15/24
[52] U.S. Cl. .................. 514/34; 536/6.4
[58] Field of Search .................. 536/6.4; 514/34

[56] References Cited

U.S. PATENT DOCUMENTS 5,220,001  6/1993  Ok et al. .................. 536/6.4

*Primary Examiner*—Elli Peselev
*Attorney, Agent, or Firm*—Larson & Taylor

[57] ABSTRACT

To provide novel fluorine-containing anthracycline derivatives having high antitumor activities and a solubility in water, there have now been synthesized a 7-O-(2,6-dideoxy-2-fluoro-3-O- or -4-O- or -3,4-di-O-aminoalkanoyl-α-L-talopyranosyl)daunomycinone or -adriamycinone of general formula (I) shown below, as well as a 7-O-(3-O- or -4-O- or -3,4-di-O-aminoalkanoyl-2,6-dideoxy-2,6,6,6-tetrafluoro-α-L-talopyranosyl- or -2,6-dideoxy-6,6,6-trifluoro-α-L-lyxo-hexopyranosyl) adriamycinone of general formula (II) shown below:

General formula (I)

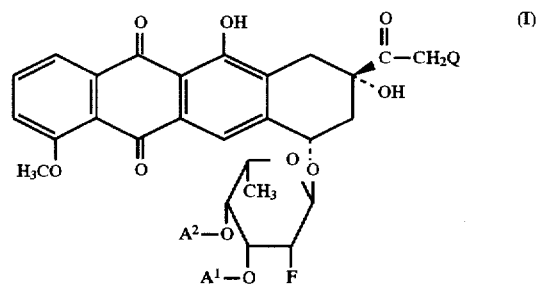

General formula (II)

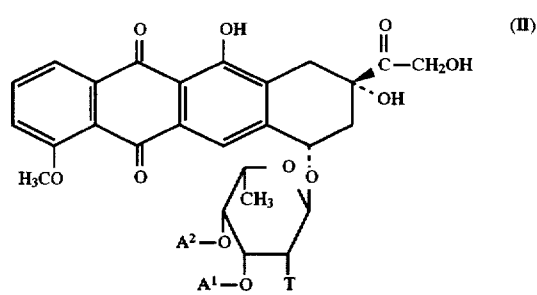

wherein either one or both of $A^1$ and $A^2$ is or are an α-amino acid residue or an ω-amino acid residue and T denotes a fluorine or hydrogen atom. The novel fluorine-containing anthracycline derivatives of general formulae (I) and (II) are highly active against tumors and soluble in water, and they are useful as antitumor agents administrable in the form of injectable solution.

20 Claims, No Drawings

FLUORINE-CONTAINING ANTHRACYCLINE DERIVATIVES HAVING HYDROXYL GROUPS(S) MONO- OR DI-O-AMINOALKANOYLATED IN THE SUGAR MOIETY THEREOF

FIELD OF THE INVENTION

This invention relates to new fluorine-containing anthracycline derivatives which exhibit antitumor activities but are of low toxicities and in which the 3'-hydroxyl group and/or the 4'-hydroxyl group of the sugar moiety of anthracycline has or have been mono- or di-O-aminoalkanoylated. More particularly, this invention relates to such new fluorine-containing anthracycline derivatives which are produced by esterifying with an amino acid the 3'-hydroxyl group and/or the 4'-hydroxyl group of 7-O-(2,6-dideoxy-2-fluoro-α-L-talopyranosyl)daunomycinone or -adriamycinone, or 7-O-(2,6-dideoxy-2,6,6,6-tetrafluoro-α-L-talopyranosyl) adriamycinone or 7-O-(2,6-dideoxy-6,6,6-trifluoro-α-L-lyxo-hexopyranosyl)adriamycinone, as the new anthracycline derivatives which have antitumor activities and are less toxic but are soluble in water.

BACKGROUND OF THE INVENTION

As the antibiotics of the anthracycline type are known daunomycin (named also as daunorubicin) and adriamycin (named also as doxorubicin). Daunomycin and adriamycin have broad anticancer spectra against experimental tumors and have found wide-spread clinical utilities as chemotherapeutic anticancer or antitumor agents.

While, daunomycin and adriamycin can exhibit somewhat strong anticancer or antitumor activities against various kinds of cancers or tumors but are not necessarily satisfactory as the anticancer agent or antitumor agent. Namely, daunomycin and adriamycin have been used widely as the chemotherapeutic antitumor agents for clinical treatments of tumor-bearing patients, but they are also known to bring about serious side-effects such as leukocytopenia, alopecia, myocardiopathy and others, in many instances.

Hitherto, therefore, some researches have been proceeded with in an attempt to synthesize newly such daunomycin derivative or adriamycin derivative which have higher antitumor activities but are of lower toxicities than daunomycin or adriamycin. For instance, the present inventors succeeded in synthesizing such anthracycline derivatives having anticancer or antitumor activities and represented by the following general formula (A):

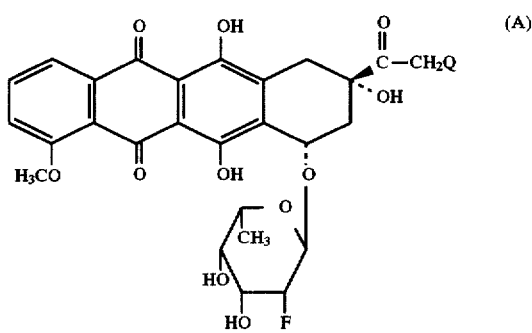

wherein Q means a hydrogen atom or a hydroxyl group, for example, 7-O-(2,6-dideoxy-2-fluoro-α-L-talopyranosyl) daunomycinone and 7-O-(2,6-dideoxy-2-fluoro-α-L-talopyranosyl)adriamycinone (Japanese Patent No. 1905434; Japanese Patent Publication "Kokoku" No. Hei-6-31298 and European Patent No. 0230013).

The present inventors also succeeded in synthesizing such antitumor anthracycline derivatives represented by the general formula (B):

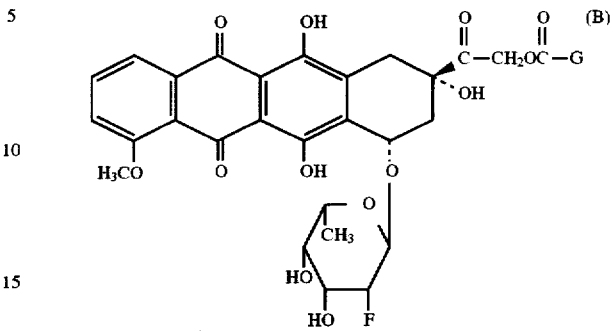

wherein G means a group —(CH$_2$)$_m$H, where m is an integer of 1–6, or a group —(CH$_2$)$_n$—COOH, where n is zero or an integer of 1–10 (Japanese Patent Publication "Kokoku" No. Hei-6-42304 and European Patent No. 0275431).

The present inventors further had conducted different investigations in an attempt to synthesize newly such novel anthracycline derivatives which exhibit higher anticancer or antitumor activities and lower toxicities than those of daunomycin, adriamycin and the anthracycline derivatives of the above-mentioned formulae (A) and (B).

The anticancer or antitumor activities of the anthracycline derivatives of the general formulae (A) and (B) above are remarkedly superior to those of daunomycin and adriamycin but are not yet satisfactory to a full extent. Accordingly, it is now still desirable to obtain such new anthracycline derivatives which can have much more enhanced anticancer or antitumor activities.

DETAILED DESCRIPTION OF THE INVENTION

In order to meet the demands as stated above, the present inventors have continued some researches with an object to synthesize a class of new anthracycline derivative containing a trifluoromethylated sugar as a moiety of the molecule.

As a result of the researches, the present inventors have now succeeded in synthesizing, as new sugar compounds, 1-O-acetyl derivative of 2,6-dideoxy-2,6,6,6-tetrafluoro-α-L-talopyranose as well as a 2,6-dideoxy-2,6,6,6-tetrafluoro-α-L-talopyranosyl halide and its 3,4-di-O-protected derivatives through a multi-stages method which starts from methyl α-D-lyxopyranoside.

Further, the present inventors have now succeeded in synthesizing, as the new anthracycline derivatives containing the trifluoromethylated sugar, such novel daunomycinone or adriamycinone derivatives having a general formula (C):

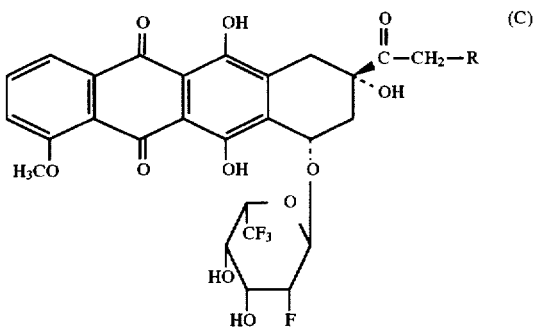

wherein R is a hydrogen atom or a hydroxyl group, by means of a process which comprises utilizing the newly synthesized derivatives of 2,6-dideoxy-2,6,6,6-tetrafluoro-α-L-talopyranose and condensing a 2,6-dideoxy-2,6,6,6-tetrafluoro-α-L-talopyranosyl group with the hydroxyl group at the 7-position of daunomycinone or adriamycinone. The present inventors also have found that even when an anthracycline derivative having the general formula (C) is administered at low dosages into test animals, the anthracycline derivative so administered can display a high anticancer or anitumor activity (see the specifications of Japanese patent applications No. 67714/94 and PCT application No. PCT/JP95/00407 published under PCT international publication No. WO95/24412 dated Sep. 14, 1995).

Examples of the daunomycinone or adriamycinone derivative of the general formula (C) above include the under-mentioned compouns (C-a) and (C-b).

(1) Compound (C-a): 7-O-(2,6-dideoxy-2,6,6,6-tetrafluoro-α-L-talopyranosyl)daunomycinone represented by the formula

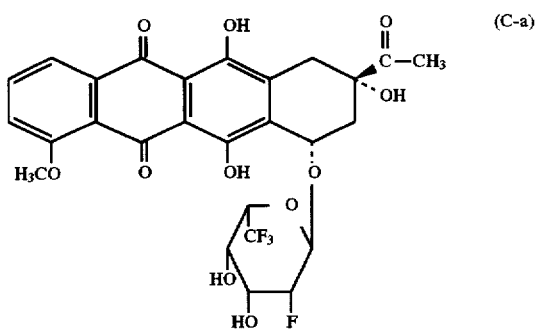

(2) Compound (C-b): 7-O-(2,6-dideoxy-2,6,6,6-tetrafluoro-α-L-talopyranosyl)adriamycinone represented by the formula

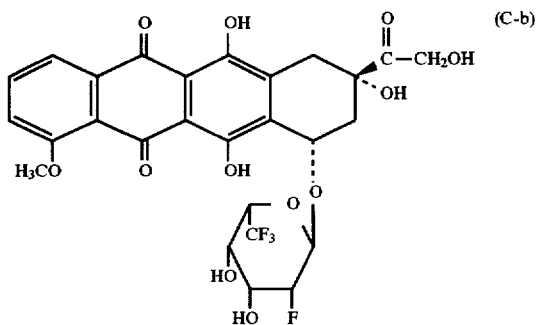

On the other hand, the present inventors have now further attempted to synthesize such new anthracycline derivatives which are analogous in the chemical structure to the anthracycline derivative of the general formula (C) shown hereinbefore but in which the fluoro group at the 2'-position of the adriamycinone derivative of the above formula (C-b) is replaced by a hydrogen atom. The present inventors have thus continued researches for this attempt. As a result of these further researches, the present inventors have now succeeded in synthesizing, as new sugar compounds, 1-O-acetyl derivative of 2,6-dideoxy-6,6,6-trifluoro-α-L-lyxo-hexopyranose as well as 2,6-dioxy- 6,6,6-trifluoro-α-L-lyxo-hexopyranosyl bromide and 3,4-di-O-protected derivatives thereof through a multi-staged method which starts from a known compound, methyl 4-deoxy-β-L-erythro-pentopyranoside.

And, the present inventors have now succeeded in synthesizing, as another anthracycline derivatives containing a trifluoromethylated sugar, 7-O-(2,6-dideoxy-6,6,6-trifluoro-α-L-lyxo-hexopyranosyl)adriamycinone which is an adiamycinone derivative represented by the following formula (D):

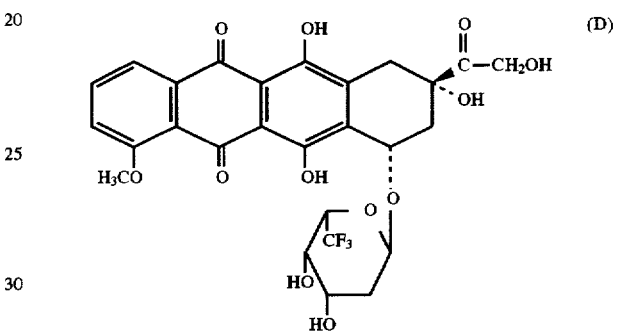

by means of a process which comprises utilizing the above-mentioned derivatives of 2,6-dideoxy-6,6,6-trifluoro-α-L-lyxo-hexopyranose and condensing a 2,6-dideoxy-6,6,6-trifluoro-α-L-lyxo-hexopyranosyl group with the hydroxyl group at the 7-position of adriamycinone. The present inventors also have found that even when an anthracycline derivative having the formula (D) is administered at low dosages to test animals, the anthracycline derivative so administered can display a high anticancer or antitumor activity, and that development of acute toxicity does not take place in the test animals having received the administration of the anthracycline derivative of the formula (D) at the low dosages which can give high anticancer or antitumor effects in the test animals by the administration of said anthracycline derivative (see the specification of the aforesaid. PCT application No. PCT/JP95/00407).

All the anthracycline derivatives of the formulae (A), (B), (C) and (D) above can exhibit high antitumor activities, but all of them, except the compound of the formula (B), are very much hardly soluble in water, so that there occurs a problem that these anthracycline derivatives are difficult to be formulated into an injectable preparation of aqueous solution-type, when these anthracycline derivatives are to be administered as an injectable preparation. While, the present inventors had already succeeded in providing some water-soluble derivatives of an adriamycin-type compound such as the compounds of the above formula (B), by hemiesterification of the 14-position of the adriamycin-type compound with a dicarboxylic acid. Still, however, there remain outstanding demands to produce newly such novel derivatives having a satisfactorily high solubility in water, from the anthracyclines of the formula (A), formula (C) or formula (D). In an attempt to synthesize such novel water-soluble anthracycline derivatives which can meet the above-mentioned demands, the present inventors have now continued extensive investigations. As a result of these investigations, the present inventors have now found that novel water-soluble derivatives can be produced from the fluorine-containing anthracycline derivatives of the formula (A), formula (C) or formula (D), when the present inventors employ another way of approach that an amino acid is introduced by an ester-linkage into either one or both of the 3-hydroxyl group and the 4-hydroxyl group of the sugar moiety of said fluorine-containing anthracycline derivatives, followed by making such salt-forming reaction that the amino group(s) present in the side-chain of the amino acid so introduced is or are converted into a salt with an inorganic acid or organic acid, and further that all of the above-mentioned water-soluble derivatives of the fluorine-containing anthracyclines so produced are able to maintain high antitumor or anticancer activititeies.

In a first aspect of this invention, there is thus provided a 7-O-(2,6-dideoxy-2-fluoro-3-O- or -4-O- or -3,4-di-O-aminoalkanoyl-α-L-talopyranosyl)anthracycline derivative represented by the general formula

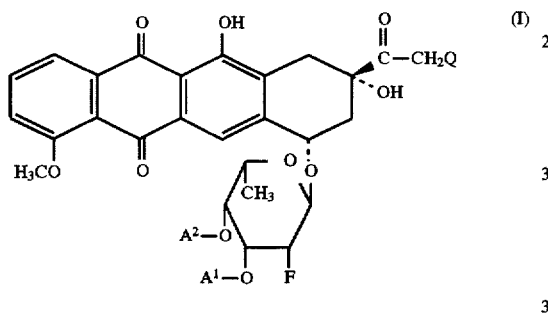

wherein Q is a hydrogen atom or a hydroxyl group, and either one or both of $A^1$ and $A^2$ is or are (i) glycyl group or a substituted glycyl group having the following formula (a):

where R is a hydrogen atom or an alkyl group of 1–8 carbon atoms, or an aryl group, particularly, phenyl group or a substituted phenyl group, or an aralkyl group, particularly a phenyl-($C_1$–$C_6$) alkyl group, or (ii) an ω-amino acid residue having the following formula (b):

where B is a linear alkylene group of 2–6 carbon atoms which may optionally be substituted by a ($C_1$–$C_6$) alkyl group, or a pharmaceutically acceptable acid addition salt thereof.

The anthracycliene derivative of the general formula (I) according to the first aspect of this invention embraces new compounds of six classes (i) to (vi) as described below.

(i) Compound which is 7-O-(2,6-dideoxy-2-fluoro-3-O-aminoalkanoyl-α-L-talopyanosyl)daunomycinone derivative represented by the general formula

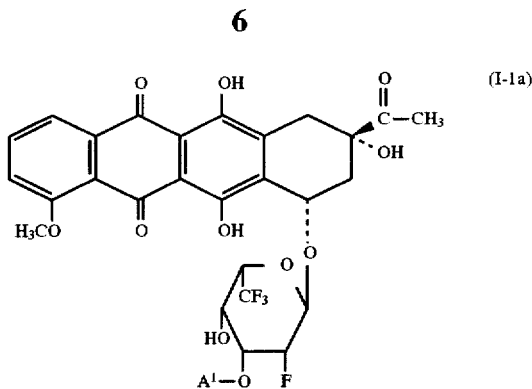

wherein $A^1$ is either (i) glycyl group or a substituted glycyl group of the formula (a) shown above, or (ii) an ω-amino acid residue of the formula (b) shown above.

(ii) Compound which is a 7-O-(2,6-dideoxy-2-fluoro-4-O-aminoalkanoyl-α-L-talopyanosyl)daunomycinone derivative represented by the general formula

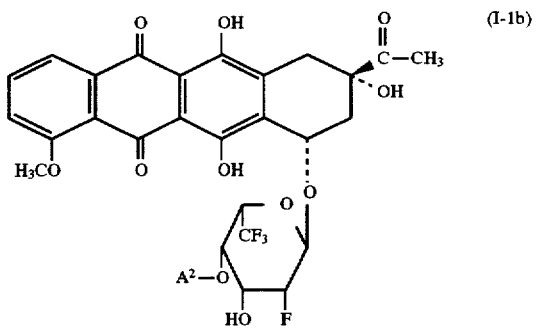

wherein $A^2$ is either (i) glycyl group or a substituted glycyl group of the formula (a) shown above, or (ii) an ω-amino acid residue of formula (b) shown above.

(iii) Compound which is a 7-O-(2,6-dideoxy-2-fluoro-3,4-di-O-aminoalkanoyl-α-L-talopyranosyl)daunomycinone derivative represented by the general formula

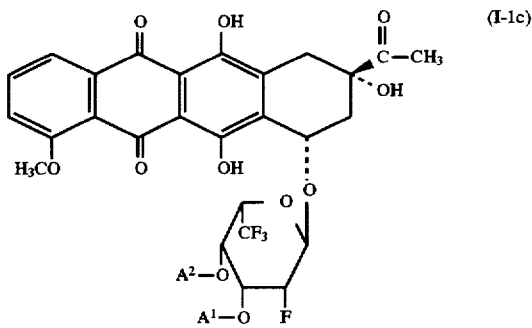

wherein both of $A^1$ and $A^2$ each are either (i) glycyl group or a substituted glycyl group of the formula (a) shown above, or (ii) an ω-amino acid residue of the formula (b) shown above.

(iv) Compound which is a 7-O-(2,6-dideoxy-2-fluoro-3-O-aminoalkanoyl-α-L-talopyranosyl)adriamycinone derivative represented by the general formula

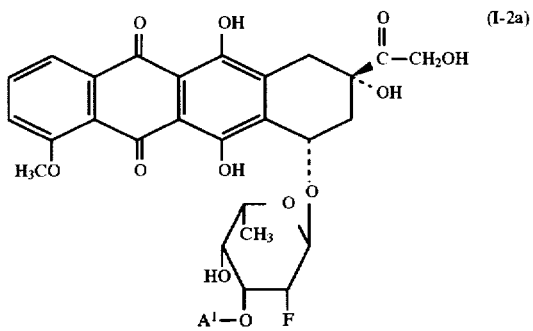

wherein $A^1$ is either (i) glycyl group or a substituted glycyl group of the formula (a) shown above, or (ii) an ω-amino acid residue of the formula (b) shown above.

(v) Compound, which is a 7-O-(2,6-dideoxy-2-fluoro-4-O-aminoalkanoyl-α-L-talopyranosyl)adriamycinone derivative represented by the general formula

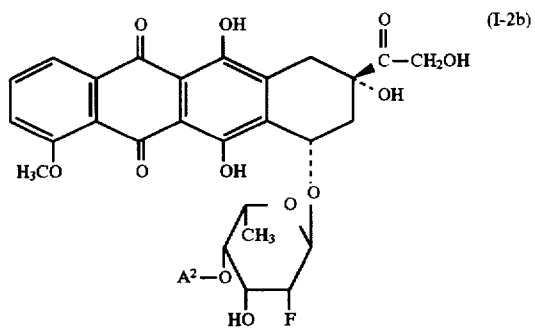

wherein $A^2$ is either (i) glycyl group or a substituted glycyl group of the formula (a) shown above, or (ii) an ω-amino acid residue of the formula (b) shown above.

(vi) Compound which is a 7-O-(2,6-dideoxy-2-fluoro-3,4-di-O-aminoalkanoyl-α-L-talopyranosyl)adriamycinone derivative represented by the general formula

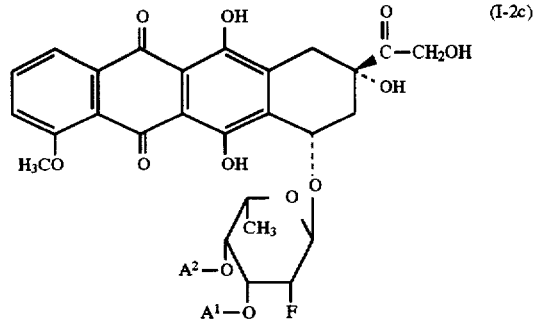

wherein both of $A^1$ and $A^2$ are either (i) glycyl group or a substituted glycyl group of the formula (a) shown above, or (ii) an ω-amino acid residue of the formula (b) shown above.

According to a second aspect of this invention, there is provided a 7-O-(2,6-dideoxy-2,6,6,6-tetrafluoro-3-O- or -4-O- or -3,4-di-O-aminoalkanoyl-α-L-talopyranosyl) adriamycinone derivative or 7-O-(2,6-dideoxy-6,6,6-trifluoro-3-O- or -4-O- or -3,4-di-O-aminoalkanoyl-α-L-lyxohexopyranosyl)adriamycinone derivative represented by the general formula

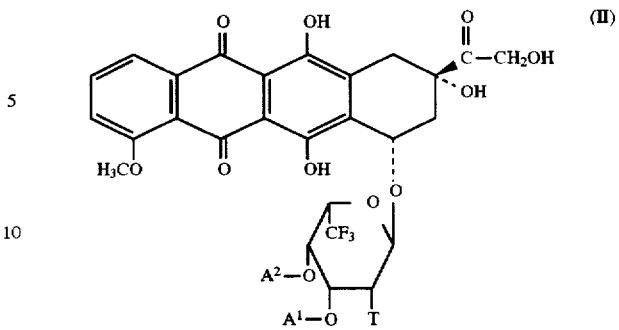

wherein T is a fluorine atom or a hydrogen atom, and either one or both of $A^1$ and $A^2$ is or are (i) glycyl group or a substituted glycyl group represented by the following formula (a):

where R is a hydrogen atom or an alkyl group of 1–8 carbon atoms, or an aryl group, particularly, phenyl group or a substituted phenyl group, or an aralkyl group, particularly a phenyl-($C_1$–$C_6$)alkyl group, or :(ii) an ω-amino acid residue represented by the following formula (b):

where B is a linear alkylene group of 2–6 carbon atoms which may optionally be substituted by a ($C_1$–$C_6$) alkyl group, or a pharmaceutically acceptable acid addition salt thereof.

The anthracycline derivative of the general formula (II) according to the second aspect of this invention embraces new compounds of six classes (i) to (vi) as described below.

(i) Compound which is a 7-O-(2,6-dideoxy-2,6,6,6-tetrafluoro-3-O-aminoalkanoyl-α-L-talopyranosyl) adriamycinone derivative represented by the general formula

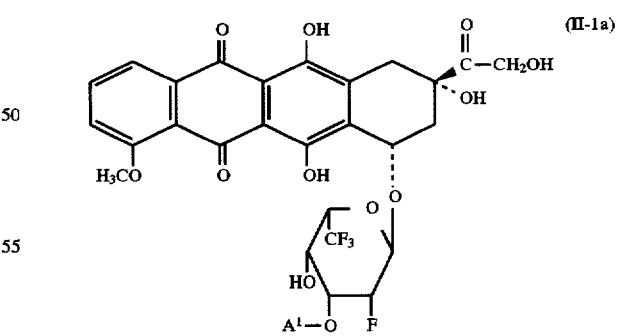

wherein $A^1$ is either (i) glycyl group or a substituted glycyl group of the formula (a) shown above, or (ii) an ω-amino acid residue of the formula (b) shown above.

(ii) Compound which is a 7-O-(2,6-dideoxy-2,6,6,6-tetrafluoro-4-O-aminoalkanoyl-α-L-talopyranosyl) adriamycinone derivative represented by the general formula

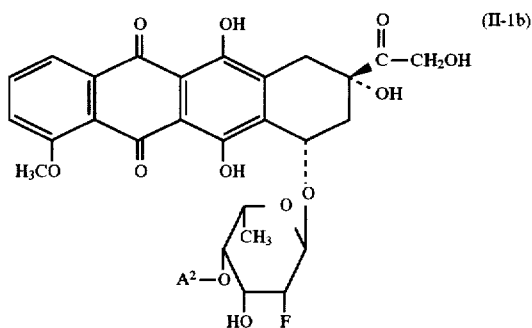
(II-1b)

wherein $A^2$ is either (i) glycyl group or a substituted glycyl group of the formula (a) shown above, or (ii) an ω-amino acid residue of the formula (b) shown above.

(iii) Compound which is a 7-O-(2,6-dideoxy-2,6,6,6-tetrafluoro-3,4-di-O-aminoalkanoyl-α-L-talopyranosyl) adriamycinone derivative represented by the general formula

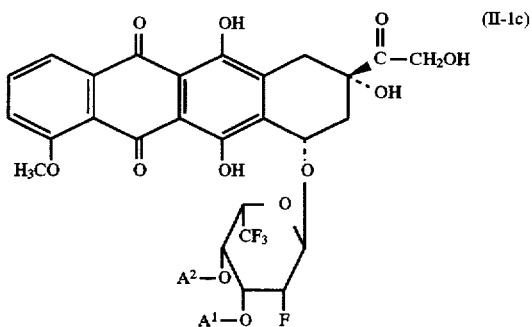
(II-1c)

wherein both of $A^1$ and $A^2$ each are either (i) glycyl group or a substituted glycyl group of the formula (a) shown above, or (ii) an ω-amino acid residue of the formula (b) shown above.

(iv) Compound which is a 7-O-(2,6-dideoxy-6,6,6-trifluoro-3-O-aminoalkanoyl-α-L-lyxo-hexopyranosyl) adriamycinone derivative represented by the general formula

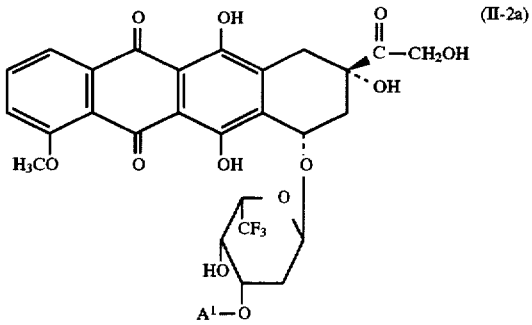
(II-2a)

Wherein $A^1$ is either (i) glycyl group or a substitued glycyl group of the formula (a) shown above, or (ii) an ω-amino acid residue of formula (b) shown above.

(v) Compound which is a 7-O-(2,6-dideoxy-6,6,6-trifluoro-4-O-aminoalkanoyl-α-L-lyxo-hexopyranosyl) adriamycinone derivative represented by the general formula

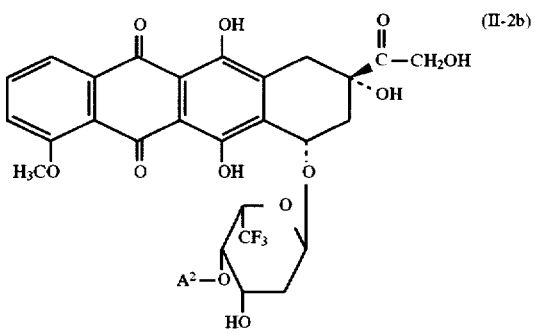
(II-2b)

wherein $A^2$ is either (i) glycyl group or a substituted glycyl group of the formula (a) shown above, or (ii) an ω-amino acid residue of the formula (b) shown above.

(vi) Compound which is a 7-O-(2,6-dideoxy-6,6,6-trifluoro-3,4-di-O-aminoalkanoyl-α-L-lyxo-hexopyranosyl) adriamycinone derivative represented by the general formula

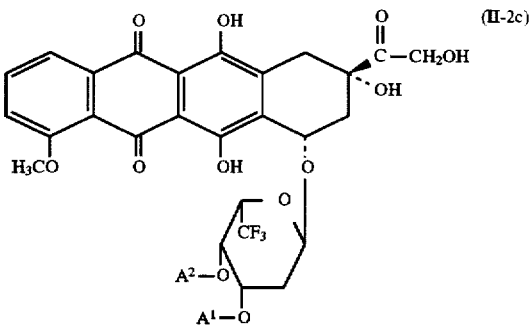
(II-2c)

wherein both of $A^1$ and $A^2$ each are either (i) glycyl group or a substituted glycyl group of the formula (a) shown above, or (ii) an ω-amino acid residue of the formula (b) shown above.

$A^1$ or $A^2$ in the compound of the general formula (I) according to the first aspect of this invention or in the compound of the general formula (II) according to the second aspect of this invention may be, for example, glycyl group or a substituted glycyl group which may be L-alanyl group, L-valyl group, L-leucyl group, L-isoleucyl group or L-phenylalanyl group.

Also, $A^1$ or $A^2$ in the compound of the general formula (I) or (II) above may be an ω-amino acid residue of the formula —CO—B—$NH_2$ where B has the meanings as defined hereinbefore, when $A^1$ or $A^2$ may be, for example, 3-aminopropionyl group, 4-aminobutyryl group or 4-amino-2,2-dimethylbutyryl group.

Examples of the pharmaceutically acceptable acid addition salt formed at the amino group(s) of the anthracycline derivative according to the first aspect or the second aspect of this invention includes the acid addition salts with a pharmaceutically acceptable inorganic acid such as hydrochloric acid, sulfuric acid, nitric acid or phosphoric acid, or a pharmaceutically acceptable organic acid such as acetic acid, trifluoroacetic acid, propionic acid, malonic acid, lactic acid, tartaric acid or methanesulfonic acid.

Further, the anthracycline derivative of the general formula (I) according to the first aspect of this invention embraces the under-mentioned compounds as preferable particular examples of the derivative of the formula (I).

(1) 7-O-[3-O-(3-aminopropionyl)-2-6-dideoxy-2-fluoro-α-L-talopyranosyl]daunomycinone (2) 7-O-[4-O-(3-aminopropionyl)-2,6-dideoxy-2-fluoro-α-L-talopyranosyl]daunomycinone (3) 7-O-(2,6-dideoxy-2-fluoro-3-O-glycyl-α-L-talopyranosyl)adriamycinone (4) 7-O-(2,6-dideoxy-2-fluoro-4-O-glycyl-α-L-talopyranosyl)adriamycinone (5) 7-O-(2,6-dideoxy-2-fluoro-3,4-di-O-glycyl-α-L-talopyranosyl)adriamycinone (6) 7-O-(3-O-L-alanyl-2,6-dideoxy-2-fluoro-α-L-talopyranosyl)adriamycinone (7) 7-O-(4-O-L-alanyl-2,6-dideoxy-2-fluoro-α-L-talopyranosyl)adriamycinone (8) 7-O-(3,4-di-O-L-alanyl-2,6-dideoxy-2-fluoro-α-L-talopyranosyl)adriamycinone (9) 7-O-(2,6-dideoxy-2-fluoro-3-O-L-phenylalanyl-α-L-talopyranosyl)adriamycinone

(10) 7-O-(2,6-dideoxy-2-fluoro-4-O-L-phenylalanyl-α-L-talopyranosyl)adriamycinone

(11) 7-O-(2,6-dideoxy-2-fluoro-3,4-di-O-L-phenylalanyl-α-L-talopyranosyl)adriamycinone

(12) 7-O-(2,6-dideoxy-2-fluoro-3-O-L-valyl-α-L-talopyranosyl)adriamycinone

(13) 7-O-(2,6-didoexy-2-fluoro-4-O-L-valyl-α-L-talopyranosyl)adriamycinone

(14) 7-O-[3,4-di-O-(3-aminopropionyl)-2,6-dideoxy-2-fluoro-α-L-talopyranosyl]adriamycinone The adriamycinone derivative of the general formula (II) according to the second aspect of this invention embraces the under-mentioned compounds as preferable particular examples of the derivatives of the formula (II).

(1) 7-O-(2,6-dideoxy-2,6,6,6-tetrafluoro-3-O-glycyl-α-L-talopyranosyl)adriamycinone (2) 7-O-(2,6-dideoxy-2,6,6,6-tetrafluoro-4-O-glycyl-α-L-talopyranosyl)adriamycinone (3) 7-O-(2,6-dideoxy-2,6,6,6-tetrafluoro-3,4-di-O-glycyl-α-L-talopyranosyl)adriamycinone (4) 7-O-[3,4-di-O-(3-aminopropionyl)-2,6-dideoxy-2,6,6,6-tetrafluoro-α-L-talopyranosyl]adriamycinone (5) 7-O-(3-O-L-alanyl-2,6-dideoxy-2,6,6,6-tetrafluoro-α-L-talopyranosyl)adriamycinone (6) 7-O-(4-O-L-alanyl-2,6-dideoxy-2,6,6,6-tetrafluoro-α-L-talopyranosyl)adriamycinone (7) 7-O-(3,4-di-O-L-alanyl-2,6-dideoxy-2,6,6,6-tetrafluoro-α-L-talopyranosyl)adriamycinone (8) 7-O-(2,6-dideoxy-2,6,6,6-tetrafluoro-3-O-L-phenylalanyl-α-L-talopyranosyl)adriamycinone (9) 7-O-(2,6-dideoxy-2,6,6,6-tetrafluoro-4-O-L-phenylalanyl-α-L-talopyranosyl)adriamycinone

(10) 7-O-(2,6-dideoxy-2,6,6,6-tetrafluoro-3,4-di-O-L-phenylalanyl-α-L-talopyranosyl)adriamycinone

(11) 7-O-(2,6-dideoxy-6,6,6-trifluoro-3-O-glycyl-α-L-lyxo-hexopyranosyl)adriamycinone

(12) 7-O-(2,6-dideoxy-6,6,6-trifluoro-4-O-glycyl-α-L-lyxo-hexopyranosyl)adriamycinone

(13) 7-O-(2,6-dideoxy-6,6,6-trifluoro-3,4-di-O-glycyl-α-L-lyxo-hexopyranosyl)adriamycinone

(14) 7-O-[3,4-di-O-(3-aminopropionyl)-2,6-dideoxy-6,6,6-trifluoro-α-L-lyxo-hexopyranosyl]adriamycinone

(15) 7-O-(3-O-L-alanyl-2,6-dideoxy-6,6,6-trifluoro-α-L-lyxo-hexopyranosyl)adriamycinone

(16) 7-O-(4-O-L-alanyl-2,6-dideoxy-6,6,6-trifluoro-α-L-lyxo-hexopyranosyl)adriamycinone

(17) 7-O-(3,4-di-O-alanyl-2,6-dideoxy-6,6,6-trifluoro-α-L-lyxo-hexopyranosyl)adriamycinone

(18) 7-O-(2,6-dideoxy-6,6,6-trifluoro-3-O-L-phenylalanyl-α-L-lyxo-hexopyranosyl)adriamycinone

(19) 7-O-(2,6-dideoxy-6,6,6-trifluoro-4-O-L-phenylalanyl-α-L-lyxo-hexopyranosyl)adriamycinone

(20) 7-O-(2,6-dideoxy-6,6,6-trifluoro-3,4-di-O-L-phenylalanyl-α-L-lyxo-hexopyranosyl)adriamycinone Through some tests, it has been confirmed that the compounds of the general formula (I) according to the first aspect of this invention have markedly high antitumor activities against experimental tumors in animals, and that the antitumor activities of the compounds of the formula (I) of this invention are comparable with or remarkably superior to the antitumor activities of daunomycin and adriamycin.

Some examples of tests are now described in Test Example 1 below to show the antitumor activities of several compounds which are embraced by the compounds of the general formula (I) according to this invention.

Test Example 1

In this Example, some tests were made to demonstrate the antitumor activities of the anthracycline derivatives according to the first aspect of this invention which were shown against leukemia in $CDF_1$ mice as induced by a mouse leukemia with Leukemia L-1210 cells.

Thus, to evaluate the antitumor effects of the new compounds according to the first aspect of this invention against experimental tumors in animals, $CDF_1$ mice (four mice per group) were intraperitoneally transplanted with cells of Leukemia L-1210 at an amount of $1 \times 10^5$ cells/mouse. Since an elapsed time of 24 hours from the transplantation of the leukemia cells, a test compound according to this invention was administered intraperitoneally to the mice under test for 9 consecutive days once per day. The mice so treated were observed for 60 days after the administration of the test compound. While, mice of the control group (the untreated group) were administered with only physiological saline after the transplantation of the L-1210 cells. During the observation period, the numbers of the surviving mice in the treated group and in the control group were counted, and the mean survival days of mice in the treated group and in the control group were then calculated. From the mean survival day (C) of the untreated mice of the control group and the mean survival day (T) of the treated mice of the treated group, there were evaluated percentages (%) of the increase in the life-span of the treated mice, as T/C %. For a comparison purpose, 7-O-(2,6-dideoxy-2-fluoro-α-L-talopyranosyl)daunomycinone (abbreviation: FT-DM); 7-O-(2,6-dideoxy-2-fluoro-α-L-talopyranosyl)adriamycinone (abbreviation: FT-ADM); and adriamycin were also tested in the same manner as above. The test results so obtained are shown in Table 1 below. Incidentally, the mean survival day of mice of the control group (the untreated group) was amounting to 8 to 9 days, and the mean survival day of mice of the comparative groups having received the administration of adriamycin was varying dependently on the dosage of adriamycin.

Meanwhile, the symbol ">" shown in Table 1 indicates that such mice which could be cured by the administration of the test compound and survive for 60 days or longer were observed at a rate of at least one mouse among the four mice tested in a group.

Besides, the compound number shown in Table 1 below means Compound No. as indicated in the Examples 1~11 given hereinafter.

TABLE 1

| Compound tested | % Increase in life-span (T/C, %) Dosage (mg/kg/day) | | | | | |
|---|---|---|---|---|---|---|
| | 5 | 2.5 | 1.25 | 0.6 | 0.3 | 0.15 |
| 7-O-[3-O- and -[4-O-(3-aminopropionyl)-2,6-dideoxy-2-fluoro-α-L-talopyranosyl]daunomycinones (a mixture of Compound 3 + Compound 4; as trifluoroacetate) | 156 | 142 | 102 | 105 | 95 | 102 |
| 7-O-(2,6-Dideoxy-2-fluoro-3-O- and -4-O-glycyl-α-L-talopyranosyl)adriamycinones (a mixture of Compound 8a + Compound 9a, as trifluoroacetate) | >800 (4/4) | >583 (2/4) | 340 | 230 | 160 | 123 |
| 7-O-(2,6-Dideoxy-2-fluoro-3,4-di-O-glycyl-α-L-talopyranosyl)adriamycinone (Compound 11a, as trifluoroacetate) | >518 (2/4) | >430 (1/4) | 321 | 170 | 125 | 111 |
| 7-O-(3-O- and -(4-O-L-Alanyl-2,6-dideoxy-2-fluoro-α-L-talopyranosyl)adriamycinones (a mixture of Compound 8b + Compound 9b, as trifluoroacetate) | >787* (4/4) | >534 (2/4) | >669 (3/4) | >705 (3/4) | >495 (2/4) | 207 |
| 7-O-(3,4-Di-O-L-alanyl-2,6-dideoxy-2-fluoro-α-L-talopyranosyl)adriamycinone (Compound 11b, as trifluoroacetate) | >502 (2/4) | >666 (2/4) | >407 (1/4) | >361 (1/4) | 144 | 115 |
| 7-O-(2,6-Dideoxy-2-fluoro-3-O- and -4-O-L-phenylalanyl-α-L-talopyranosyl)adriamycinones (a mixture of Compound 8c + Compound 9c, as trifluoroacetate) | >613* (2/4) | 240 | >333 (1/4) | >313 (1/4) | 153 | 127 |
| 7-O-(2,6-Dideoxy-2-fluoro-3,4-di-O-L-phenylalanyl-α-L-talopyranosyl)adriamycinone (Compound 11c, as trifluoroacetate) | 253 | 177 | 170 | 143 | 130 | 123 |
| 7-O-(2,6-Dideoxy-2-fluoro-3-O- and -4-O-L-valyl-α-L-talopyranosyl)adriamycinones(a mixture of Compound 8d + Compound 9d, as trifluoroacetate) | >683 (3/4) | >567 (2/4) | >343 (1/4) | 157 | 147 | 127 |
| 7-O-(2,6-Dideoxy2-fluoro-α-L-talopyranpsyl)-daunomycinone (FT-DM) (Comparative) | 184 | 217 | 171 | 125 | 105 | 105 |
| 7-O-(2,6-Dideoxy-2-fluoro-α-L-talopyranosyl)-adriamycinone (FT-ADM) (Comparative) | >740 (4/4) | >352 (1/4) | 275 | 185 | 182 | 127 |
| Adriamycin (as hydrochloride) (Comparative) | 177* | 273* | 330 | 208 | 132 | 140 |

Notes: Asterisks (*) indicate that development of toxicity such as toxicity-related death or a body weight loss was observed on the corresponding mice tested.

As will be clear from the test results of Table 1 above, the compound of the general formula (I) according to the first aspect of this invention can exhibit such antitumor activities which are comparable to or have been enhanced remarkably much than those of the parent compounds, FT-DM and FT-ADM. In particular, when the mixture of Compound 8b and Compound 9b as tested was administered to mice at a dosage in a range of 5 mg/kg to 0.3 mg/kg, it is worthy of paying attention on that, among the 20 mice under test, 14 mice could survive for more than 60 days and could be observed to have been cured fully by the administration of the mixture of Compounds 8b and 9b, indicating that Compounds 8b and 9b each can exhibit remarkably improved antitumor activities in comparison with those of the parent compound, FT-ADM. It is also worthy of paying attention on that there are observed such mice which could survive for 60 days, even when the mixture of Compound 8b and Compound 9b was administered to the mice under test especially at a low dosage of from 1.25 mg/kg to 0.3 mg/kg. It is further seen that Compound 11b under test according to this invention can exhibit such antitumor activities which are a little inferior to the antitumor activities of said mixture of Compounds 8b and 9b but are yet considerably high antiumor activities.

Furthermore, in order to estimate the antitumor activities of the O-aminoalkanoylated daunomycinone or adriamycinone derivatives according to the first and second aspects of this invention, some "in vitro" tests for inhibiting proliferation of cancer cells were conducted as shown in the following.

Test Example 2

Among the new compounds according to the first and second aspects of this invention, there were chosen several test compounds. And, the test compounds so chosen were added at varying concentrations to mouse leukemia, P388 cells or adriamycin-resistant P388 cells (P388/ADR) which had been incubated in test tubes containing an appropriate culture medium. The incubation of the tumor cells were then continued for 72 hours from the addition of the test compound, and determination was made to evaluate such concentrations of the test compound which could inhibit the growth of the leukemia cells by 50% (namely, $IC_{50}$, ng/ml). Adriamycin (as the hydrochloride) was used as a comparative compound and was tested in the same manner as above. The test results obtained are summarized in Table 2 below.

While, the compound number shown in Table 2 means Compound No. as indicated in the Examples 1~23 given hereinafter.

TABLE 2

| Test Compound | $IC_{50}$ (ng/ml) | |
|---|---|---|
| | P388 | P388/ADR |
| Mixture of compound 3 + Compound 4 | 31 | 98 |
| Mixture of Compound 8a + Compound 9a | <9.8 | 97 |
| Compound 11a | <9.8 | 320 |
| Mixture of Compound 8b + Compound 9b | <9.8 | 270 |
| Compound 11b | <9.8 | 310 |
| Mixture of Compound 8c + Compound 9c | 18 | 190 |
| Compound 11c | 26 | 140 |
| Mixture of Compound 8d + Compound 9d | 26 | 340 |
| Compound 11d | <9.8 | 320 |
| Mixture of Compound 8e + Compound 9e | 20 | 170 |
| Compound 11e | 32 | 270 |
| Compound Mixture of Compound 15 + Compound 16 | <9.8 | 170 |

TABLE 2-continued

| Test Compound | IC₅₀ (ng/ml) | |
|---|---|---|
| | P388 | P388/ADR |
| Compound 18 | <9.8 | 280 |
| Mixture of Compound 22 + Compound 23 | <9.8 | 120 |
| Compound 25 | <9.8 | 290 |
| Mixture of compound 28 + Compound 29 | <9.8 | 120 |
| Compound 31 | <9.8 | 140 |
| Mixture of Compound 34 + Compound 35 | <9.8 | 180 |
| Compound 37 | 16 | 170 |
| Mixture of Compound 40 + Compound 41 | <9.8 | 180 |
| Compound 43 | <9.8 | 220 |
| Mixture of Compound 46 + Compound 47 | 17 | 190 |
| Compound 49 | 20 | 280 |
| Adriamycin (as hydrochloride) (Comparative) | 33 | 1,300 |

Note: All the test compounds according to this invention were used in the form of their trifluoroacetate.

As will be clear form the test results of Table 2 above, it is evident that all the compounds under test according to this invention, except the mixture of Compound 3 and Compound 4, can inhibit the growth of the P388 cells at IC₅₀ values lower than the comparative adriamycin and hence exhibit higher antitumor activities than those of adriamycin. Besides, all the compounds of this invention as tested can exhibit higher antitumor activities against the P388/ADR cells than adriamycin.

Daunomycin or adriamycin employed as the comparative drug in Test Examples 1~2 above is a carcinostatic agent which is actually used in clinical treatments. Daunomycin or adriamycin is administered to men at doses in a range of from 0.4 mg/kg to 2 mg/kg depending on the types of cancers to be treated. When the clinically utilized daunomycin or adriamycin is administered at a dose of form 2.5 mg/kg/day to 5 mg/kg/day to the mice which has been inoculated with the L-1210 cells, daunomycin and adriamycin each exhibit the anticancer or antitumor effects such that the percentages (%) of increase in life-span (T/C, %) so obtained amount to about 138% to 171% and to approximately 330% at maximum, with being accompanied by development of toxicity.

In contrast, it should be worthy to note that many of the tested compounds of this invention as administered at an appropriate low dosage in a range of from 0.3 mg/kg/day to 5 mg/kg/day are not accompanied by development of toxicity but are able to afford the remarkably higher percentages of increase in the life-span (as T/C, %) than daunomycin and adriamycin, and that the many tested compounds of this invention so administered can exhibit very much excellent antitumor effects such that the percentages of increase in the life-span obtained are amounting to about 300% or more, with involving some cases of the complete curing of the L-1210 cell-inoculated mice. Therefore, many of the new compounds of this invention have such an advantage that their antitumor effects can be expected to be obtained in the clinical treatments of cancer-bearing patients even when they are adminstered at a non-large dosage to the patients.

From the foregoing, it is considered that the novel anthracycline derivatives having the general formula (I) and the formula (II) respectively according to the first aspect and the second aspect of this invention have excellent antitumor activities and have low toxicities.

Thus, said novel anthracycline derivatives of this invention are very much useful as the antitumor drug which is practically usable in the clinical treatments of the patients, and they are expectable to be valuable for use in therapeutic treatments of various kinds of tumors, similarly to daunomycin or adriamycin. Consequently, the compounds of the general formula (I) according to the first aspect of this invention, as well as the compound of the formula (II) according to the second aspect of this invention can be utilized usefully as therapeutic agents for tumors or cancers in the medicinal treatments of solid cancers, ascitic cancers and the like.

According to a third aspect of this invention, therefore, there is provided a pharmaceutical composition, characterized in that the composition comprises as an active ingredient an anthracycline derivative represented by the general formula (I) described hereinbefore, or an adriamycinone derivative represented by the formula (II) described hereinbefore, or an acid addition salt thereof, in combination with a pharmaceutically acceptable carrier.

When the compound of the general formula (I) or the formula (II) according to this invention is administered in practice, it may usually be administered by a parenteral route. It is also feasible to administer the compound of this invention orally after the compound is mixed with a pharmaceutically acceptable solid or liquid carrier which is conventionally used in the pharmaceutic field, followed by formulating the resultant mixture into various preparation forms such as powder, granules, tablets or syrups, or injectable solutions and suspensions.

For a usual method for the administration, the compound of this invention may be administered to animals in the form of an injectable solution or suspension of the compound by intraperitoneal injection, subcutaneous injection, blood vessel injection, either intravenous or intra-arterial, or local injection and the like. The compound of this invention may be administered to humans also in the form of an injectable solution or suspension of the compound by blood vessel injection, either intravenous or intra-arterial, or local injection and the like. The compound of this invention may be administered continuously or intermittently at such dosages and to such an extent that the total dosage would not exceed a certain level as determined in view of results of animal tests and various circumstances.

The administration of the compound of this invention should, of course, be effected by changing the dosages of the compound appropriately in accordance with the way of administration and the conditions of the patients or animals to be treated, such as age, body weight, sex, sensitivity, foods, administration time, administration route, drugs to be administered in combination and the seriousness of patients or disease, etc. The compound of this invention may be administered at a substantially same dose as that of daunomycin or adriamycin when the compound is used as an antitumor or anticancer agent. Optimum dosage and frequency of administration of the compound of this invention under certain specific conditions must be determined by medicinal experts through preliminary tests in view of the above-mentioned guideline. These requirements for administration are equally applied to the oral administration of the compound of this invention.

A further aspect of this invention includes a use of a daunomycinone or adriamycinone derivative having the general formula (I) as defined hereinbefore, or an adriamycinone derivative having the general formula (II) as defined hereinbefore, or a pharmaceutically acceptable acid addition salt thereof, in the manufacture of a pharmaceutical composition, particularly an antitumor composition.

Next, processes for the preparation of the novel anthracycline derivatives according to this invention are described below.

(A) The preparation of 7-O-(2,6-dideoxy-2-fluoro-3-O-amino-alkanoyl-α-L-talopyranosyl)daunomycinone of the general formula (I-1a) according to the first aspect of this invention may be conducted by the following process.

Thus, the preparation of the compound of the general formula (I-1a) may be conducted by such a process which comprises dissolving in pyridine 7-O-(2,6-dideoxy-2-fluoro-α-L-talopyranosyl)daunomycinone (Compound A'; one of the compounds having the formula (A) defined hereinbefore) set forth in the specification of the Japanese patent publication "Kokoku" No. Hei-6-31298 or the European patent No. 0230013; adding to the resulting solution in pyridine such an N-protected amino acid active ester, e.g., N-succinimide ester, that may be either (i) an N-protected glycine or other a-amino acid of the general formula

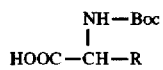

(III)

where R has the meanings as defined hereinbefore and Boc denotes tert-butoxycarbonyl group as an amino-protecting group, or (ii) an N-protected ω-amino acid of the general formula HOOC—B—NH-Boc (IV)

where B and Boc have the meanings as defined hereinbefore, with the proportion of the N-protected amino acid as added being equimolar to or in a slight excess over the amount of said Compound A'; stirring the resultant mixture at an elevated temperature of e.g. 50° to 60° C. under heating to esterify preferentially the 3'-hydroxyl group of said Compound A' with the N-protected amino acid; and then eliminating the amino-protecting group (Boc) in a known manner from the esterification product obtained.

In the above-mentioned esterification reaction, the 3'-hydroxyl group of the starting Compound A' can preferentially be esterified with the N-protected amino acid of the formula (III) or formula (IV), thereby to produce a 7-O-[2,6-dideoxy-2-fluoro-3-O-(N-Boc-amino-alkanoyl)-α-L-talopyranosyl]daunomycinone having the general formula

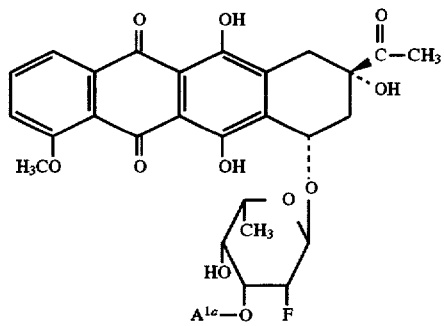

wherein $A^{1a}$ is either N-Boc-glycyl group or other N-Boc-α-amino acid residue of the formula (a'):

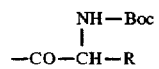

(a')

where R and Boc have the same meanings as defined above, or an N-Boc-ω-amino acid residue of the formula (b'):

—CO—B—NH-Boc (b')

where B and Boc have the same meanings as defined above.

From the resulting reaction solution of said esterification reaction is then recovered by an appropriate procedure the 3'-mono-O-(N-Boc-aminoalkanoyl) compound of the formula (I-1a) above (namely, the N-Boc-3'-ester), which is subsequently dissolved in aqueous trifluoroacetic acid for the deprotecting treatment, whereby the amino-protecting group, Boc, can be removed by acidic hydrolysis to the produce the target compound of the formula (I-1a) (namely, the 3'-ester) in the form of trifluoroacetate.

Further, when the above-mentioned esterification reaction is effected for a prolonged reaction time, a part or a larger part of the compound of the formula (I-1a') can undergo such migration process that the N-Boc-amino acid residue ($A^{1a}$) will migrate from the 3'-hydroxyl group to the 4'-hydroxyl group of said compound, whereby there is produced a 7-O-[2,6-dideoxy-2-fluoro-4-O-(N-Boc-aminoalkanoyl)-α-L-talopyranosyl]daunomycinone having the general formula

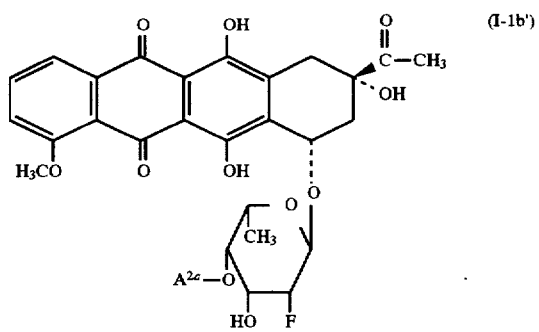

wherein $A^{2a}$ has the meaning same as $A^{1a}$ present in the general formula (I-1a') above, as the N-Boc-4'-ester.

In case the 4'-mono-O-(N-Boc-aminoalkanoyl) compound of the formula (1-1b') mentioned just above (namely, the N-Boc-4'-ester) has been produced, the esterification reaction solution containing the N-Boc-3'-ester of the formula (I-1a') and the N-Boc-4'-ester of the formula (I-1b') may be diluted with chloroform and the resulting diluted solution is extracted with an appropriate solvent for removal of unnecessary by-products therefrom, followed by concentrating the resultant solution in chloroform under reduced pressure to dryness, whereby there can be recovered a mixture of the compound of the formula (I-1a') and the compound of the formula (I-1b').

When the mixture of the compound (I-1a') and the compound (I-1b') so recovered is then dissolved in aqueous trifluoroacetic acid to effect the hydrolysis for removal of the Boc group, there is afforded a mixture of the compound of the general formula (I-1a) and the compound of the general formula (I-1b), respectively, in the form of their trifluoroacetates. When the deprotecting reaction with trifluoroacetic acid is effected, the process of migration of the 3'-O-aminoalkanoyl group to the 4'-hydroxyl group can also take place so that a change occurrs in the ratio between the 3'-ester of the formula (I-1a) and the 4'-ester of the formula (I-1b).

Even if the mixture of said 3'-ester [namely, the compound having the 3'-O-aminoalkanoyl group according to the formula (I-1a)] and said 4'-ester [namely, the compound having the 4'-O-aminoalkanoyl group according to the formula (I-1b)] is subjected to a chromatography under conventional conditions, it is difficult at present to separate the former (the 3'-ester) from the latter (the 4'-ester) each in their pure form. However, it may be expectable that the former and the latter could be recovered separately if any new method of isolating them from each other would be devised and applied to the mixture of the former and the latter.

(B) The 7-O-(2,6-dideoxy-2-fluoro-4-O-aminoalkanoyl-α-L-talopyranosyl)daunomycinone of the general formula (I-1b) according to the first aspect of this invention may be produced along with the compound of the general formula (I-1a) when the process as described in the above item (A) is conducted.

Otherwise, another process may be used to produce the compound of the general formula (I-1b). Thus, the 3'-hydroxyl group of the starting Compound A' is at first selectively esterified with the active ester of the N-protected amino acid of the formula (III) or formula (IV) in accordance with the process of the above item (A), to produce the N-Boc-3'-ester of the general formula (I-1a') above, which is then subjected to such a method comprising isolating the said N-Boc-3'-ester of the formula (I-a') from the resultant reaction solution, dissolving the N-Boc-3'-ester in acetonitrile, adding silica gel to the resultant solution and refluxing the resulting mixture. In this method, there takes place the migration process that the N-protected amino acid residue at the 3'-position of the compound of the formula (I-1a') migrates to the 4'-position, in the same way as explained in the above item (A). Consequently, a larger part of the N-Boc-3'-ester of the general formula (I-1a') can be converted into the N-Boc-4'-ester of the general formula (I-1b') above.

The resulting reaction solution containing the above-mentioned two esters so produced may then be treated to recover a mixture of these two esters therefrom, followed by treating the recovered ester mixture with trifluoroacetic acid to eliminate the amino-protecting group, Boc, therefrom, whereby there may be afforded a mixture of the 3'-ester of the formula (I-1a) and the 4'-ester of the formula (I-1b) each in the form of their trifluoroacetates.

Even when said mixture of the 3'-ester and 4'-ester is subjected to a chromatography under conventional conditions, it is not feasible to recover the 3'-ester of the formula (I-1a) and the 4'-ester of the formula (I-1b) separately from each other. However, separate isolation of the 3'-ester from the 4'-ester could be possible if a new method of separating them from each other would be devised and applied to said mixture.

(C) The production of the 7-O-(2,6-dideoxy-2-fluoro-3, 4-di-O-aminoalkanoyl-α-L-talopyranosyl)daunomycinone of the general formula (I-1c) according to the first aspect of this invention may be conducted by the following process.

Thus, the compound of the formula (I-1c) may be produced by such a process which comprises reacting the starting Compound A' employed in the process explained in the above item (A), namely 7-O-(2,6-dideoxy-2-fluoro-α-L-talopyranosyl)daunomycinone in pyridine with the active ester of the N-protected amino acid of the formula (III) or formula (IV) in 2 molar proportions or in a slight excess over the amount of Compound A' to esterify both the 3'- and 4'-hydroxyl groups of the starting Compound A' and thereby to produce a 7-O-[2,6-dideoxy-2-fluoro-3,4-di-O-(N-Boc-aminoalkanoyl)-α-L-talopyranosyl]daunomycinone having the general formula

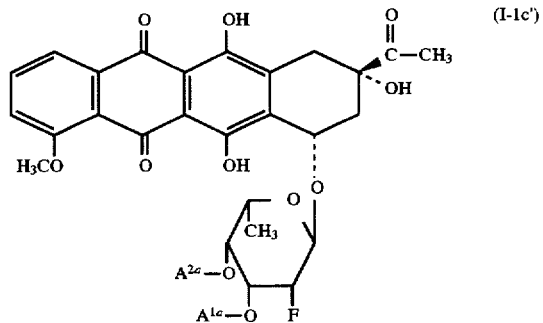

wherein both of $A^{1a}$ and $A^{2a}$ each are either N-Boc-glycyl group or other N-Boc-α-amino acid residue of the formula (a'):

where R and Boc have the same meanings as defined above, or an N-Boc-ω-amino acid residue of the formula (b'):

where B and Boc have the same meanings as defined above, and then treating this N-Boc-3',4'-diester compound of the formula (I-1c') with trifluoroacetic acid to eliminate the amino-protecting group, Boc, therefrom, affording the 3',4'-diester compound of the formula (I-1c).

In the process described just above, the reaction of esterification of the starting Compound A', as well as the deprotecting reaction of eliminating the Boc group from the N-Boc-3'4'-diester compound of the formula (I-1c') may be carried out in the same manner as described in the foregoing item (A).

Otherwise, the 3',4'-diester compound of the general formula (I-1c) can be produced also by means of such a process which comprises effecting at first the process described in the above item (A) so as to produce the N-Boc-3'-ester compound of the formula (I-1a') and the N-Boc-4'-ester compound of the formula (I-1b') in the form of a mixture of them; recovering this mixture from the reaction solution; dissolving this mixture in pyridine; reacting the N-Boc-3'- and -4'-esters in pyridine with the active ester of the N-protected amino acid of the formula (III) or formula (IV) added in an equimolar proportion to said esters to effect the esterification reaction; thereby producing the N-Boc-3',4'-diester compound of the general formula (I-1c') above; and then eliminating the Boc group from said N-Boc-3',4'-diester compound by treatment with trifluoroacetic acid.

(D) The preparation of 7-O-(2,6-dideoxy-2-fluoro-3-O-aminoalkanoyl-α-L-talopyranosyl)adriamycinone of the general formula (I-2a) according to the second aspect of this invention may be conducted by the following process.

Thus, the compound of the formula (I-2a) may be produced by means of such a process which comprises firstly utilizing as a starting compound 7-O-(2,6-dideoxy-2-fluoro-α-L-talopyranosyl)adriamycinone (Compound A"; one of the compounds of the general formula (A) given hereinbefore); reacting Compound A" in N,N-dimethylformamide (DMF) with tert-butylchlorodimethylsilane in the presence of imidazole to tert-butyldimethylsilylate the primary hydroxyl group at the 14-position of said Compound A" for the purpose of protecting the 14-hydroxyl group and thereby to produce 14-O-tert-butyldimethylsilyl-7-O-(2,6-dideoxy-2-fluoro-α-L-talopyranosyl)adriamycinone having the formula

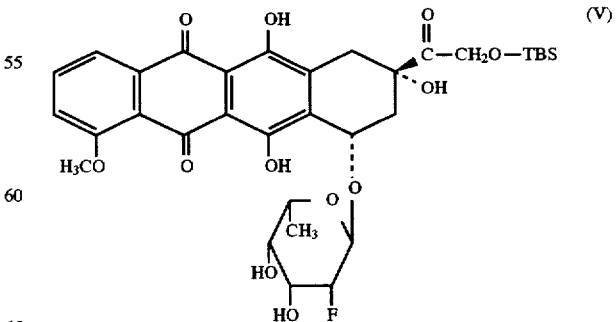

wherein TBS denotes tert-butyldimethylsilyl group as a hydroxyl-protecting group; then reacting the adriamycinone derivative of the above formula (V) in pyridine with an equimolar proportion or a slightly excessive proportion of the active ester of the N-protected amino acid of the general formula (III) or formula (IV) in a way similar to the reaction of esterification as described in the fore-going item (A), to esterify preferentially the 3'-hydroxyl group of the compound of the formula (V) and thereby to produce a 14-O-TBS-7-O-|2,6-dideoxy-2-fluoro-3-O-(N-Boc-aminoalkanoyl)-α-L-talopyranosyl|adriamycinone having the general formula

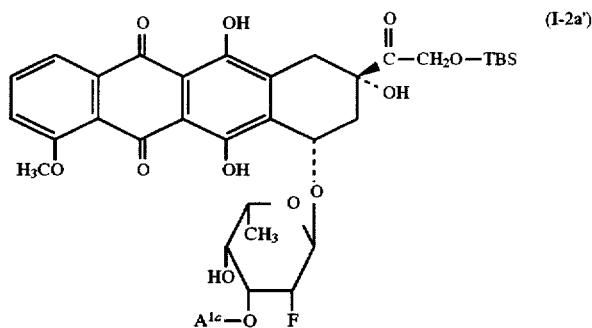

wherein TBS has the same meaning as defined above and $A^{1a}$ is either N-Boc-glycyl group or other N-Boc-α-amino acid residue of the formula (a'):

 (a')

where R and Boc have the same meanings as defined above, or an N-Boc-ω-amino acid residue of the formula (b'):

 (b')

where B and Boc have the same meanings as defined above; then isolating the N,O-protected-3'-ester compound of the formula (I-2a') from the reaction solution; and eliminating concurrently the amino-protecting group (Boc) and the hydroxyl-protecting group (TBS) from the compound (I-2a') by treatment with trifluoroacetic acid to produce the target compound of the formula (I-2a).

Meanwhile, when the above reaction of esterifying the adriamycinone derivative of the formula (V) with the active ester of the N-protected amino acid of the formula (III) or (IV) is carried out for a prolonged reaction time, a part or a larger part of the N,O-protected-3'-ester compound of the formula (I-2a') can undergo such migration process that the N-Boc-amino acid residue ($A^{1a}$) will migrate from the 3'-position to the 4'-position of the compound (I-2a'), whereby there is produced a 14-O-TBS-7-O-|2,6-dideoxy-2-fluoro-4-O-(N-Boc-aminoalkanoyl)-α-L-talopyranosyl| adriamycinone having the general formula

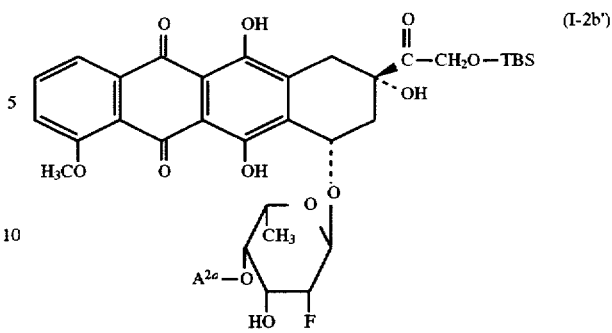

wherein TBS has the same meaning as defined above and $A^{2a}$ has the same meaning as that of $A^{1a}$ defined in the general formula (I-2a') shown hereinbefore.

Thereafter, the resulting esterification reaction solution containing both of the compound of the formula (I-2a') and the compound of the formula (I-2b') produced may be diluted with chloroform and the resultant diluted solution may be extracted with an appropriate solvent for removal of unnesessary by-products, followed by concentrating the chloroform solution obtained under reduced pressure to dryness, whereby there can be recovered a mixture of the compound of the formula (I-2a') and the compound of the formula (I-2b'). When this mixture so recovered is then treated with trifluoroacetic acid to effect simultaneous removal of the TBS group and Boc group from said two compounds, there is afforded a mixture of the compound of the general formula (I-2a) and the compound of the general formula (I-2b), respectively, in the form of their trifluoroacetates. When the treatment with trifluoroacetic acid for the removal of the protective groups is effected, the reaction of transfer of the 3'-O-aminoalkanoyl group to the 4'-hydroxyl group can also take place so that a change occurs in the ratio between the compound of the formula (I-2a) and the compound of the formula (I-2b).

Even if the mixture of the compound (I-2a) and the compound (I-2b) is subjected to a chromatography under conventional conditions, it is not feasible to isolate the compound of the formula (I-2a) and the compound of the formula (I-2b) separately in their pure form. However, it may be expectable that the former compound and the latter compound could be recovered separately from each other, if any new method of isolating them separately would be devised and applied to said mixture.

(E) A 7-O-(2,6-dideoxy-2-fluoro-4-O-aminoalkanoyl-α-L-talopyranosyl)adriamycinone of the general formula (I-2b) according to the first aspect of this invention may be produced by the process described in the item (D) above.

A second process for preparing the compound of the formula (I-2b) is such a process which comprises esterifying the compound of the formula (V) with the N-protected amino acid as described in the above item (D) to produce the compound of the formula (I-2a'); then separating this compound (I-2a') from the reaction solution by an appropriate procedure; dissolving the compound of the formula (I-2a') so recovered into acetonitrile; refluxing the resulting acetonitrile solution in the presence of silica gel to effect the migration process that the N-protected amino acid residue at the 3'-position of the compound of the formula (I-2a') will migrate to the 4'-position of said compound with forming the compound of the formula (I-2b'); then recovering a mixture of the compound of the formula (I-2b') and the non-transferred compound of the formula (I-2a') from the reac-

23 tion solution as formed in said transfer reaction; treating said mixture recovered with trifluoroacetic acid to eliminate simultaneously the TBS group and Boc group from each of the aforesaid two compounds and thereby to produce the compound of the formula (I-2b) and the compound of the formula (I-2a); and subsequently recovering a mixture of these two compounds. Even if this mixture of the compounds (I-2b) and the compound (I-2a) is subjected to a chromatography under conventional conditions, it is not feasible at present to isolate the compound of the formula (I-2b) and the compound of the formula (I-2a) separately each in their pure form. It will need to devise any new method for separating the compound (I-2b) from the compound (I-2a) in order to achieve separate recovery of these two compounds.

(F) The preparation of a 7-O-|2,6-dideoxy-2-fluoro-3,4-di-O-(aminoalkanoyl)-α-L-talopyranosyl|adriamycinone of the general formula (I-2c) according to the first aspect of this invention may be conducted by the following process.

Thus, the compound of the formula (I-2c) may be produced by such a process which comprises producing the N,O-protected-3'-ester product of the general formula (I-2a') and the N,O-protected-4'-ester product of the general formula (I-2b') in the form of a mixture of them in accordance with the process described in the item (E) above; recovering said mixture from the reaction solution; then dissolving said mixture in pyridine; adding to the resulting pyridine solution the active ester of the N-protected amino acid of the formula (III) or formula (IV) in an equimolar proportion to the ester products of the formulae (I-2a') and (I-2b') to effect the esterification reaction; thereby producing a 14-O-TBS-7-O-|2,6-dideoxy-2-fluoro-3,4-di-O-(N-Boc-aminoalkanoyl)-α-L-talopyranosyl|adriamycinone having the general formula

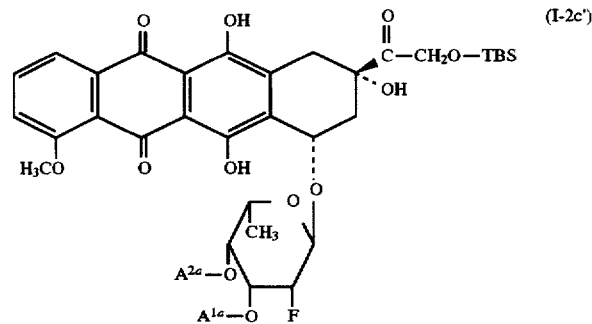

(I-2c')

wherein TBS has the same meaning as defined above and both of $A^{1a}$ and $A^{2a}$ are each either N-Boc-glycyl group or other N-Boc-α-amino acid residue of the formula (a'):

(a')

where R and Boc have the same meanings as defined above, or an N-Boc-ω-amino acid residue of the formula (b'):

(b')

where B and Boc have the same meanings as defined above; and then treating the compound of the formula (I-2c') with trifluoroacetic acid to effect simulataneous removal of the TBS group and Boc group therefrom and thereby to produce the compound of the formula (I-2c).

24

Or, the compound of the formula (I-2c) may be produced also by such other process which comprises reacting the 14-O-protected-adriamycinone derivative of the above formula (V) in pyridine directly with 2 molar proportions or a slightly excessive proportion of the active ester of the N-protected amino acid of the formula (III) or formula (IV); thereby producing the N,O-protected-3',4'-diester product of the general formula (I-2c') at once; and then treating the compound of the general formula (I-2c') with trifluoroacetic acid to effect simultaneous removal of the TBS group and Boc group therefrom, so that the compound of the general formula (I-2c) is produced in the form of its trifluoroacetate.

(G) The production of 7-O-(2,6-dideoxy-2,6,6,6-tetrafluoro-3-O-aminoalkanoyl-α-L-talopyranosyl) adriamycinone of the general formula (II-1a), as well as 7-O-(2,6-dideoxy-2,6,6,6-tetrafluoro-4-O-aminoalkanoyl-α-L-talopyranosyl)adriamycinone of the general formula (II-1b) according to the second aspect of this invention may be conducted by the following process.

Thus, the compound of the formula (II-1a) and the compound of the formula (II-1b) each may be produced by such a process which comprises utilizing as a starting compound 7-O-(2,6-dideoxy-2,6,6,6-tetrafluoro-α-L-talopyranosyl) adriamycinone of the formula (C-b) given hereinbefore (see the specification of the PCT application No. PCT/JP95/00407, and Referential Example 3 shown hereinafter); reacting this compound of the formula (C-b) with tert-butylchlorodimethylsilane in DMF in the presence of imidazole similarly to the process described in the item (D) hereinbefore, to tert-butyldimethylsilylate the primary 14-hydroxyl group of the starting compound for the purpose of protecting the 14-hydroxyl group and thereby to produce 14-O-tert-butyldimethylsilyl-7-O-(2,6-dideoxy-2,6,6,6-tetrafluoro-α-L-talopyranosyl)adriamycinone having the general formula

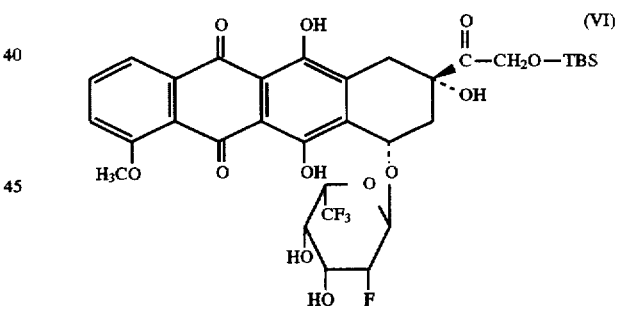

(VI)

wherein TBS denotes tert-butyldimethylsilyl group as a hydroxyl-protecting group; then reacting the adriamycinone derivative of the above formula (VI) in pyridine with an equimolar proportion or a slightly excessive proportion of the active ester of the N-protected amino acid of the formula (III) or formula (IV) shown hereinbefore, in the same way as in the process described in the foregoing item (A), to esterify preferentially the 3'-hydroxyl group of the compound of the formula (VI) and thereby to produce a 14-O-TBS-7-O-|2,6-dideoxy-2,6,6,6-tetrafluoro-3-O-(N-Boc-aminoalkanoyl)-α-L-talopyranosyl|adriamycinone having the general formula

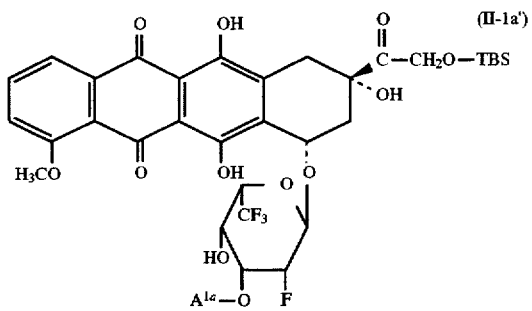

wherein TBS has the same meaning as defined above and $A^{1a}$ has the same meaning as that of $A^{1a}$ defined in the general formula (I-2a') hereinbefore; and further prolonging the reaction time for the above esterification reaction and thereby producing also a 14-O-TBS-7-O-|2,6-dideoxy-2,6, 6,6-tetrafluoro-4-O-(N-Boc-aminoalkanoyl)-α-L-talopyranosyl)adriamycinone having the general formula

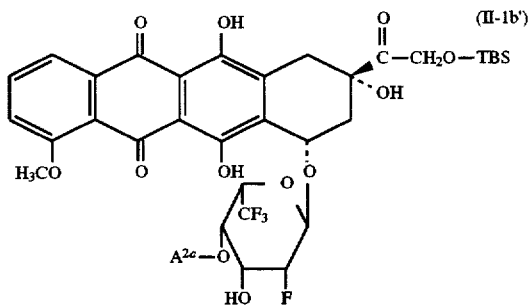

wherein TBS has the same meaning as defined above and $A^{2a}$ has the same meaning as that of $A^{1a}$ defined in the general formula (II-1a') hereinbefore; recovering a mixture of the compound of the formula (II-1a') and the compound of the formula (II-1b') from the reaction solution as formed in the above esterification reactions; then treating the recovered mixture with trifluoroacetic acid to effect simultaneous removal of the TBS group and Boc group from said two compounds; and subsequently recovering from the resulting reaction solution a mixture of the compound of the formula (II-1a) and the compound of the formula (II-1b) respectively in the form of their trifluoroacetate. Since mutual separation between the compound of the formula (II-1a) and the compound of the formula (II-1b) cannot be achieved by subjecting them to a chromatography under conventional conditions, it will need to devise a new separation method which can make such mutual separation of these compounds.

(H) The production of 7-O-(2,6-dideoxy-2,6,6,6-tetrafluoro-3,4-di-O-aminoalkanoyl-α-L-talopyranosyl) adriamycinone of the general formula (II-1c) according to the second aspect of this invention may be conducted by the following process.

Thus, the compound of the formula (II-1c) may be produced by such a process which comprises utilizing the compound of the formula (VI) as a starting compound; subjecting this starting compound to the esterification and the process of migration of the 3-O-aminoalkanoyl substituent of the esterification product in the same manner as in the process described in the foregoing item (G) so as to produce the compound of the formula (II-1a') and the compound of the formula (II-1b'); then recovering a mixture of these two compounds from the resulting reaction solution; reacting the recovered mixture of these two compound again with the active ester of the N-protected amino acid of the formula (III) or formula (IV) in pyridine; thereby producing a 14-O-TBS-7-O-|2,6-dideoxy-2,6,6,6-tetrafluoro-3,4-di-O-(N-Boc-aminoalkanoyl)-α-L-talopyranosyl]adriamycinone, and then treating the latter compound with trifluoroacetic acid to remove the TBS group and Boc group therefrom.

(I) The production of 7-O-(2,6-dideoxy-6,6,6-trifluoro-3-O- or -4-O- or -3,4-di-O-aminoalkanoyl-α-L-lyxo-hexopyranosyl)adriamycinone of the general formula (II-2a), the general formula (II-2b) of the general formula (II-2c) according to the second aspect of this invention may be conducted by the following process.

Thus, the compounds of the formula (II-2a), the formula (II-2b) and the formula (II-2c), respectively, may be produced by means of such a process which comprises utilizing as a starting compound 7-O-(2,6-dideoxy-6,6,6-trifluoro-α-L-lyxo-hexopyranosyl)adriamycinone of the formula (D) given hereinbefore (see the specification of the PCT application No. PCT/JP 95/00407; and Referential Example 4 shown hereinafter); tert-butyldimethylsilylating the primary 14-hydroxyl group of the starting compound of the formula (D) in the same manner as in the process described in the foregoing item (D) for the purpose of protecting said 14-hydroxyl group; thereby preparing a 14-O-tert-butyldimethylsilyl-7-O-(2,6-dideoxy-6,6,6-trifluoro-α-L-lyxo-hexopyranosyl)adriamycinone of the general formula

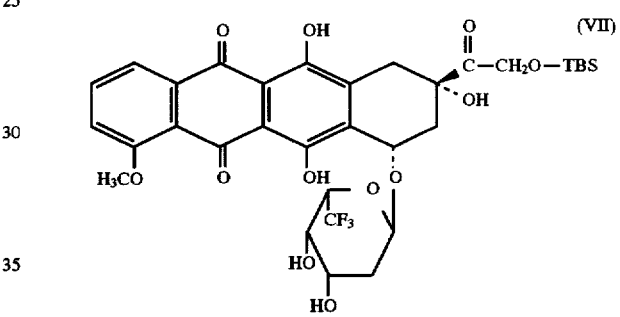

wherein TBS has the same meaning as defined hereinbefore; then esterifying the 3'-hydroxyl group of the adriamycinone derivative of the above formula (VII) with the active ester of the N-protected amino acid of the formula (III) or formula (IV) in the same manner as in the processes described in the foregoing item (G) and item (H); thereby producing a 14-O-TBS-7-O-[2,6-dideoxy-6,6,6-trifluoro-3-O-(N-Boc-aminoalkanoyl)-α-L-lyxo-hexopyranosyl]adriamycinone; further subjecting the latter compound to the process of migration of the aminoalkanoyl substituent from the 3'-position to the 4'-position of said compound in the same manner as in the processes described in the foregoing item (G) and item (H) to produce the corresponding 4-O-(N-Boc-aminoalkanoyl) derivative; then subjecting this 4-O-(N-Boc-aminoalkanoyl) derivative or the above 3-O-(N-Boc-aminoalkanoyl) derivative to a second esterification reaction with the active ester of the above-mentioned N-protected amino acid; thereby producing the corresponding 3,4-di-O-(N-Boc-aminoalkanoyl) derivative; and subjecting either one of the above-mentioned 3-O-(N-Boc-aminoalkanoyl) derivative, 4-O-(N-Boc-aminoalkanoyl) derivative and 3,4-di-O-(N-Boc-aminoalkanoyl) derivative obtained as the intermediate products to the deprotecting treatment with trifluoroacetic acid in the same manner as in the processes described in the foregoing item (G) and item (H) in order to eliminate the protecting groups (namely, the TBS group and Boc group) therefrom, whereby there can be produced the compounds of the formula (II-2a), the formula (II-2b) and the formula (II-2c), respectively, in the form of their trifluoroacetates.

Now, exemplary productions of the new compounds of the general formula (I) according to the first aspect of this invention, as well as of the new compounds of the general formula (II) according to the second aspect of this invention will be illustrated with reference to the following Examples to which this invention is not limited in any way.

EXAMPLE 1

(1) Preparation of 7-O-|3-O-(3-tert-butoxycarbonylaminopropionyl)-2,6-dideoxy-2-fluoro-α-L-talopyranosyl|daunomycinone (Compound 1) and 7-O-|4-O-(3-tert-butoxycarbonylaminopropionyl)-2,6-dideoxy-2-fluoro-α-L-talopyranosyl|daunomycinone (Compound 2)

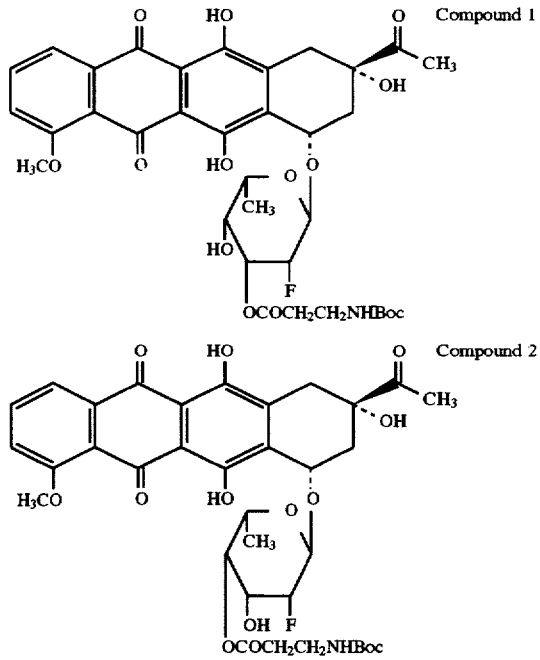

In the formulae above, Boc means tert-butoxycarbonyl group (the same is applied hereinafter).

7-O-(2,6-Dideoxy-2-fluoro-α-L-talopyranosyl) daunomycinone (see, The Journal of Antibiotics, 39, pp. 731–733; 1986) (110 mg) was dissolved in anhydrous pyridine (1.5 ml), and to the solution was added N-(3-tert-butoxycarbonylaminopropionyloxy)succinimide (155 mg). The resulting mixture was stirred at 60° C. for 3 hrs to conduct the esterification reaction.

The reaction solution so obtained was diluted with chloroform and the diluted solution was washed successively with a 20% aqueous potassium hydrogen sulfate solution, a saturated aqueous sodium hydrogen carbonate solution and water, then dried over anhydrous sodium sulfate and concentrated under a reduced pressure. The resulting residue was subjected to a silica gel column chromatography (developer: chloroform-acetone, 5:1) for the isolation and purification, to afford the titled Compound 1 where the 3'-hydroxyl group has been esterified with 3-tert-butoxycarbnylaminopropionyl group (89 mg, yield 62%).

|αa|$_D^{25}$+171° (c 0.1, chloroform)

$^1$H-NMR spectrum (in deutero-chloroform)
δ4.87 (1H, dt, H-3')
4.08 (3H, s, OCH$_3$)
2.41 (3H, s, Ac)
1.40 (9H, s, C(CH$_3$)$_3$)

Then, Compound 1 (38 mg) was dissolved in anhydrous acetonitrile (4 ml), and to the solution was added a silica gel ("Wako Gel C-200") (426 mg). The resulting mixture was stirred under reflux for 15 hrs to bring about the migration of the N-protected 3-aminopropionyl group of Compound 1. The reaction solution was filtered and the filtrate was concentrated under a reduced pressure to leave a residue-and the residue was reprecipitated from chloroform-hexane, affording a mixture of the titled Compounds 1 and 2 (37 mg).

$^1$H-NMR spectrum
2.42, 2.41 (3H in combination, each s, Ac)
1.43, 1.40 (9H in combination, each s, C(CH$_3$)$_3$)

(2) Preparation of 7-O-|3-O-(3-aminopropionyl)-2,6-dideoxy-2-fluoro-α-L-talopyranosyl|daunomycinone (Compound 3) and 7-O-|4-O-(3-aminopropionyl)-2,6-dideoxy-2-fluoro-α-L-talopyranosyl|daunomycinone (Compound 4)

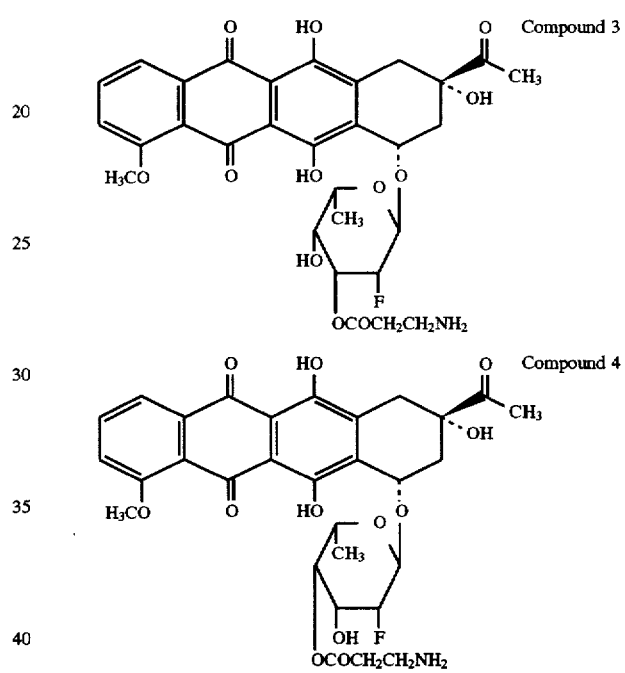

The mixture of Compounds 1 and 2 obtained in item (1) above (40 mg) was dissolved in aqueous 95% trifluoroacetic acid (0.5 ml) by adding the latter under ice-cooling, and the solution was stirred at room temperature for 30 minutes to effect the deprotection reaction for the removal of Boc group.

The resulting reaction solution was concentrated under a reduced pressure, toluene was added to the resulting residue and the mixture obtained was subjected repeatedly to the concentration procedure under a reduced pressure in the same manner as above for the removal of trifluoroacetic acid. The resulting residue was reprecipitated from methanol-ether, to afford a mixture of the titled Compounds 3 and 4 in the form of trifluoroacetates as a red solid (33 mg, yield 81%). The ratio of Compound 3 to 4 in the mixture was about 1:5 based on the $^{19}$F-NMR spectrum.

$^{19}$F-NMR spectrum (deutero-water, CFCl$_3$ as external standard)
δ–76.5 (3F, s, CF$_3$COOH)
–201.0 (0.17F, ddd, F-2' of Compound 3)
–203.4 (0.83F, ddd, F-2' of Compound 4)

EXAMPLE 2

(1) Preparation of 14-O-tert-butyldimethylsilyl-7-O-(2,6-dideoxy-2-fluoro-α-L-talopyranosyl)adriamycinone (Compound 5)

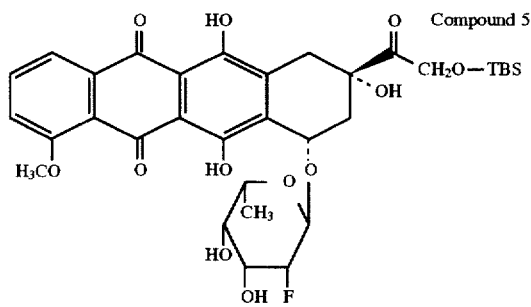

Compound 5

In the formula above, TBS means tert-butyldimethylsilyl group $Si(CH_3)_2C(CH_3)_3$ (the same is applied hereinafter).

7-O-(2,6-Dideoxy-2-fluoro-α-L-talopyranosyl) adriamycinone (see, The Journal of Antibiotics, 39, PP. 731–733; 1986) (128 mg) was dissolved in anhydrous N,N-dimethylformamide (DMF) (0.8 ml), and to the solution were added imidazole (43 mg) and tert-butylchlorodimethylsilane (35 mg). The resulting mixture was stirred at room temperature for 2 hrs.

The resulting reaction solution containing the titled Compound 5 thus produced was diluted with chloroform, washed successively with a 20% aqueous potassium hydrogen sulfate solution, a saturated aqueous sodium hydrogen carbonate solution and water, then dried over anhydrous sodium sulfate and concentrated under a reduced pressure. The resulting residue was purified by a silica gel column chromatography (developer: chloroform-acetone, 3:1), to afford the titled Compound 5 as a red solid (126 mg, yield 82%).

$[\alpha]_D^{25}+115°$ (c 0.1, chloroform)

$^1$H-NMR spectrum (deutero-chloroform)

δ4.84 (2H, s, H-14a, b)
4.10 (3H, s, $OCH_3$)
0.96 (9H, s, $SiC(CH_3)_3$)
0.15 (6H, s, $Si(CH_3)_2$)

$^{19}$F-NMR spectrum (deutero-chloroform-deutero-water, $CFCl_3$ as internal standard)
δ–201.1 (ddd)

(2) Preparation of 14-O-tert-butyldimethylsilyl-7-O-{3-O-[N-(tert-butoxycarbonyl)glycyl]-2,6-dideoxy-2-fluoro-α-L-talopyranosyl}adriamycinone (Compound 6a) and 14-O-tert-butyldimethylsilyl-7-O-{4-O-[N-(tert-butoxycarbonyl)glycyl]-2,6-dideoxy-2-fluoro-α-L-talopyranosyl}adriamycinone (Compound 7a)

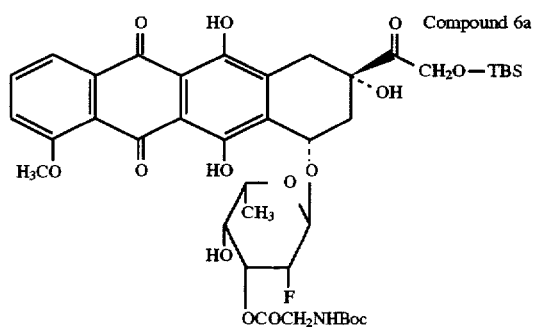

Compound 6a

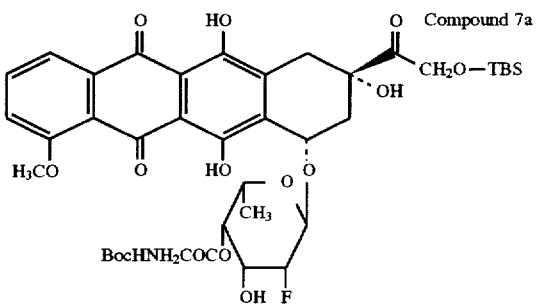

Compound 7a

Compound 5 obtained in item (1) above (260 mg) was dissolved in anhydrous pyridine (4 ml), and to the solution was then added N-|N-(tert-butoxycarbonyl)glycyloxy| succinimide (230 mg). The resulting mixture was stirred at room temperature for 2 hrs and then at 60° C. for 3 hrs to conduct the esterification.

The reaction solution, after adding water (0.05 ml) thereto, was stirred at room temperature for 5 hrs, diluted with chloroform, washed successively with a 20% potassium hydrogen sulfate solution, a saturated aqueous hydrogen carbonate solution and water, then dried over anhydrous sodium sulfate and concentrated under a reduced pressure. The resulting residue was purified by a silica gel column chromatography (developer: chloroform-acetone, 5:1), to afford a mixture of the titled Compounds 6a and 7a as a red solid (211 mg, yield 66%). The ratio of Compounds 6a to 7a was about 2.5:1 based on $^{19}$F-NMR spectrum, i.e. Compound 6a was the main product.

$^1$H-NMR spectrum (deutero-chloroform)

δ4.08 (3H, s, $OCH_3$)
1.46, 1.41 (9H in combination, each s, $C(CH_3)_3$ of Boc group)

$^{19}$F-NMR spectrum (deutero-chloroform, $CFCl_3$ as internal standard)

δ–198.3 (0.7F, ddt, F-2' of Compound 6a)
–203.0 (0.3, ddd, F-2' of Compound 7a)

Then, the mixture (58 mg) was dissolved in anhydrous acetonitrile (30 ml), and to the solution was added a silica gel (Wako Gel C-200) (600 mg) and the mixture was stirred under reflux for 15 hrs to bring about the migration of the N-protected glycyl group.

The reaction solution was filtered and the filtrate was concentrated under a reduced pressure to leave a residue and the residue was reprecipitated from chloroform-hexane to yield a mixture of the titled Compounds 6a and 7a (56 mg). The ratio of Compounds 6a to 7a was about 1:2 based on $^{19}$F-NMR spectrum, i.e. Compound 7a was the major product to Compound 6a.

(3) Preparation of 7-O-(2,6-dideoxy-2-fluoro-3-O-glycyl-α-L-talopyranosyl)adriamycinone (Compound 8a) and 7-O-(2,6-dideoxy-2-fluoro-4-O-glycyl-α-L-talopyranosyl) adriamycinone (Compound 9a)

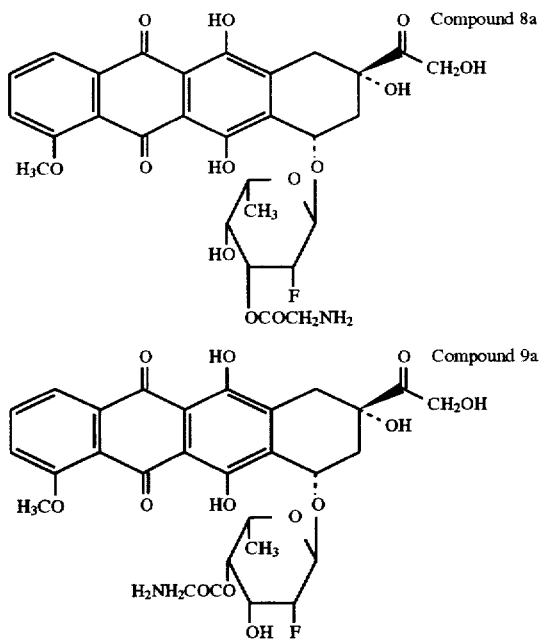

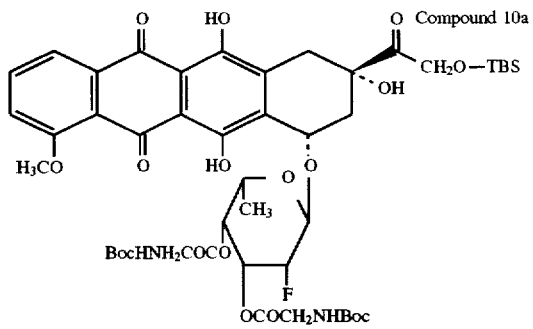

The mixture of Compounds 6a and 7a (about 1:2) obtained in item (2) above (15 mg) was dissolved in aqueous 95% trifluoroacetic acid (0.2 ml) with addition of the latter to the former under ice-cooling, and the solution was stirred at room temperature for 30 minutes to effect the elimination of the tert-butyldimethylsilyl group (TBS) and the tert-butoxycarbonyl group (Boc).

The reaction solution obtained was concentrated under a reduced pressure to leave a residue, to which toluene was added. The resulting mixture was concentrated under a reduced pressure; and the procedure was repeated until the trifluoroacetic acid was removed. The resulting residue was reprecipitated from methanol-ether, thus yielding a mixture of the titled Compounds 8a and 9a in the form of trifluoroacetates as a red solid (13 mg), (quantitatively). This mixture was well soluble in water. During the deprotection reaction, the migration was further occurred, and thus the ratio of Compounds 8a to 9a was about 1:4 based on $^{19}$F-NMR spectrum.

$^{19}$F-NMR spectrum (deutero-water CFCl$_3$ as external standard

δ–76.5 (3F, s, CF$_3$COOH)
–201.3 (0.2F, m, F of Compound 8a)
–203.6 (0.8F, m, F of Compound 9a)

Elemental analysis (for C$_{29}$H$_{30}$FNO$_{13}$·CF$_3$COOH·1.6H$_2$O) Calculated C, 48.84; H, 4.52; F, 9.97; N, 1.84% Found C, 48.66; H, 4.49; F, 10.23; N, 1.86%

EXAMPLE 3

(1) Preparation of 14-O-tert-butyldimethylsilyl-7-O-{3,4-di-O-[N-(tert-butoxycarbonyl)glycyl]-2,6-dideoxy-2-fluoro-α-L-talopyranosyl}adriamycinone (Compound 10a)

The mixture of Compounds 6a and 7a at the ratio of about 1:2 obtained in Example 2 (2) (12 mg) was dissolved in anhydrous pyridine (0.2 ml), and to the solution was added N-[N-(tert-butoxycarbonyl)glycyloxy]succinimide (12 mg). The mixture was stirred at 60° C. for 15 hrs to effect the esterification.

The resulting reaction solution was diluted with chloroform, washed, successively, with a 20% aqueous potassium hydrogen sulfate solution, a saturated aqueous sodium hydrogen carbonate solution and water, then dried over anhydrous sodium sulfate and concentrated under a reduced pressure. The residue obtained was subjected to a silica gel column chromatography two times (first developer: chloroform-acetone, 15:1; and second developer: dichloromethane-acetone, 10:1) to isolate and purify the desired product, affording the titled Compound 10a as a red solid (10 mg, yield 71%).

$^1$H-NMR spectrum (deutero-chloroform)
δ4.84 (2H, s, H-14a, b)
4.09 (3H, s, OCH$_3$)
1.46, 1.42 (each 9H, s, C(CH$_3$)$_3$ of Boc group)

$^{19}$F-NMR spectrum (deutero-chloroform, CFCl$_3$ as internal standard)
δ–200.9 (ddd)

(2) Preparation of 7-O-(2,6-dideoxy-2-fluoro-3,4-di-O-glycyl-α-L-talopyranosyl)adriamycinone (Compound 11a)

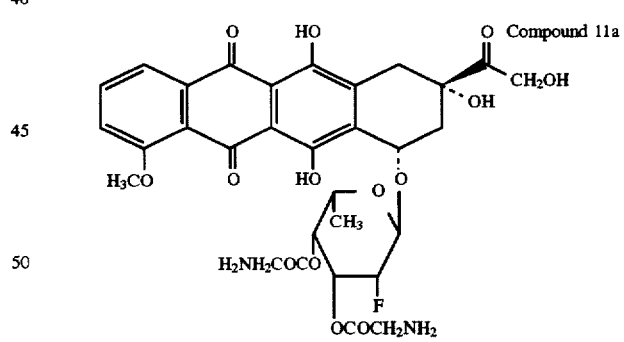

To Compound 10a (24 mg) obtained in item (1) above was added aqueous trifluoroacetic acid (0.36 ml) under ice-cooling, and the solution obtained was stirred at room temperature for 30 minutes to eliminate the TBS group and Boc group.

The reaction solution was concentrated under a reduced pressure to leave a residue. The residue was subjected to such treatment repeatedly that toluene was added to the residue and the resulting mixture was concentrated under a reduced pressure for the purpose of removing the trifluoroacetic acid. The resulting residue was reprecipitated from methanol-ether, thus affording the titled compound in the form of trifluoroacetate salt as a red solid (20.8 mg, yield 95%).

¹H-NMR spectrum (deutero-methanol)
δ5.56 (1H, d, H-1')
5.36 (1H, dt, H-3')
5.35 (1H, m, H-4')
4.04 (3H, s, OCH₃)
¹⁹F-NMR (deutero-methanol, CFCl₃ as internal standard)
δ–75.3 (6F, s, CF₃COOH×2)
–200.7 (1F, ddd, F-2')

EXAMPLE 4

(1) Preparation of 14-O-tert-butyldimethylsilyl-7-O-{3-O-|N-(tert-butoxycarbonyl)-L-alanyl|-2,6-dideoxy-2-fluoro-α-L-talopyranosyl}adriamycinone (Compound 6b) and 14-O-tert-butyldimethylsilyl-7-O-{4-O-|N-(tert-butoxycarbonyl)-L-alanyl|-2,6-dideoxy-2-fluoro-α-L-talopyranosyl}adriamycinone (Compound 7b)

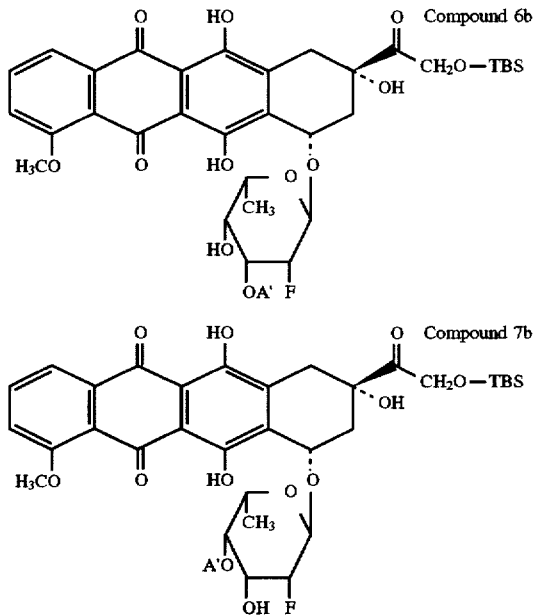

In the formula above, A' means N-Boc-L-alanyl group. Compound 5 (22 mg) obtained in Example 2 (1) was dissolved in anhydrous pyridine (0.3 ml), and to the solution was added N-|N-(tert-butoxycarbonyl)-L-alanyloxy| succinimide (30 mg). The resulting mixture was stirred at 60° C. for 3 hrs. The reaction solution was subjected to a post-treatment in the same manner as in Example 2 (2) and the residue obtained was purified by a silica gel column chromatography two times (first developer: chloroform-acetone, 3:1; and second developer: toluene-ethyl acetate, 2:1), to afford a mixture of the titled Compounds 6b and 7b as a red solid (23 mg, yield 81%). A ¹⁹F-NMR spectrum shows the ratio of Compounds 6b to 7b to be about 1:0.6, Compound 6b being the main product.

¹⁹F-NMR spectrum (deutro-chloroform, CFCl₃ as internal standard)
δ–198.2 (0.63F, ddt, F-2' of Compound 6b)
–203.6 (0.37F, br, F-2' of Compound 7b)

The mixture (8.5 mg) was then dissolved in anhydrous acetonitrile (1.7 ml), and to the solution was added a silica gel (85 mg). The resultant mixture was stirred under reflux for 17 hrs. The reaction solution was post-treated in the same manner as in Example 2 (2), thus affording a mixture of the titled Compounds 6b and 7b (8 mg). A ¹⁹F-NMR spectrum shows the ratio of Compounds 6b to 7b to be about 1:4, Compound 7b being the main product.

(2) Preparation of 7-O-(3-O-L-alanyl-2,6-dideoxy-2-fluoro-α-L-talopyranosyl)adriamycinone (Compound 8b) and 7-O-(4-O-L-alanyl-2,6-dideoxy-2-fluoro-α-L-talopyranosyl)adriamycinone (Compound 9b)

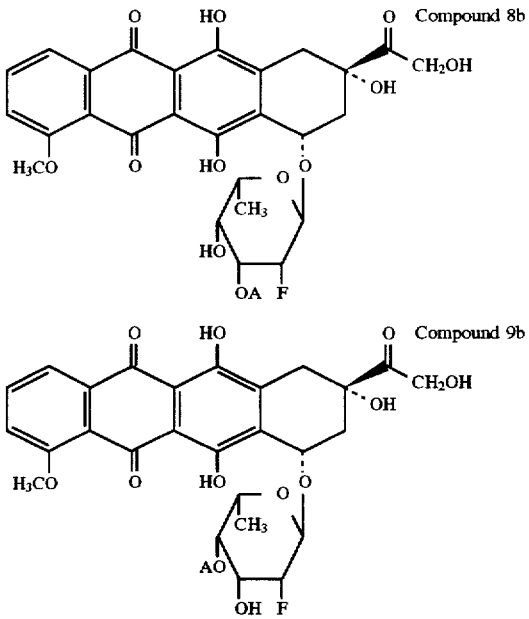

In the formulae above, A means L-alanyl group.

To the mixture of Compounds 6b and 7b (about 1:4 ratio) (20 mg), which was obtained in item (1) above, trifluoroacetic acid was added under ice-cooling, and the mixture so obtained was stirred at room temperature for 30 minutes. The reaction solution was post-treated in the same manner as in Example 2 (3), to afford a mixture of Compounds 8b and 9b (as trifluoroacetates) as a red solid (17 mg, yield 96%). The ratio of Compounds 8b to 9b in the mixture was about 1:5.

¹H-NMR spectrum (deutero-methanol)
δ1.64 (2.5H, d, CH₃ of alanyl group of Compound 9b)
1.57 (0.5H, d, CH₃ of alanyl group of Compound 8b)
¹⁹F-NMR spectrum (deutero-methanol, CFCl₃ as internal standard)
δ–75.3 (3F, s, CF₃COOH)
–199.5 (0.17F, ddd, F-2' of Compound 8b)
–202.5 (0.83F, ddd, F-2' of Compound 9b)

EXAMPLE 5

(1) Preparation of 14-O-tert-butyldimethylsilyl-7-O-{3,4-di-O-|N-(tert-butoxycarbonyl)-L-alanyl|-2,6-dideoxy-2-fluoro-α-L-talopyranosyl}adriamycinone (Compound 10b)

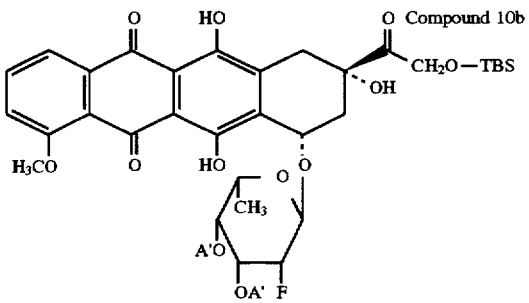

In the formula above, A' means N-Boc-L-alanyl group.

The mixture of Compounds 6b and 7b at the ratio of about 1:4 (56 mg) which was obtained in Example 4 (1) was dissolved in anhydrous pyridine (0.8 ml). To the solution was added N-|N-(tert-butoxycarbonyl)-L-alanyloxy| sccinimide (61 mg), and the resulting mixture was stirred at 60° C. for 16 hrs. The reaction solution, after water (0.1 ml) was added thereto, was stirred at room temperature for 3 hrs and then post-treated as in Example 3 (1) to leave a residue, which was purified by a silica gel column chromatography (developer: benzene-acetone, 6:1), to afford the titled Compound 10b as a red solid (20 mg, yield 29%). The mixture of the starting Compounds 6b and 7b was recovered in a yield of 34% thereof.

$^1$H-NMR spectrum (deutero-chloroform)

δ4.09 (3H, s, OCH$_3$)

1.45, 1.40 (18H in combination, each s, C(CH$_3$)$_3$) of Boc group)

$^{19}$F-NMR spectrum (deutero-chloroform, CFCl$_3$ as internal standard)

δ–200.5 (br)

(2) Preparation of 7-O-(3,4-di-O-L-alanyl-2,6-dideoxy-2-fluoro-α-L-talopyranosyl)adriamycinone (Compound 11b)

In the formula above, A means L-alanyl group.

To Compound 10b (13 mg) obtained in item (1) above was added aqueous trifluoroacetic acid (0.2 ml) under ice-cooling and the solution obtained was stirred for 30 minutes. The reaction solution was post-treated as in Example 3 (2), affording the titled Compound 11b (as trifluoroacetate) as a red solid (11 mg, yield 93%).

$^1$H-NMR spectrum (deutero-methanol)

δ1.66, 1.49 (each 3H, each d, CH$_3$ of L-alanyl group)

$^{19}$F-NMR spectrum (deutero-methanol, CFCl$_3$ as internal standard)

δ–75.3 (6F, s, CF$_3$COOH×2)

–200.9 (1F, ddd, F-2')

EXAMPLE 6

(1) Preparation of 14-O-tert-butyldimethylsilyl-7-O-{3-O-[N-(tert-butoxycarbonyl)-L-phenylalanyl]-2,6-dideoxy-2-fluoro-α-L-talopyranosyl}adriamycinone (Compound 6c) and 14-O-tert-butyldimethylsilyl-7-O-{4-O-[N-(tert-butoxycarbonyl)-L-phenylalanyl]-2,6-dideoxy-2-fluoro-α-L-talopyranosyl}adriamycinone (Compound 7c)

In the formulae above, A' represents N-Boc-L-phenylalanyl group.

Compound 5 (25 mg) obtained in Example 2 (1) was dissolved in anhydrous pyridine (0.4 ml), and to the solution was added N-[N-(tert-butoxycarbonyl)-L-phenylalanyloxy] succinimide (49 mg), and the mixture was stirred at 60° C. for 3 hrs.

The reaction solution was post-treated as in Example 2 (2) and the resulting solid was purified by a silica gel column chromatography two times (first developer: chloroform-acetone, 3:1; and second developer: toluene-ethyl acetate, 2:1), thus yielding the titled Compound 6c as a red solid (31 mg, yield 88%).

$^1$H-NMR spectrum (deutero-chloroform)

δ4.09 (OCH$_3$)

1.41, 1.37 (9H in combination, each s, C(CH$_3$)$_3$ of Boc group)

$^{19}$F-NMR spectrum (deutero-chloroform, CFCl$_3$ as internal standard)

δ–198.0 (ddt)

Compound 6c (28 mg) was then dissolved in anhydrous acetonitrile (10 ml), and to the solution was added a silica gel (Wako Gel C-200) (290 mg). The mixture was refluxed for 40 hrs to effect the reaction. The reaction solution was post-treated as in Example 2 (2), thus affording a mixture of the titled Compounds 6c and 7c as a red solid (24 mg). The ratio of Compounds 6c to 7c in the mixture was about 1:2.5.

$^{19}$F-NMR spectrum (deutero-chloroform, CFCl$_3$ as internal standard)

δ–198.0 (0.3F, ddd, F-2' of Compound 6c)

–203.4 (0.7F, ddd, F-2' of Compound 7c)

(2) Preparation of 7-O-(2,6-dideoxy-2-fluoro-3-O-L-phenylalanyl-α-L-talopyranosyl)adriamycinone (Compound 8c) and 7-O-(2,6-dideoxy-2-fluoro-4-O-L-phenylalanyl-α-L-talopyranosyl)adriamycinone (Compound 9c)

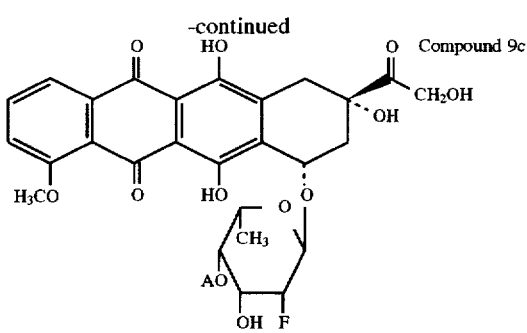

Compound 9c

In the formulae above, A represents L-phenylalanyl group.

To the mixture of Compounds 6c and 7c at the ratio of about 1:2.5 (19 mg) which was obtained in item (1) above was added aqueous trifluoroacetic acid under ice-cooling to give a solution, which was then stirred at room temperature for 30 minutes. The reaction solution was post-treated as in Example 2 (3), thus affording a mixture of the titled Compounds 8c and 9c (as trifluoroacetates) as a red solid (16 mg, yield 86%). The ratio of Compounds 8c to 9c was about 1:4.5.

$^{19}$F-NMR spectrum (deutero-methanol, CFCl$_3$ as internal standard)

δ–75.3 (3F, s, CF$_3$COOH)
–199.3 (0.18F, ddd, F-2' of Compound 8c)
–202.2 (0.82F, ddd, F-2' of Compound 9c)

EXAMPLE 7

(1) Preparation of 14-O-tert-butyldimethylsilyl-7-O-{3,4-di-O-[N-(tert-butoxycarbonyl)-L-phenylalanyl]-2,6-dideoxy-2-fluoro-α-L-talopyranosyl}adriamycinone (Compound 10c)

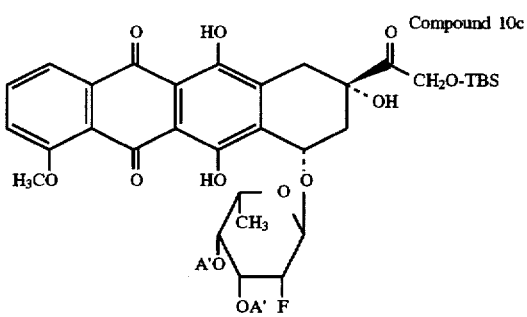

Compound 10c

In the formula above, A' represents N-Boc-L-phenylalanyl group.

The mixture of Compounds 6c and 7c at the ratio of about 1:2.5 (30 mg) which was obtained in Example 6 (1) was dissolved in anhydrous pyridine (0.5 ml), and to the solution was added N-[N-(tert-butoxycarbonyl)-L-phenylalanyloxy] succinimide (33 mg). The resulting mixture was stirred at 60° C. for 15 hrs. The reaction solution, after water (0.05 ml) was added thereto, was stirred at room temperature for 16 hrs and then post-treated as in Example 3 (1) to leave a residue. The residue was subjected to a silica gel column chromatography (developer: chloroform-acetone, 15:1) for isolation and purification of the desired product, affording the titled Compound 10c as a red solid (32 mg, yield 85%)

$^1$H-NMR spectrum (deutero-chloroform)
δ4.09 (3H, s, OCH$_3$)
1.35, 1.33 (18H in combination, each s, C(CH$_3$)$_3$ of Boc group)

$^{19}$F-NMR spectrum (deutero-chloroform, CFCl$_3$ as internal standard)

δ–201.1 (ddd)

(2) Preparation of 7-O-(2,6-dideoxy-2-fluoro-3,4-di-O-L-phenylalanyl-α-L-talopyranosyl)adriamycinone Compound 11c)

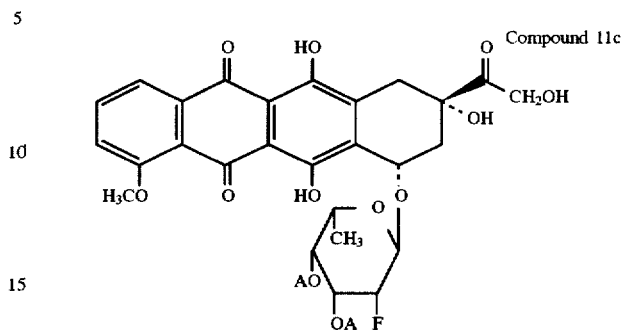

Compound 11c

In the formula above, A represents L-phenylalanyl group.

To Compound 10c (10 mg) obtained in item (1) above was added aqueous trifluoroacetic acid (0.15 ml) under ice-cooling, and the solution was stirred at room temperature for 30 minutes. The reaction solution was post-treated as in Example 3 (2) and the residue obtained was reprecipitated from methanol-isopropylether, thus affording the titled Compound 11c (as trifluoroacetate) as a red solid (6 mg, yield 67%).

$^1$H-NMR spectrum (deutero-methanol)
δ–7.3 (10H, m, Ph×2)
4.03 (3H, br s, OCH$_3$)

$^{19}$F-NMR spectrum (deutero-methanol, CFCl$_3$ as internal standard)

δ–75.2 (6F, s, CF$_3$COOH×2)
–200.4 (1F, br dd, F-2')

EXAMPLE 8

(1) Preparation of 14-O-tert-butyldimethylsilyl-7-O-{3-O-[N-tert-butoxycarbonyl)-L-valyl]-2,6-dideoxy-2-fluoro-α-L-talopyranosyl}adriamycinone (Compound 6d) and 14-O-tert-butyldimethylsilyl-7-O-{4-O-[N-tert-butoxycarbonyl)-L-valyl]-2,6-dideoxy-2-fluoro-α-L-talopyranosyl}adriamycinone (Compound 7d)

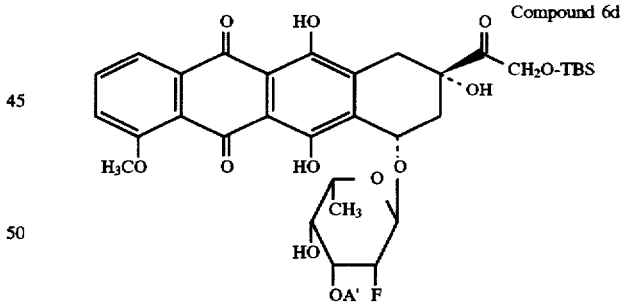

Compound 6d

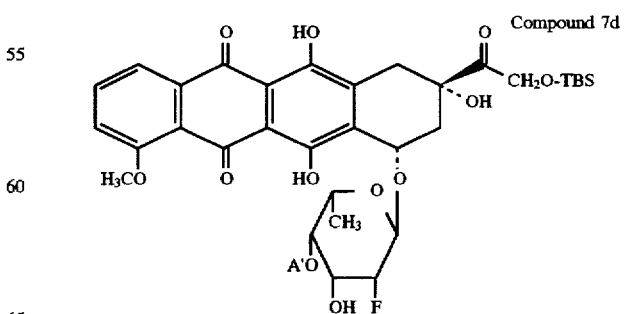

Compound 7d

In the formulae above, A' represents N-Boc-L-valyl group.

Compound 5 (37 mg) obtained in Example 2 (1) was dissolved in anhydrous pyridine (0.6 ml), and to the solution was added N-|N-(tert-butoxycarbonyl)-L-valyloxy| succinimide (50 mg). The resulting mixture was stirred at 60° C. for 3 hrs. The reaction solution was post-treated as in Example 3 (2) and the residue obtained was purified by a silica gel column chromatography two times (first developer: chloroform-acetone, 10:1; and second developer: toluene-ethyl acetate, 2:1), to afford one of the titled Compounds, 6d, as a red solid (46 mg, yield 96%).

¹H-NMR spectrum (deutero-chloroform)
δ4.09 (3H, s, OCH₃)
1.40 (9H, s, C(CH₃)₃ of Boc group)
¹⁹F-NMR spectrum (deutero-chloroform, CFCl₃ as internal standard)
δ-197.9 (ddt)

Then, Compound 6d (19 mg) was dissolved in anhydrous acetonitrile (5 ml), to which was added a silica gel (190 mg), and the resulting mixture was stirred under reflux for 16 hrs. The reaction solution was post-treated as in Example 3 (2), yielding a mixture of the titled Compounds 6d and 7d (18 mg). The ratio of Compounds 6d to 7d in the mixture obtained was about 2:1 as determined by ¹⁹F-NMR spectrum.

(2) Preparation of 7-O-(2,6-dideoxy-2-fluoro-3-O-L-valyl-α-L-talopyranosyl)adriamycinone (Compound 8d) and 7-O-(2,6-dideoxy-2-fluoro-4-O-L-valyl-α-L-talopyranosyl) adriamycinone (Compound 9d)

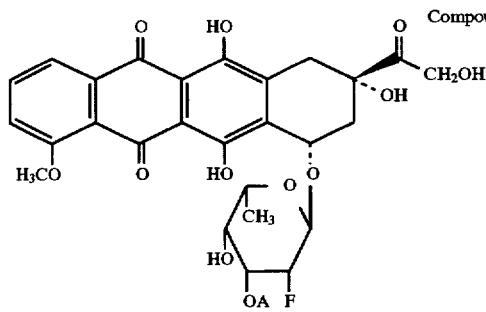
Compound 8d

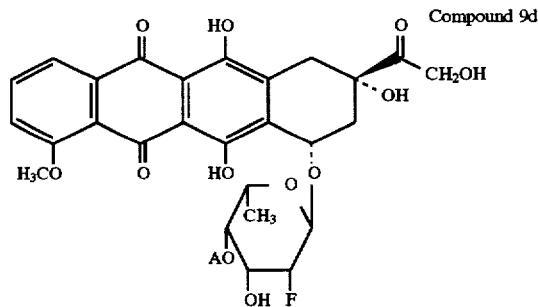
Compound 9d

In the formulae above, A represents L-valyl group.

To the mixture of Compounds 6d and 7d (about 2:1) (26 mg) obtained in item (1) above was added aqueous trifluoroacetic acid (0.4 ml) under ice-cooling and the solution was stirred at room temperature for 30 minutes. The reaction solution was post-treated as in Example 2 (3) and the residue obtained was dissolved in water, washed with chloroform and then concentrated under a reduced pressure. The resulting residue was reprecipitated from methanol-ether, to afford a mixture of the titled compounds 8d and 9d (as trifluoroacetates) as a red solid (11.5 mg, yield 50%). The ratio of Compounds 8d to 9d was 1:1.

¹⁹F-NMR spectrum (deutero-methanol, CFCl₃ as internal standard)

δ-75.3 (3F, s, CF₃COOH)
-199.1 (0.5F, ddd, F-2' of Compound 8d)
-202.3 (0.5F, ddd, F-2' of Compound 9d)

EXAMPLE 9

(1) Preparation of 14-O-tert-butyldimethylsilyl-7-O-{3,4-di-O-|N-(tert-butoxycarbonyl)-L-valyl|-2,6-dideoxy-2-fluoro-α-L-talopyranosyl}adriamycinone (Compound 10d)

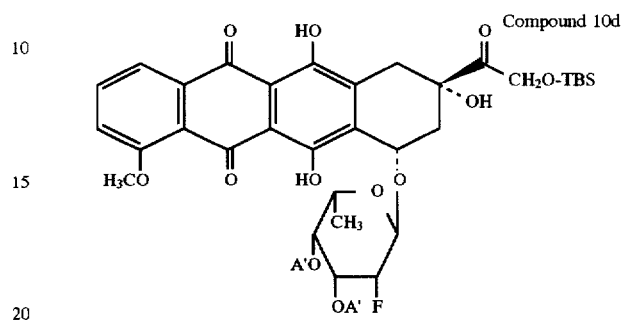
Compound 10d

In the formula above, A' represents N-Boc-L-valyl group.

The mixture of Compounds 6d and 7d (about 2:1) (26 mg) as obtained in Example 8 (1) was dissolved in anhydrous pyridine (0.4 ml), and to the solution was added an active ester, N-[N-(tert-butoxycarbonyl)-L-valyloxy|succinimide (36 mg). The mixture so obtained was stirred at 60° C. for 15 hrs. Then, a further amount (27 mg) of the active ester was added and the stirring was continued for further 16 hrs. The reaction solution was post-treated as in Example 7 (1) and the residue obtained was purified by a silica gel column chromatography two times (first developer: toluene-ethyl acetate, 20:1; and second developer: chloroform-acetone, 15:1), affording the titled compound as a reddish orange solid (5.7 mg, yield 18%).

¹H-NMR spectrum (deutero-chloroform)
δ4.09 (3H, s, OCH₃)
1.47, 1.42 (18H in combination, each s, C(CH₃)₃ of Boc group)
¹⁹F-NMR spectrum (deutero-chloroform, CFCl₃ as internal standard)
δ-201.5 (br ddd)

(2) Preparation of 7-O-(2,6-dideoxy-2-fluoro-3,4-di-O-L-valyl-α-L-talopyranosyl)adriamycinone (Compound 11d)

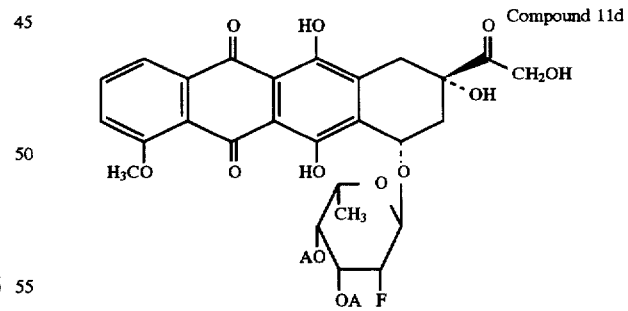
Compound 11d

In the formula above, A represents L-valyl group.

To Compound 10d (4.5 mg) obtained in item (1) above was added aqueous 95% trifluoroacetic acid (0.02 ml) under ice-cooling and the solution was stirred at room temperature for 30 minutes. The reaction solution was post-treated as in Example 3 (2) and the residue obtained was dissolved in water. The solution was washed with chloroform and then concentrated under a reduced pressure. The residue so obtained was reprecipitated from methanol-ether, affording the titled Compound 11d (as trifluoroacetate) as a red solid (2.2 mg, yield 54%).

¹H-NMR spectrum (deutero-methanol)
δ4.05 (3H, s, OCH₃)
1.29, 1.17, 1.13, 1.05, 1.00 (each 3H, each d, CH₃ of L-valyl group and CH₃-5')
¹⁹F-NMR spectrum (deutero-methanol, CFCl₃ as internal standard)
δ−76.9 (6F, s, CF₃COOH×2)
−202.4 (1F, ddd, F-2')

EXAMPLE 10

(1) Preparation of 14-O-tert-butyldimethylsilyl-7-O-{3-O-[N-(tert-butoxycarbonyl)-L-leucyl]-2,6-dideoxy-2-fluoro-α-L-talopyranosyl}adriamycinone (Compound 6e) and 14-O-tert-butyldimethylsilyl-7-O-{4-O-[N-(tert-butoxycarbonyl)-L-leucyl]-2,6-dideoxy-2-fluoro-α-L-talopyranosyl}adriamycinone (Compound 7e)

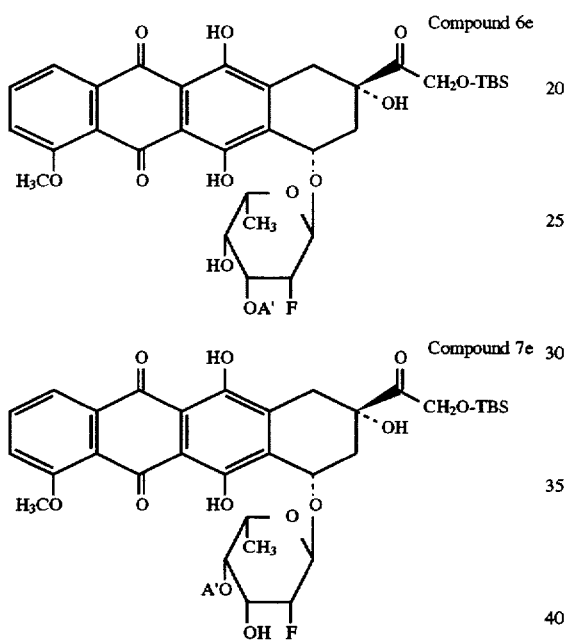

In the formulae above, A' represents N-Boc-L-leucyl group.

Compound 5 (31 mg) obtained in Example 2 (1) was dissolved in anhydrous pyridine (0.5 ml), and to the solution was added N-[N-(tert-butoxycarbonyl)-L-leucyloxyl]succinimide (38 mg). The mixture obtained was stirred at room temperature for 15 hrs, and then at 60° C. for 3 hrs. The reaction solution was post-treated as in Example 2 (2) and the residue obtained was purified by a silica gel column chromatography (developer: chloroform-acetone, 15:1) , to afford a mixture of the titled Compounds 6e and 7e as a red solid (19 mg, yield 46%). Also, 43% of the starting material used was recovered. The ratio of Compounds 6e to 7e in the mixture was about 3.5:1 as determined by ¹⁹F-NMR spectrum.

¹⁹F-nmr spectrum (deutero-chloroform, CFCl₃ as internal standard)
δ−198.2 (0.78F, ddt, F-2' of Compound 6e)
−203.8 (0.22F, ddt, F-2' of Compound 7e)

Then, the mixture obtained as above (18 mg) was dissolved in anhydrous acetonitrile (3.5 ml), to which was added a silica gel (180 mg). The resultant mixture was stirred under reflux for 45 hrs. The reaction solution was post-treated as in Example 2 (2), thus affording a mixture of the titled Compounds 6e and 7e (17.5 mg). The ratio of Compounds 6e to 7e was about 1:2.2.

(2) Preparation of 7-O-(2,6-dideoxy-2-fluoro-3-O-L-leucyl-α-L-talopyranosyl)adriamycinone (Compound 8e) and 7-O-(2,6-dideoxy-2-fluoro-4-O-L-leucyl-α-L-talopyranosyl)adriamycinone (Compound 9e)

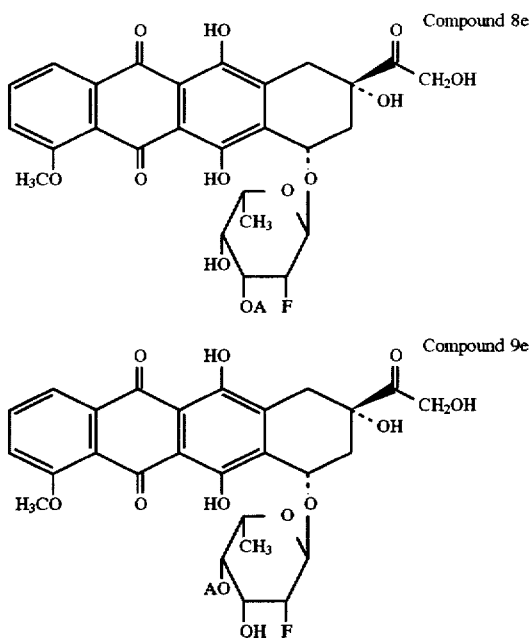

In the formulae above, A represents L-leucyl group.

To the mixture of Compounds 6e and 7e (17 mg) obtained in item in (1) above was added trifluoroacetic acid (0.25 ml) under ice cooling and the solution was stirred at room temperature for 30 minutes. The reaction solution was post-treated as in Example 8 (2), affording a mixture of the titled Compounds 8e and 9e (as trifluoroacetates) as a red solid (8.5 mg, yield 56%). The ratio of Compounds 8e to 9e was about 1:6.5.

¹⁹F-NMR spectrum (deutero-methanol, CFCl₃ as internal standard)
δ−75.3 (3H, s, CF₃COOH)
−199.5 (0.13F, br, F-2' of Compound 8e)
−202.4 (0.87F, ddd, F-2' of Compound 9e)

EXAMPLE 11

Preparation of 14-O-tert-butyldimethylsilyl-7-O-{3,4-di-O-[N-(tert-butoxycarbonyl)-L-leucyl]-2,6-dideoxy-2-fluoro-α-L-talopyranosyl}adriamycinone (Compound 10e)

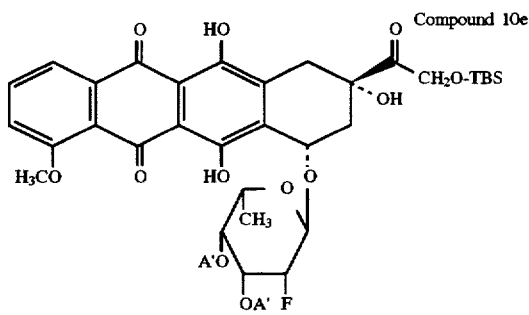

In the formula above, A' represents N-Boc-L-leucyl group.

The mixture of Compounds 6e and 7e (about 1:2.2) (17.5 mg) as obtained in Example 10 (1) was dissolved in anhydrous pyridine (0.25 ml), and to the solution was added an active ester, N-[N-(tert-butoxycarbonyl)-L-leucyloxy] sccinimide, (17.5 mg). The mixture obtained was stirred at 60° C. for 3 hrs. Then, a further amount (15 mg) of the active ester was added to the mixture and the said mixture was stirred at 60° C. for 15 hrs. Water (0.05 ml) was added to the reaction solution, which was then stirred at room temperature for 11 hrs and then post-treated as in Example 3 (1). The residue obtained was purified by a silica gel column chromatography two times (first developer: chloroform-acetone, 20:1; and second developer: toluene-ethyl acetate, 20:1), to afford the titled Compound 10e as a reddish orange solid (8.5 mg, yield 39%).

$^{19}$F-NMR spectrum (deutero-chloroform, CFCl$_3$ as internal standard)

δ–202.0 (br)

(2) Preparation of 7-O-(2,6-dideoxy-2-fluoro-3,4-di-O-L-leucyl-α-L-talopyranosyl)adriamycinone (Compound 11e)

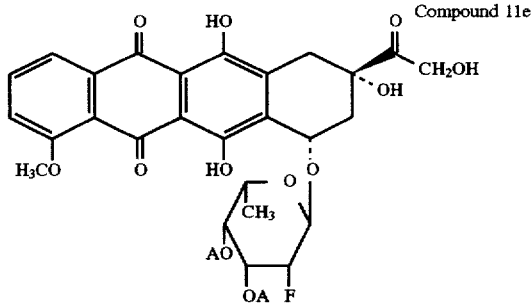

Compound 11e

In the formula above, A represents L-leucyl group.

To Compound 10e (8.5 mg) obtained in item (1) above was added aqueous trifluoroacetic acid (0.12 ml) under ice-cooling, and the resulting solution was stirred at room temperature for 30 minutes. The reaction solution was post-treated as in Example 3 (2), affording the titled Compound 11e (as trifluoroacetate) as a red solid (6.4 mg, yield 83%).

$^1$H-NMR spectrum (deutero-methanol)

δ5.38 (1H, br, H-4')

5.36 (1H, dt, H-3')

4.03 (3H, s, OCH$_3$)

$^{19}$F-NMR spectrum (deutero-metanol, CFCl$_3$ as internal standard)

δ–75.2 (6F, s, CF$_3$COOH×2)

–200.8 (1H, ddd, F-2')

EXAMPLE 12

(1) Preparation of 14-O-tert-butyldimethylsilyl-7-O-(2,6-dideoxy-2,6,6,6-tetrafluoro-α-L-talopyranosyl) adriamycinone (Compound 12)

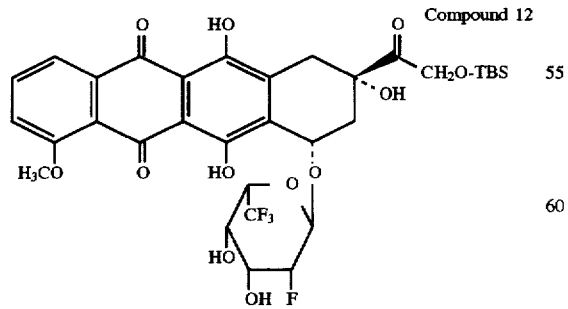

Compound 12

7-O-(2,6-Dideoxy-2,6,6,6-tetrafluoro-α-L-talopyranosyl) adriamycinone [the compound of formula (C-b) given hereinbefore] (129 mg) was dissolved in anhydrous N,N-dimethylformamide (DMF) (0.8 ml), and to the solution were added imidazole (39 mg) and tert-butylchlorodimethylsilane (32 mg). The resulting mixture was stirred at room temperature for 2 hrs to effect the tert-butyldimethylsilylation on the 14-hydroxyl group of compound of formula (C-b)

The reaction solution so obtained was diluted with chloroform, washed successively with a 20% aqueous potassium hydrogen sulfate solution, a saturated aqueous sodium hydrogen carbonate solution and water, then dried over anhydrous sodium sulfate and concentrated under a reduced pressure. The residue obtained was purified by a shilica gel column chromatography (developer: chloroform-acetone, 4:1), giving the titled compound 12 whose 14-hydroxyl group was protected with TBS group, as a red solid (125 mg, yield 82%)

$^1$H-NMR spectrum (deutero-chloroform)

δ4.09 (3H, s, OCH$_3$)

0.95 (9H, s, SiC(CH$_3$)$_3$)

0.16 (6H, s, Si(CH$_3$)$_2$)

$^{19}$F-NMR spectrum (deutero-chloroform, CFCl$_3$ as internal standard)

δ–71.8 (3F, d, CF$_3$)

–200.5 (1F, ddd, F-2')

(2) Preparation of 14-O-tert-butyldimethylsilyl-7-O-{3-O-[N-(tert-butoxycarbonyl)glycyl]-2,6-dideoxy-2,6,6,6-tetrafluoro-α-L-talopyranosyl}adriamycinone (Compound 13); and 14-O-tert-butyldimethylsilyl-7-O-{4-O-[N-(tert-butoxycarbonyl)glycyl]-2,6-dideoxy-2,6,6,6-tetrafluoro-α-L-talopyranosyl}adriamycinone (Compound 14)

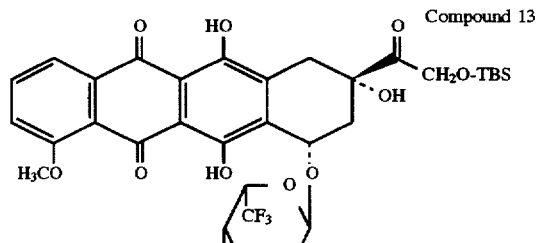

Compound 13

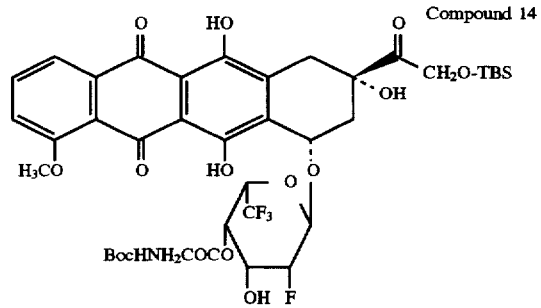

Compound 14

Compound 12 (125 mg) obtained in item (1) above was dissolved in anhydrous pyridine (1.8 ml), and to the solution was added an active ester of N-Boc-glycine, N-[N-(tert-butoxycarbonyl)glycyloxy]succinimide (106 mg). The resulting mixture was stirred at 60° C. for 2 hrs to effect the esterification reaction.

The resultant reaction solution, after adding a small amount of water, was stirred for 1 hour, diluted with chloroform, washed successively with a 20% aqueous potassium hydrogen sulfate solution, a saturated aqueous sodium hydrogen carbonate solution and water, then dried over anhydrous sodium sulfate and concentrated under a reduced pressure. The residue obtained was purified by a silica gel column chromatography (developer: chloroform-acetone, 6:1), to yield the titled Compound 13 which has the 3'-hydroxyl group esterified with tert-butoxycabonyl-glycyl group, as a red solid (80 mg, yield 53%).

The next step was to bring about the migration of the N-(tert-butoxycarbonyl)glycyl group at the 3'-position of Compound 13 to the 4'-position. That is, the red sloid of Compound 13 above was dissolved in anhydrous acetonitrile (4 ml), to the solution was added a silica gel (Wako Gel C-200) (800 mg). The mixture was refluxed for 18 hrs. The reaction solution was filtered and the filtrate was concentrated under a reduced pressure. The resulting residue was reprecipitated from chloroform-hexane to give a red solid (76 mg). The solid is a mixture of the titled Compound 14 with Compound 13, i.e. 3'-O-protected glycyl ester (2:1).

¹H-NMR spectrum (deutero-chloroform)
δ1.45, 1.41 (9H in combination, each s, C(CH₃)₃ of Boc group)

(3) Preparation of 7-O-(2,6-dideoxy-2,6,6,6-tetrafluoro-4-O-glycyl-α-L-talopyranosyl)adriamycinone (Compound 16) and 7-O-(2,6-dideoxy-2,6,6,6-tetrafluoro-3-O-glycyl-α-L-talopyranosyl)adriamycinone (Compound 15)

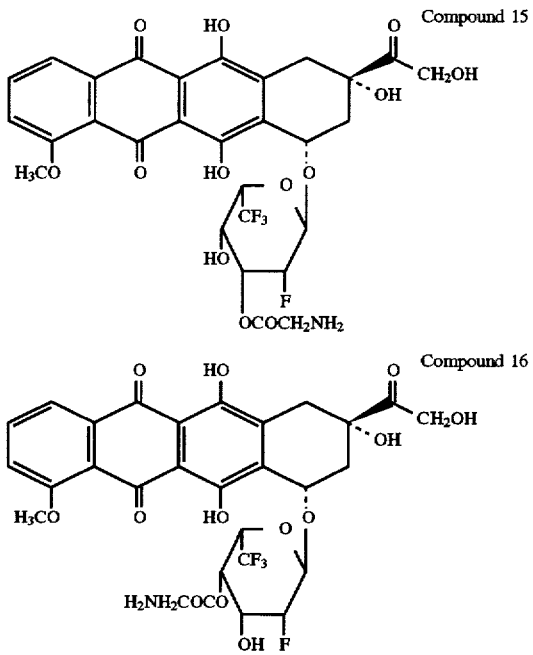

The mixture comprising Compounds 13 and 14 (76 mg) obtained in item (2) above was dissolved in aqueous trifluoroacetic acid (1 ml), and the solution was allowed to stand at room temperature for 30 minutes to conduct the reaction (for elimination of Boc group and TBS group). The reaction solution so obtained was concentrated under a reduced pressure and the residue obtained was reprecipitated from methanol-ether. The titled Compounds 15 and 16 in the form of trifluoroacetates were obtained as a mixture of them (58 mg, yield 87%).

¹H-NMR spectrum (heavy water)
δ5.36 (0.8H, br s, H-4' of 4'-O-glycyl derivative)
5.19 (0.2H, br d, H-3' of 3'-O-glycyl derivative)

EXAMPLE 13

(1) Preparation of 14-O-tert-butyldimethylsilyl-7-O-{3,4-di-O-|N-(tert-butoxycarbonyl)glycyl|-2,6-dideoxy-2,6,6,6-tetrafluoro-α-L-talopyranosyl}adriamycinone (Compound 17)

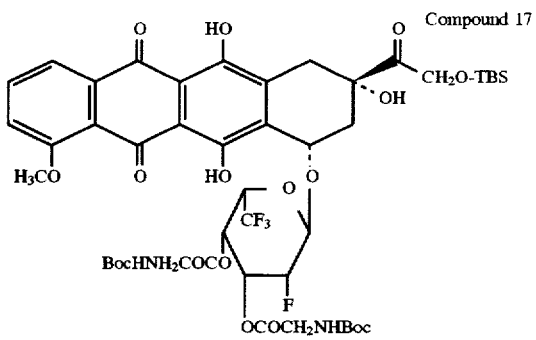

The mixture of Compounds 14 and 13 obtained in Example 12 (2), i.e. 14-O-tert-butyldimethylsilyl-7-O-{4-O-, and 14-O-tert-butyldimethylsilyl-7-O-{3-O-, |N-(tert-butoxycarbonyl)glycyl]-2,6-dideoxy-2,6,6,6-tetrafluoro-α-L-talopyranosyl}adriamycinone at the ratio of 2:1 (60 mg) was dissolved in anhydrous pyridine (0.9 ml). To the solution was added N-[N-(tert-butoxycarbonyl)glycyloxy| succinimide (55 mg) and the resulting mixture was stirred at 60° C. for 15 hrs to conduct the esterification reaction.

The reaction solution obtained was diluted with chloroform, washed successively with a 20% aqueous potassium hydrogen sulfate solution, a saturated aqueous sodium hydrogen carbonate solution and water, then dried over anhydrous sodium sulfate and concentrated under a reduced pressure. The residue was subjected to a silica gel column chromatography two times (first developer: chloroform-acetone, 15:1; and second developer: dichloromethane-acetone, 10:1) for the purpose of purification. The titled Compound 17 having the 3'- and 4'-hydroxyl groups both esterified with the N-protected glycyl groups, as a red solid (50 mg, yield 71%).

¹H-NMR spectrum (deutero-chloroform)
δ4.08 (3H, s, OCH₃)
1.44, 1.41 (each 9H, s, C(CH₃)₃ of Boc group)

(2) Preparation of 7-O-(2,6-dideoxy-2,6,6,6-tetrafluoro-3,4-di-O-glycyl-α-L-talopyranosyl)adriamycinone (Compound 18)

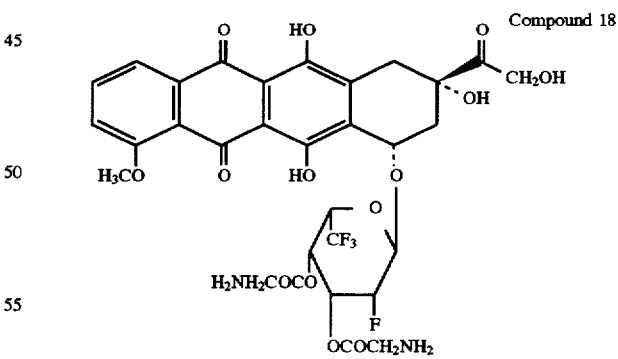

The solid of compound 17 obtained in item (1) above (50 mg) was dissolved in trifluoroacetic acid (0.8 ml) and the solution was allowed to stand at room temperature for 30 minutes. The reaction solution was concentrated under a reduced pressure and the residue was reprecipitated from methanol-ether. The titled compound 18 in the form of trifluoroacetate as a red solid (42 mg, yield 91%).

¹H-NMR spectrum (deutero-methanol)
δ4.02 (3H, s, OMe)
3.82 and 3.98 (each 2H, ABq, CH₂ of glycyl group)

EXAMPLE 14

(1) Preparation of 14-O-tert-butyldimethylsilyl-7-O-(2,6-dideoxy-6,6,6-trifluoro-α-L-lyxo-hexopyranosyl) adriamycinone (Compound 19)

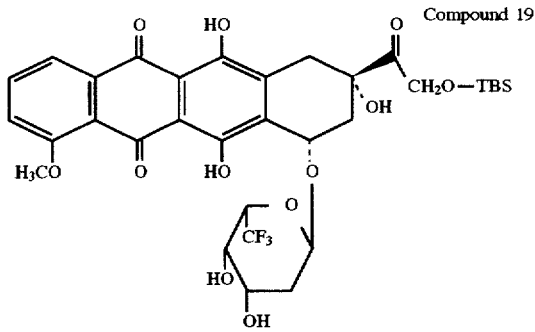
Compound 19

7-O-(2,6-Dideoxy-6,6,6-trifluoro-α-L-lyxo-hexopyranosyl)adriamycinone |the compound of formula (D) given hereinbefore| (155 mg) was dissolved in anhydrous DMF (1 ml), and to the solution were added imidazole (47 mg) and tert-butylchlorodimethylsilane (40 mg). The resulting mixture was stirred at room temperature for 2 hrs to effect the silylation of the 14-hydroxyl group of the Compound (D).

The reaction solution was post-treated as in Example 12 (1), to afford the titled Compound 19 as a red solid (146 mg, yield 79%).

¹H-NMR spectrum (deutero-chloroform)

δ4.01 (3H, s, OCH₃)
0.96 (9H, s, SiC(CH₃)₃)
0.16 (6H, s, Si(CH₃)₂)

(2) Preparation of 14-O-tert-butyldimethylsilyl-7-O-{3-O-[N-(tert-butoxycarbonyl)glycyl]-2,6-dideoxy-6,6,6-trifluoro-α-L-lyxo-hexopyranosyl}adriamycinone (Compound 20); and 14-O-tert-butyldimethylsilyl-7-O-{4-O-|N-(tert-butoxycarbonyl)glycyl|-2,6-dideoxy-6,6,6-trifluoro-α-L-lyxo-hexopyranosyl}adriamycinone (Compound 21)

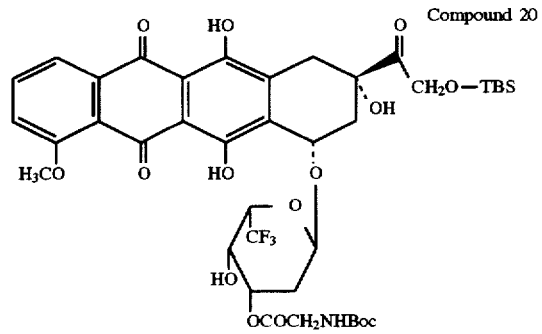
Compound 20

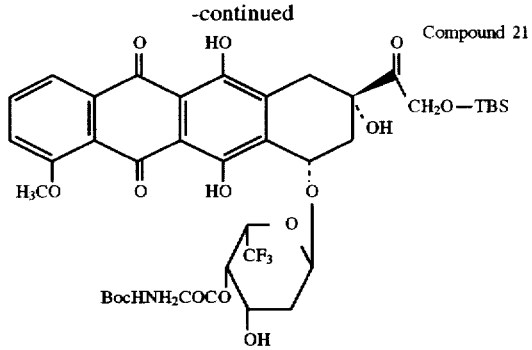
Compound 21

Compound 19 (100 mg) obtained in item (1) above was dissolved in anhydrous pyridine (1.5 ml), and to the solution was added N-|N-(tert-butoxycarbonyl)glycyloxy| succinimide (105 mg) and the resulting mixture was stirred at 60° C. for 2 hrs (for the purpose of the esterification reaction).

The reaction solution obtained was post-treated as in Example 12 (2), yielding the titled Compound 20 as a red solid (71 mg, yield 58%).

Compound 20 (71 mg) was then dissolved in anhydrous acetonitrile (3.5 ml), and to the solution was added a silica gel (Wako Gel C-200) (700 mg). The resultant mixture was stirred under reflux for 16 hrs to bring about the migration of the N-protected glycyl group to the 4'-position.

The reaction solution so obtained was post-treated as in Example 12 (2), to afford a mixture of Compounds 20 and 21 as a red solid (68 mg). The ratio of Compounds 20 to 21 was 1:3.

¹H-NMR spectrum (deutero-chloroform)
δ1.46, 1.42 (9H in combination, each s, C(CH₃)₃ of Boc group)

(3) Preparation of 7-O-(2,6-dideoxy-6,6,6-frifluoro-3-O-glycyl-α-L-lyxo-hexopyranosyl)adriamycinone (Compound 22) and 7-O-(2,6-dideoxy-6,6,6-trifluoro-4-O-glycyl-α-L-lyxo-hexopyranosyl)adriamycinone (Compound 23)

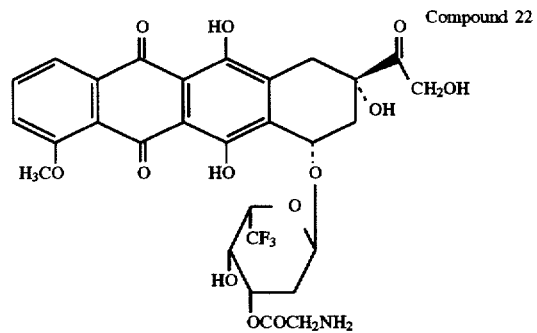
Compound 22

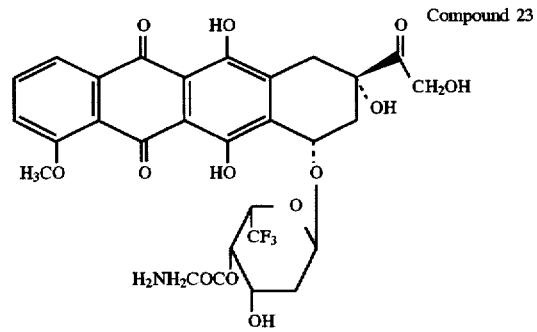
Compound 23

The mixture of Compounds 20 and 21 (65 mg) obtained in item (2) above was dissolved in aqueous trifluoroacetic acid (0.8 ml) and the resulting solution was allowed to stand at room temperature for 30 minutes. The reaction solution obtained was post-treated as in Example 12 (3), to afford a mixture of Compounds 22 and 23 in the form of trifluoroacetates (at the ratio of 1:4) (44 mg, yield 76%).

$^1$H-NMR spectrum (deutero-water)
δ5.34 (0.8H, br s, H-4' of Compound 23)
5.15 (0.2H, br d, H-3' of Compound 22)

EXAMPLE 15

(1) Preparation of 14-O-tert-butyldimethylsilyl-7-O-{3,4-di-O-[N-(tert-butoxycarbonyl)glycyl]-2,6-dideoxy-6,6,6-trifluoro-α-L-lyxo-hexopyranosyl}adriamycinone (Compound 24)

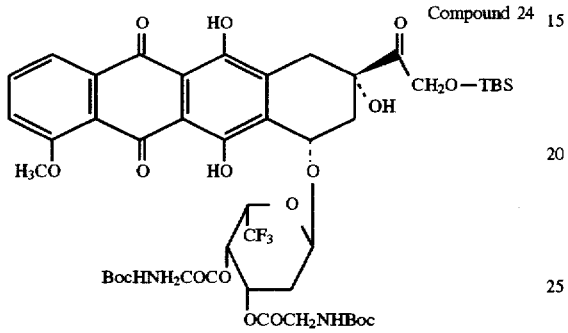

The mixture of Compounds 20 and 21 (at the ratio of 1:3) (54 mg) as obtained in Example 14 (2) was dissolved in anhydrous pyridine (0.7 ml), and to the solution was added N-[N-(tert-butoxycarbonyl)glycyloxy]succinimide (46 mg). The resulting mixture was stirred at 60° C. for 17 hrs to effect the esterification reaction. The reaction solution was post-treated as in Example 13 (1), to afford the titled Compound 24 as a red solid (48 mg, yield 76%).

$^1$H-NMR spectrum (deutero-chloroform)
δ4.03 (3H, s, OCH$_3$)
1.45, 1.41 (each 9H, each s, C(CH$_3$)$_3$ of Boc group)

(2) Preparation of 7-O-(2,6-dideoxy-6,6,6-trifluoro-3,4-di-O-glycyl-α-L-lyxo-hexopryranosyl)adriamycinone (Compound 25)

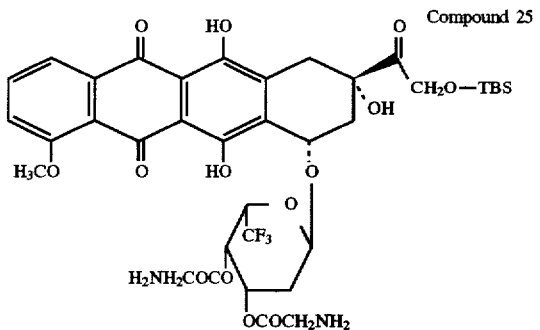

The solid of Compound 24 (40 mg) obtained in item (1) above was dissolved in aqueous trifluoroacetic acid (0.6 ml) and the solution was allowed to stand at room temperature for 30 minutes. The reaction solution obtained was post-treated as in Example 13 (2), to afford the titled Compound 25 in the form of trifluoroacetate as a red solid (32 mg, yield 87%).

$^1$H-NMR spectrum (deutero-methanol)
δ4.03 (3H, s, OCH$_3$)
3.81 and 4.01 (each 2H, ABq, CH$_2$ of glycyl group)

EXAMPLE 16

(1) Preparation of 14-O-tert-butyldimethylsilyl-7-O-{3-O-[N-(tert-butoxycarbonyl)-L-alanyl]-2,6-dideoxy-2,6,6,6-tetrafluoro-α-L-talopyranosyl}adriamycinone (Compound 26); and 14-O-tert-butyldimethylsilyl-7-O-{4-O-[N-(tert-butoxycarbonyl)-L-alanyl]-2,6-dideoxy-2,6,6,6-tetrafluoro-α-L-talopyranosyl}adriamycinone (Compound 27)

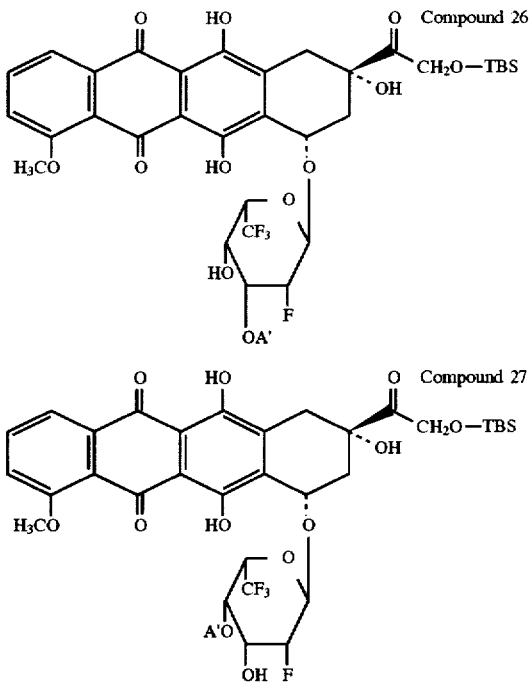

In the formulae above, A' means N-Boc-L-alanyl group.

Compound 12 (109 mg) obtained in Example 12 (1) was dissolved in anhydrous pyridine (1.6 ml), and to the solution was added N-[N-(tert-butoxycarbonyl)-L-alanyloxy]succinimide (129 mg). The resulting mixture was stirred at 60° C. for 3 hrs. The reaction solution obtained was subjected to a post-treatment in the same manner as in Example 12 (2) and the residue obtained was purified by a silica gel column chromatography (developer; chloroform-acetone, 4:1), to afford a mixture of the titled Compounds 26 and 27 as a red solid (102 mg, yield 76%). A $^{19}$F-NMR spectrum shows the ratio of Compounds 26 to 27 to be about 2:1.

$^{19}$F-NMR spectrum (deutero-chloroform, CFCl$_3$ as internal standard)

δ-197.5 (0.65F, ddt, F-2 of Compound 26)
-202.1 (0.35F, ddd, F-2 of Compound 27)

The mixture (91 mg) was then dissolved in anhydrous acetonitrile (10 ml) and to the solution was added a silica gel (900 mg). The resultant mixture was stirred under reflux for 15 hrs. The reaction solution was post-treated in the same manner as in Example 12 (2), thus affording a mixture of the titled Compounds 26 and 27 (89 mg). A $^{19}$F-NMR spectrum shows the ratio of Compounds 26 to 27 to be about 1:3, Compound 27 being the main product.

(2) Preparation of 7-O-(3-O-L-alanyl-2,6-dideoxy-2,6,6,6-tetrafluoro-α-L-talopyranosyl)adriamycinone (Compound 28) and 7-O-(4-O-L-alanyl-2,6-dideoxy-2,6,6,6-tetrafluoro-α-L-talopyranosyl)adriamycinone (Compound 29)

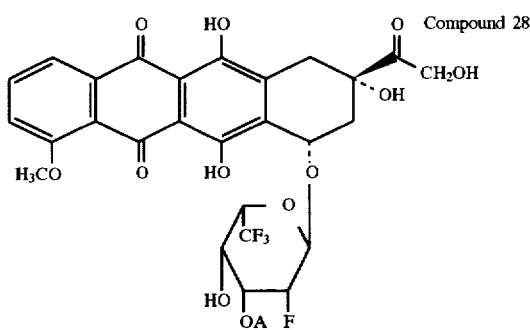

Compound 28

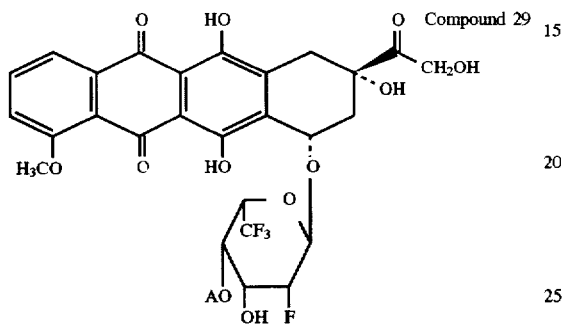

Compound 29

In the formulae above, A means L-alanyl group.

To the mixture of Compounds 26 and 27 (about 1:3 ratio) (80 mg), which was obtained in item (1) above, trifluoroacetic acid (1 ml) was added under ice-cooling, and the mixture so obtained was stirred at room temperature for 30 minutes. The reaction solution was post-treated in the same manner as in Example 12 (3), to afford a mixture of Compounds 28 and 29 (as trifluoroacetates) as a red solid (65 mg, yield 91%). The ratio of Compounds 28 to 29 in the mixture was about 1:4.

$^1$H-NMR spectrum (deutero-methanol)

δ1.55 (0.6H, d, CH$_3$ of alanyl group of Compound 28)
1.60 (2.4H, d, CH$_3$ of alanyl group of Compound 29)

EXAMPLE 17

(1) Preparation of 14-O-tert-butyldimethylsilyl-7-O-{3,4-di-O-[N-(tert-butoxycarbonyl)-L-alanyl]-2,6-dideoxy-2,6,6,6-tetrafluoro-α-L-talopyranosyl}adriamycinone (Compound 30)

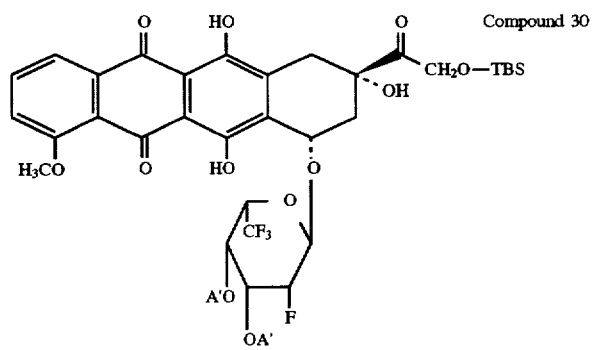

Compound 30

In the formula above, A' means N-Boc-L-alanyl group.

The mixture of Compounds 26 and 27 at the ratio of about 1:3 (48 mg) which was obtained in Example 16 (1) was dissolved in anhydrous pyridine (0.7 ml). To the solution was added N-[N-(tert-butoxycarbonyl)-L-alanyloxy] sccinimide (46 mg), and the resulting mixture was stirred at 60° C. for 17 hrs. The reaction solution, after water (0.1 ml) was added thereto, was stirred at room temperature for 3 hrs and then post-treated as in Example 13 (1) to leave a residue, which was purified by a silica gel column chromatography (developer: benzeneacetone, 8:1), to afford the titled Compound 30 as a red solid (18 mg, yield 32%).

$^1$H-NMR spectrum (deutero-chloroform)

δ4.08 (3H, s, OCH$_3$)
1.44, 1.41,(18H in combination, each C(CH$_3$)$_3$ of Boc group (2) Preparation of 7-O-(3,4-di-O-L-alanyl-2,6-dideoxy-2,6,6,6-tetrafluoro-α-L-talopyranosyl)adriamycinone (Compound 31)

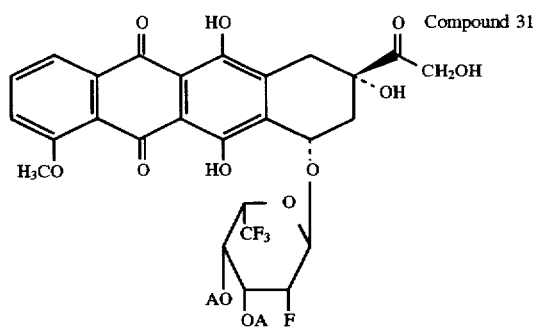

Compound 31

In the formula above, A means L-alanyl groups.

To Compound 30 (15 mg) obtained in item (1) above was added trifluoroacetic acid (0.2 ml) under ice-cooling and the solution obtained was stirred for 30 minutes. The reaction solution was post-treated as in Example 13 (2), affording the titled Compound 31 (as trifluoroacetate) as a red solid (11.5 mg, yield 89%).

$^1$H-NMR spectrum (deutero-methanol)

δ4.01 (3H, S, OCH$_3$)
1.65, 1.50 (each 3H, each d, CH$_3$ of L-alanyl group)

EXAMPLE 18

(1) Preparation of 14-O-tert-butyldimethlysilyl-7-O-{3-O-[N-(tert-butoxycarbonyl)-L-phenylalanyl]-2,6-dideoxy-2,6,6,6-tetrafluoro-α-L-talopyranosyl}adriamycinone (Compound 32) and 14-O-tert-butyldimethylsilyl-7-O-{4-O-[N-(tert-butoxycarbonyl)-L-phenylalanyl]-2,6-dideoxy-2,6,6,6-tetrafluoro-α-L-talopyranosyl}adriamycinone (Compound 33)

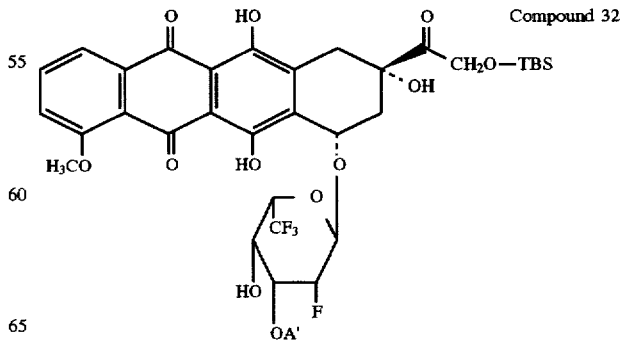

Compound 32

53
-continued

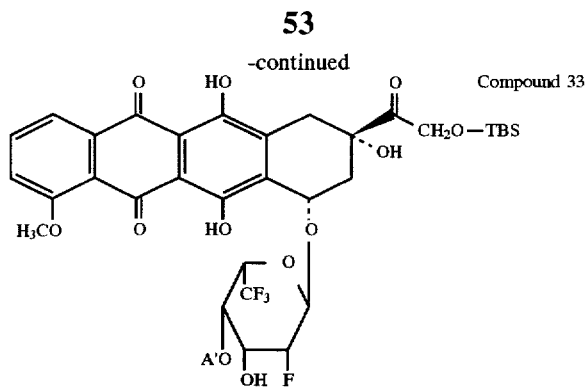
Compound 33

In the formulae above, A' represents N-Boc-L-phenylalanyl group.

Compound 12 (48 mg) obtained in Example 12 (1) was dissolved in anhydrous pyridine (0.8 ml), and to the solution was added N-[N-(tert-butoxycarbonyl)-L-phenylalanyloxy] succinimide (71 mg), and the mixture was stirred at 60° C. for 3 hrs.

The reaction solution was post-treated as in Example 12 (2) and the resulting solid was purified by a silica gel column chromatography two times (first developer: chloroform-acetone, 4:1; and second developer: toluene-ethyl acetate, 3:1), thus yielding the titled Compound 32 as a red solid (53 mg, yield 82%).

$^1$H-NMR spectrum (deutero-chloroform)
δ4.08 (3H, s, OCH$_3$)
1.39 (9H, s, C(CH$_3$)$_3$ of Boc group)

$^{19}$F-NMR spectrum (deutero-chloroform, CFCl$_3$ as internal standard)
δ-198.4 (ddt)

Compound 32 (45 mg) was then dissolved in anhydrous acetonitrile (8 ml), and to the solution was added a silica gel (Wako Gel C-200) (450 mg). The mixture was refluxed for 45 hrs to effect the reaction. The reaction solution was post-treated as in Example 12 (2), thus affording a mixture of the titled Compounds 32 and 33 as a red solid (42 mg). The ratio of Compounds 32 to 33 in the mixture was about 1:3.

$^{19}$F-NMR spectrum (deutero-chloroform, CFCl$_3$ as internal standard)
δ-198.4 (0.24F, ddt, F-2' of Compound 32)
-203.5 (0.76F, ddd, F-2' of Compound 33)

(2) Preparation of 7-O-(2,6-dideoxy-2,6,6,6-tetrafluoro-3-O-L-phenylalanyl-α-L-talopyranosyl)adriamycinone (Compound 34) and 7-O-(2,6-dideoxy-2,6,6,6-tetrafluoro-4-O-L-phenylalanyl-α-L-talopyranosyl)adriamycinone (Compound 35)

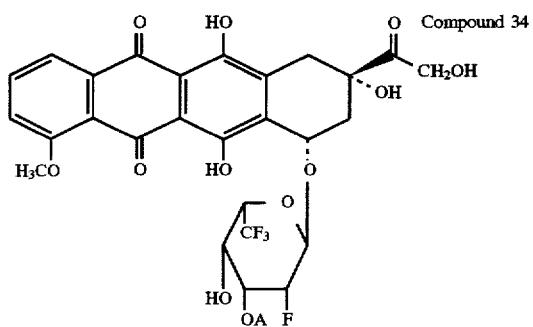
Compound 34

54
-continued

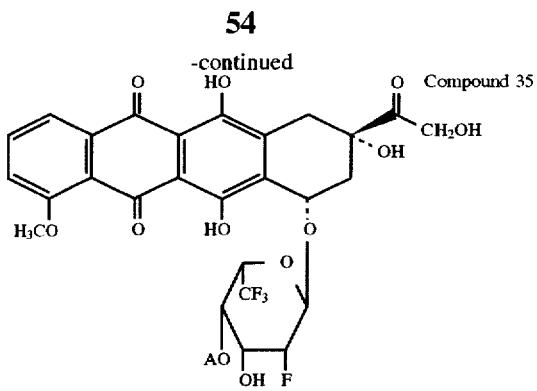
Compound 35

In the formula above. A represents L-phenylalanyl groups.

To the mixture of Compounds 32 and 33 at the ratio of about 1:3 (34 mg) which was obtained in item (1) above was added aqueous trifluoroacetic acid under ice-cooling to give a solution, which was then stirred at room temperature for 30 minutes. The reaction solution was post-treated as in Example 12 (3), thus affording a mixture of the titled Compounds 34 and 35 (as trifluoroacetates) as a red solid (24 mg, yield 79%). The ratio of Compounds 34 to 35 was about 1:3.5.

$^{19}$F-NMR spectrum (deutero-methanol, CFCl$_3$ as internal standard)
-199.1 (0.22F, ddd, F-2' of Compound 34)
-202.0 (0.78F, ddd, F-2' of Compound 35)

EXAMPLE 19

(1) Preparation of 14-O-tert-butyldimethylsilyl-7-O-{3,4-di-O-[N-(tert-butoxycarbonyl)-L-phenylalanyl]-2,6-dideoxy-2,6,6,6-tetrafluoro-α-L-talopyranosyl}adriamycinone (Compound 36)

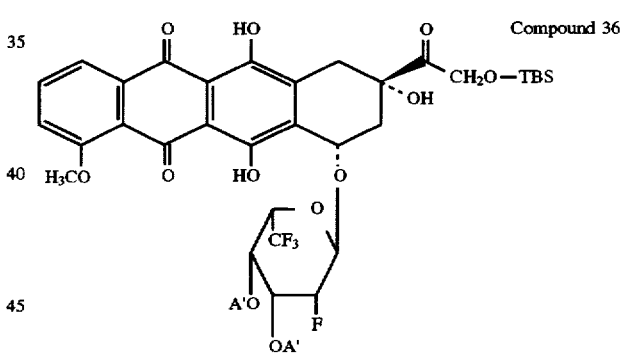
Compound 36

In the formula above, A' represents N-Boc-L-phenylalanyl group.

The mixture of Compounds 32 and 33 at the ratio of about 1:3 (35 mg) which was obtained in Example 18 (1) was dissolved in anhydrous pyridine (0.6 ml), and to the solution was added N-[N-(tert-butoxycarbonyl)-L-phenylalanyloxy] succinimide (39 mg). The resulting mixture was stirred at 60° C. for 17 hrs. The reaction solution, after water (0.05 ml) was added thereto, was stirred at room temperature for 15 hrs and then post-treated as in Example 13 (1) to leave a residue. The residue was subjected to a silica gel column chromatography (developer: chloroform-acetone, 15:1) for isolation and purification of the desired product, to afford the titled Compound 36 as a red solid (31 mg, yield 72%).

$^1$H-NMR spectrum (deutero-chloroform)
δ4.08 (3H, s, OCH$_3$)
1.35, 1.34 (18H in combination, each s, C(CH$_3$)$_3$ of Boc group)

(2) Preparation of 7-O-(2,6-dideoxy-2,6,6,6-tetrafuluoro-3,4-di-O-L-phenylalanyl-α-L-talopyranosyl)adriamycinone (Compound 37)

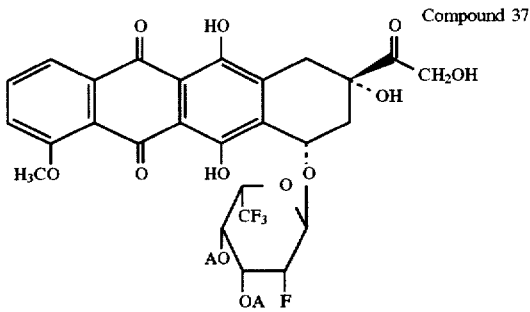

In the formula above, A represents L-phenylalanyl group.

To Compound 36 (25 mg) obtained in item (1) above was added aqueous trifluoroacetic acid (0.4 ml) under ice-cooling, and the solution was stirred at room temperature for 30 minutes. The reaction solution was concentrated under a reduced pressure and the residue obtained was reprecipitated from methanol-isopropylether, thus affording the titled Compound 37 (as trifluoroacetate) as a red solid (17 mg, yield 73%).

$^1$H-NMR spectrum (deutero-methanol)
δ–7.3 (10H, m, Ph×2)
4.01 (3H, s, OCH$_3$)

EXAMPLE 20

(1) Preparation of 14-O-tert-butyldimethylsilyl-7-O-{3-O-[N-tert-butoxycarbonyl)-L-alanyl]-2,6-dideoxy-6,6,6-trifluoro-α-L-lyxo-hexopyranosyl}adriamycinone (Compound 38) and 14-O-tert-butyldimethylsilyl-7-O-{4-O-[N-tert-butoxycarbonyl)-L-alanyl]-2,6-dideoxy-6,6,6-trifluoro-α-L-lyxo-hexopyranosyl}adriamycinone (Compound 39)

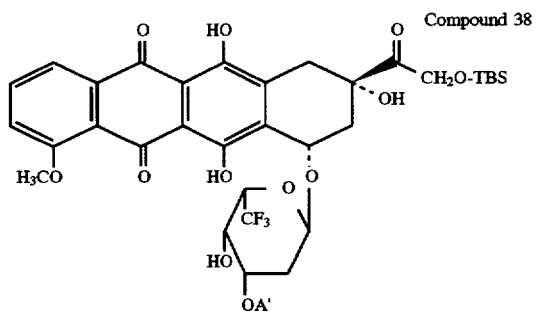

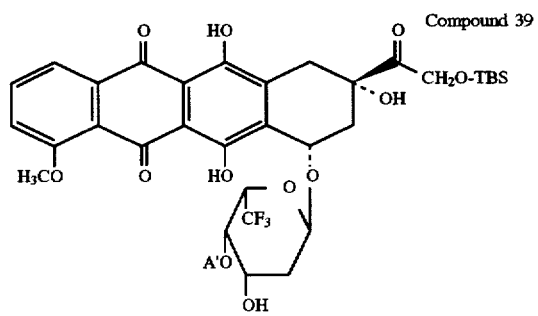

In the formulae above, A' represents N-Boc-L-alanyl group.

Compound 19 (86 mg) obtained in Example 14 (1) was dissolved in anhydrous pyridine (1.4 ml), and to the solution was added N-|N-(tert-butoxycarbonyl)-L-alanyloxy| succinimide (104 mg). The resulting mixture was stirred at 60° C. for 3 hrs. The reaction solution was post-treated as in Example 12 (2) and the residue obtained was purified by a silica gel column chromatography two times (first developer: chloroform-acetone, 4:1; and second developer: tolueneethyl-acetate, 3:1), to afford a mixture of the titled Compounds 38 and 39, as a red solid (83 mg, yield 78%).

Then the mixture of Compounds 38 and 39 (76 mg) was dissolved in anhydrous acetonitrile, to which was added a silica gel (700 mg), and the resulting mixture was stirred under reflux for 15 hrs to effect the reaction of transfer of the N-protected-L-alanyl group to the 4'-position. The reaction solution obtained was post-treated as in Example 12 (2), yielding a mixture of the titled Compounds 38 and 39 (73 mg) as a red solid. The ratio of Compounds 38 to 39 in the mixture obtained was about 1:4.

$^1$H-NMR spectrum (deutero-chloroform)
δ1.43, 1.40 (9H in combination, each s, C(CH$_3$)$_3$ of Boc group)

(2) Preparation of 7-O-(3-O-L-alanyl-2,6-dideoxy-6,6,6-trifluoro-α-L-lyxo-hexopyranosyl)adriamycinone (Compound 40) and 7-O-(4-O-L-alanyl-2,6-dideoxy-6,6,6-trifluoro-α-L-lyxo-hexopyranosyl)adriamycinone (Compound 41)

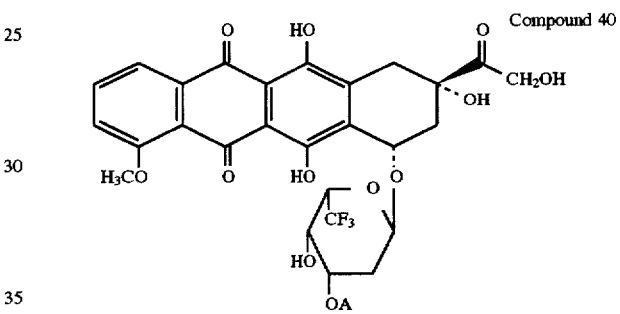

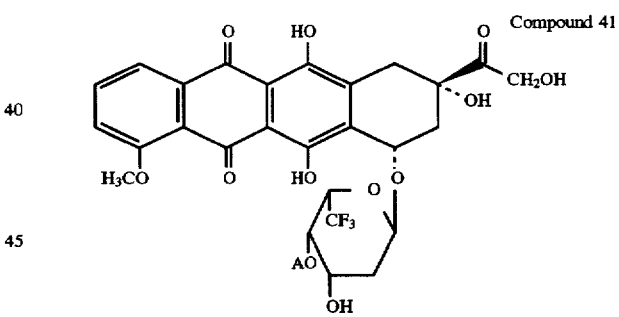

In the formulae above, A represents L-alanyl group.

To the mixture of Compounds 38 and 39 (at a ratio of about 1:4) (62 mg) obtained in item (1) above was added trifluoroacetic acid (0.9 ml) under ice-cooling and the solution was stirred at room temperature for 30 minutes. The reaction solution was post-treated as in Example 12 (3) to afford a mixture of the titled Compounds 40 and 41 (as trifluoroacetates) as a red solid (50 mg, yield 91%). The ratio of Compounds 40 to 41 was 1:5.5.

$^1$H-NMR spectrum (deutero-methanol)
δ5.25 (0.85H, br s, H-4' of Compound 41)
5.08 (0.15H, m, H-3' of Compound 40)

EXAMPLE 21

(1) Preparation of 14-O-tert-butyldimethylsilyl-7-O-{3,4-di-O-|N-(tert-butoxycarbonyl)-L-alanyl|-2,6-dideoxy-6,6,6-trifluoro-α-L-lyxo-hexopyranosyl}adriamycinone (Compound 42)

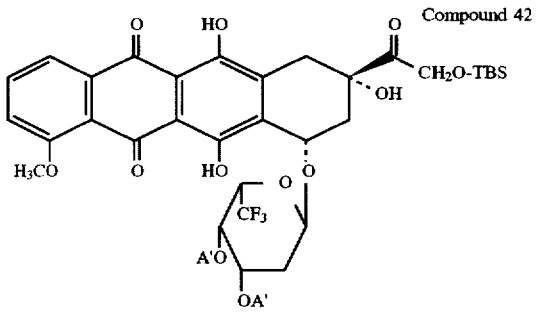

Compound 42

In the formula above, A' represents N-Boc-L-alanyl group.

The mixture of Compounds 38 and 39 (at ratio of about 1:4) (25 mg) as obtained in Example 20 (1) was dissolved in anhydrous pyridine (3.5 ml), and to the solution was added an active ester, N-[N-(tert-butoxycarbonyl)-L-alanyloxyl] succinimide (24 mg). The mixture so obtained was stirred at 60° C. for 18 hrs. Then, water (0.1 ml) was added to the reaction solution, which was stirred for 3 hrs at room temperature. The reaction solution so abtained was post-treated as in Example 13 (1) and the residue obtained was purified by a silica gel column chromatography (developer: benzene-acetone, 7:1), affording the titled Compound 42 as a red solid (10 mg, yield 34%). The mixture of the starting Compounds 38 and 39 was recovered at a yield of 32%.

$^1$H-NMR spectrum (deutero-chloroform)

δ4.09 (3H, s, OCH$_3$)

1.43, 1.39 (18H in combination, each s, C(CH$_3$)$_3$ of Boc group)

(2) Preparation of 7-O-(3,4-di-O-L-alanyl-2,6-dideoxy-6,6,6-trifluoro-α-L-lyxo-hexopyranosyl)adriamycinone (Compound 43)

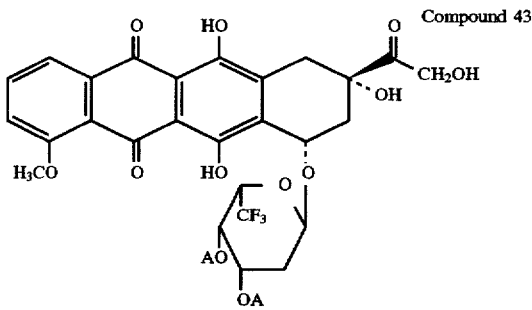

Compound 43

In the formula above, A represents L-alanyl group.

To Compound 42 (9 mg) obtained in item (1) above was added trifluoroacetic acid (0.15 ml) under ice-cooling and the resulting solution was allowed to stand at room temperature for 30 minutes. The reaction solution was post-treated as in Example 13 (2) and there was afforded the titled Compound 43 (as trifluoroacetate) as a red solid (7.8 mg, yield 95%).

$^1$H-NMR spectrum (deutero-methanol)

δ1.65, 1.49 (each 3H, each d, CH$_3$ of L-alanyl group)

EXAMPLE 22

(1) Preparation of 14-O-tert-butyldimethylsilyl-7-O-{3-O-[N-(tert-butoxycarbonyl)-L-phenylalanyl]-2,6-dideoxy-6,6,6-trifluoro-α-L-lyxo-hexopyranosyl}adriamycinone (Compound 44) and 14-O-tert-butyldimethylsilyl-7-O-{4-O-[N-(tert-butoxycarbonyl)-L-phenylalanyl]-2,6-dideoxy-6,6,6-trifluoro-α-L-lyxo-hexopyranosyl}adriamycinone (Compound 45)

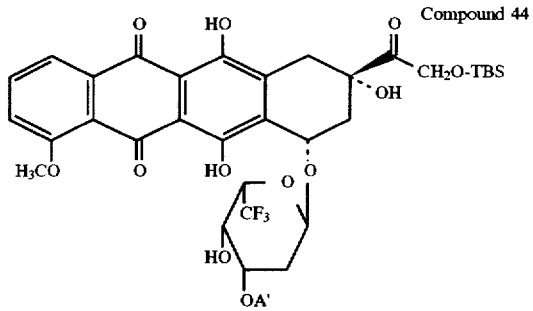

Compound 44

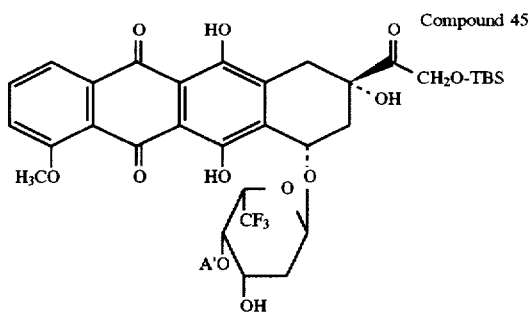

Compound 45

In the formulae above, A' represents N-Boc-L-phenylalanyl group.

Compound 19 (58 mg) obtained in Example 14 (1) was dissolved in anhydrous pyridine (0.9 ml) and to the solution was added N-[N-(tert-butoxycarbonyl)-L-phenylalanyloxy] succinimide (88 mg). The mixture obtained was stirred at room temperature for 3 hrs. The reaction solution was post-treated as in Example 12 (2) and the residue obtained was purified by a silica gel column chromatography twice (first developer: chloroform-acetone, 4:1; and second developer: toluene-ethyl acetate, 3:1) to afford the titled Compound 44 as a red solid (65 mg, yield 83%).

$^1$H-NMR spectrum (deutero-chloroform)

δ4.09(3H, s, OCH$_3$)

1.41 (9H, s, C(CH$_3$)$_3$ of Boc group)

Then, the Compound 44 obtained (60 mg) was dissolved in anhydrous acetonitrile (20 ml), to which was added a silica gel (600 mg). The resultant mixture was stirred under reflux for 35 hrs. The reaction solution was post-treated as in Example 12 (2), thus affording a mixture of the titled Compounds 44 and 45 (58 mg) as a red solid. The ratio of Compounds 44 to 45 was about 1:2.

$^1$H-NMR spectrum (deutero-chloroform)

δ1.41, 1.44 (9H in combination, each s, C(CH$_3$)$_3$ of Boc group)

(2) Preparation of 7-O-(2,6-dideoxy-6,6,6-trifluoro-3-O-L-phenylalanyl-α-L-lyxo-hexopyranosyl)adriamycinone (Compound 46) and 7-O-(2,6-dideoxy-6,6,6-trifluoro-4-O-L-phenylalanyl-α-L-lyxo-hexopyranosyl)adriamycinone (Compound 47)

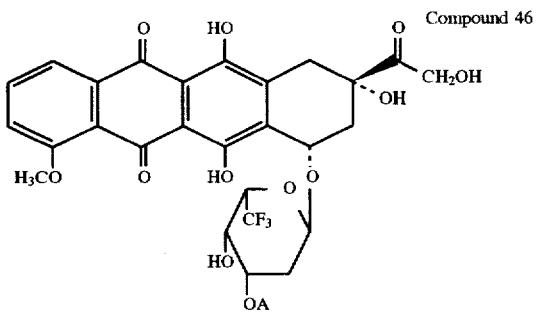

Compound 46

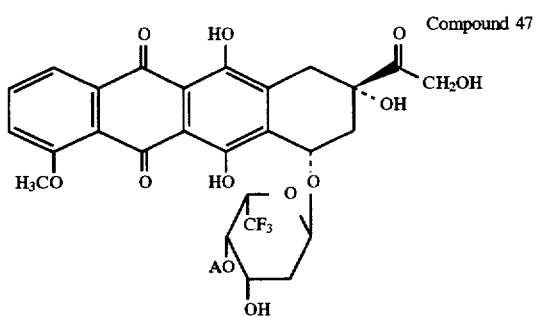

Compound 47

In the formulae above, A represents L-phenylalanyl group.

To the mixture of Compounds 44 and 45 (at a ratio of about 1:2) (41 mg) obtained in item (1) above was added trifluoroacetic acid (0.6 ml) under ice-cooling and the resulting solution was allowed to stand at room temperature for 30 minutes. The reaction solution was post-treated as in Example 12 (3), affording a mixture of the titled Compounds 46 and 47 (as trifluoroacetates) as a red solid (33 mg, yield 91%). The ratio of Compounds 46 to 47 was about 1:4.

$^1$H-NMR spectrum (deutero-methanol)
δ5.25 (0.8H, br s, H-4' of Compound 47)
5.10 (0.2H, m, H-3' of Compound 46)

EXAMPLE 23

(1) Preparation of 14-O-tert-butyldimethylsilyl-7-O-{3,4-di-O-[N-(tert-butoxycarbonyl)-L-phenylalanyl]-2,6dideoxy-6,6,6-dideoxy-6,6,6-trifluoro-α-L-lyxo-hexopyranosyl}adriamycinone (Compound 48)

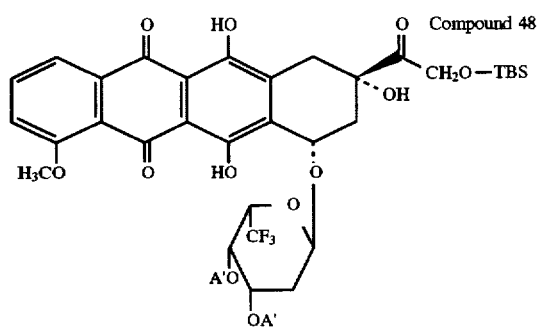

Compound 48

In the formula above, A' represents N-Boc-L-phenylalanyl group.

The mixture of Compounds 44 and 45 (at a ratio of about 1:2) (28 mg) as obtained in Example 22 (1) was dissolved in anhydrous pyridine (0.5 ml), and to the solution was added an active ester, N-[N-(tert-butoxycarbonyl)-L-phenylalanyloxy] sccinimide, (32 mg). The mixture obtained was stirred at 60° C. for 16 hrs. Then, water (0.05 ml) was added to the reaction solution and the resultant mixture was stirred at room temperature for 15 hrs, followed by post-treating the reaction solution as in Example 13 (1). The residue obtained was purified by a silica gel column chromatography (developer: chloroform-acetone, 20:1) to afford the titled Compound 48 as a red solid (26 mg, yield 74%).

$^1$H-NMR spectrum (deutero-chloroform)
δ4.08 (3H, s, OCH$_3$)
1.37, 1.35 (18H in combination, each s, C(CH$_3$)$_3$ of Boc group)

(2) Preparation of 7-O-(2,6-dideoxy-6,6,6-trifluoro-3,4-di-O-L-phenylalanyl-α-L-lyxo-hexopyranosyl)adriamycinone (Compound 49)

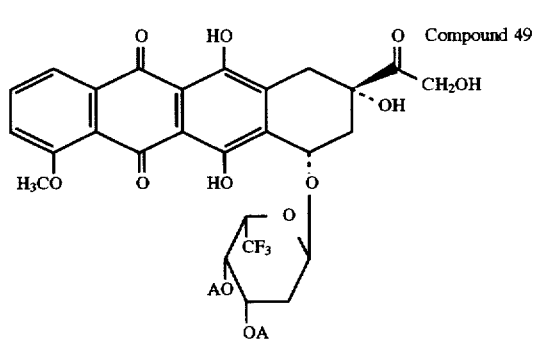

Compound 49

In the formula above, A represents L-phenylalanyl group.

To Compound 48 (23 mg) obtained in item (1) above was added trifluoroacetic acid (0.3 ml) under ice-cooling, and the resulting solution was allowed to stand at room temperature for 30 minutes. The reaction solution was post-treated as in Example 13 (2), affording the titled Compound 49 (as trifluoroacetate) as a red solid (17 mg, yield 80%).

$^1$H-NMR spectrum (deutero-methanol)
δ7.1~7.45 (10H, m, Ph×2)
4.03 (3H, s, OCH$_3$)

(J) 7-O-(2,6-Dideoxy-2,6,6,6-tetrafluoro-α-L-talopyranosyl)adriamycinone of the formula (C-b) given hereinbefore, which is employed as the starting compound for the production of the adriamycinone derivatives of the general formula (II-1a), general formula (II-1b) and general formula (II-1c) according to the second aspect of this invention, is a new compound. The preparation of this new adriamycinone derivative of the formula (C-b) is briefly described below.

For the preparation of 7-O-(2,6-dideoxy-2,6,6,6-tetrafluoro-α-L-talopyranosyl)adriamycinone having the formula (C-b), it is necessary to use 1-O-acetyl derivative of 2,6-dideoxy-2,6,6,6-tetrafluoro-α-L-talopyranose or 3,4-di-O-protected derivatives thereof, or a 3,4-di-O-protected-2,6-dideoxy-2,6,6,6-tetrafluoro-α-L-talopyranosyl iodide or bromide which are the new sugar compounds. The respective steps (1) to (13) involved in the method for the synthesis of these new sugar compounds are firstly explained now in brief. Referential Example 1 given hereinafter will be referred to as detailed descriptions of the reactions which are effected in the respective steps of said synthetic method.

In the following descriptions, abbreviations Bn and Ac appear in different formulae given hereinafter, wherein Bn means benzyl group and Ac means acetyl group.

Step (1): A known compound, methyl α-D-lyxopyranoside [Compound 50] of the formula

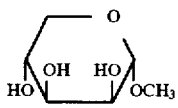

is reacted with diethylaminosulfur trifluoride [(C₂H₅)₂NSF₃] to fluorinate selectively only the 4-hydroxyl group of Compound 50, whereby there is produced methyl 4-deoxy-4-fluoro-α-L-ribopyranoside [Compound 51] of the formula

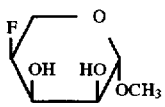

as a 4-deoxy-4-fluoro derivative of Compound 50, with accompanying reversion of the steric configuration of the starting compound.

Step (2): The hydroxyl groups at the 2- and 3-positions of Compound 51 are benzylated by reaction with benzyl bromide, whereby there is produced methyl 2,3-di-O-benzyl-4-deoxy-4-fluoro-α-L-ribopyranoside [Compound 52] of the formula

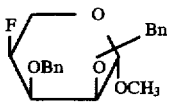

Step (3): Compound 52 is hydrolyzed with acid to cleave the glycoside linkage at the 1-position of said compound, whereby there is produced 2,3-di-O-benzyl-4-deoxy-4-fluoro-L-ribopyranose [Compound 53] of the formula

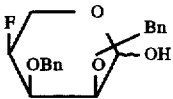

Step (4): Compound 53 is reacted with 1,3-propanedithiol in the presence of boron trifluoride-ethyl ether to cleave the sugar ring of Compound 53, whereby there is produced 2,3-di-O-benzyl-4-deoxy-4-fluoro-L-ribose trimethylene dithioacetal [Compound 54] of the formula

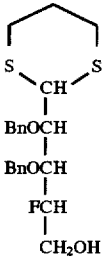

as a straight-chain compound of the dithioacetal type.

Step (5): The primary hydroxyl group of Compound 54 is acetylated with acetic anhydride to produce 5-O-acetyl-2,3-di-O-benzyl-4-deoxy-4-fluoro-L-ribose trimethylene dithioacetal [Compound 55] of the formula

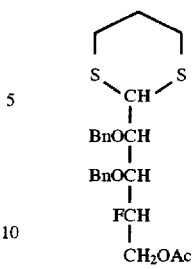

Step (6): Compound 55 is reacted with mercury perchlorate in aqueous tetrahydrofuran in the presence of calcium carbonate to cleave the dithioacetal ring of Compound 55, whereby there is produced 5-O-acetyl-2,3-di-O-benzyl-4-deoxy-4-fluoro-aldehyde-L-ribose [Compound 56] of the formula

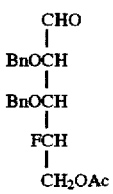

as an aldehyde-type compound.

Step (7): Compound 56 is then reacted with trifluoromethyltrimethylsilane in anhydrous tetrahydrofuran in the presence of tetrabutylammonium fluoride. Thereby, there are produced 6-O-acetyl-3,4-di-O-benzyl-1,5-dideoxy-1,1,1,5-tetrafluoro-L-altritol [Compound 57] of the formula

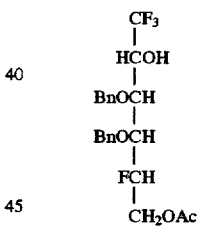

as an L-altritol derivative having a trifluoromethyl group incorporated therein and its 2-epimer [Compound 58] of the formula:

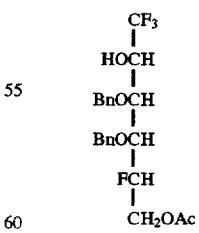

Step (8): Compound 57 is treated with a methanolic solution of sodium methoxide to remove the acetyl group from Compound 57. There is thus produced 3,4-di-O-benzyl-1,5-dideoxy-1,1,1,5-tetrafluoro-L-altritol [Compound 59] of the formula

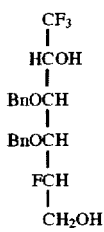

as a diol.

Step (9): Reactions of oxidizing selectively the primary hydroxyl group of Compound 59 and forming simultaneously the ring of a pyranose are then conducted. For this purpose, the 2- and 6-hydroxyl groups of Compound 59 are trimethylsilylated, followed by effecting Collin's oxidation of the resulting trimethylsilylated product. Thus, the primary trimethylsilyloxy group of the resulting trimethylsilylated product is subjected to selective oxidation to afford an aldehyde product. This aldehyde product is then hydrolyzed with acid to remove the remaining trimethylsilyl group and concurrently bring about the cyclization reaction, whereby there is produced 3,4-di-O-benzyl- 2,6-dideoxy-2,6,6,6-tetrafluoro-α-L-talopyranose [Compound 60] of the formula

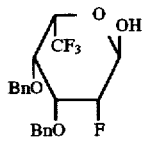

as a 2,6-dideoxy-2,6,6,6-tetrafluorotalopyranose derivative.

Step (10): The 1-hydroxyl group of Compound 60 is then acetylated with acetic anhydride to produce 1-O-acetyl-3,4-di-O-benzyl-2,6-dideoxy-2,6,6,6-tetrafluoro-α-L-talopyranose [Compound 61] of the formula

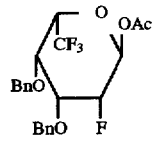

Step (11): The benzyl groups at the 3- and 4-positions of Compound 61 are removed therefrom by catalytic reduction to produce 1-O-acetyl-2,6-dideoxy-2,6,6,6-tetrafluoro-α-L-talopyranose [Compound 62] of the formula

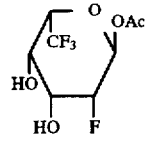

Step (12): The hydroxyl groups at the 3- and 4-positions of compound 62 are acetylated with acetic anhydride, whereby there is produced 1,3,4-tri-O-acetyl-2,6-dideoxy-2,6,6,6-tetrafluoro-α-L-talopyranose [Compound 63] of the formula

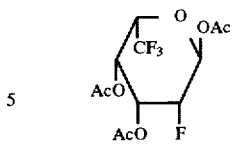

as a tri-O-acetylated product.

Step (13): Compound 63 is reacted with iodotrimethylsilane [(CH₃)₃SiI] in anhydrous toluene, whereby there is produced 3,4-di-O-acetyl-2,6-dideoxy-2,6,6,6-tetrafluoro-L-talopyranosyl iodide [Compound 64] of the formula

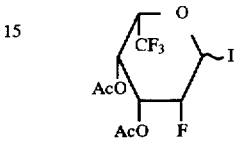

as a 1-iodo sugar.

Otherwise, 7-O-(2,6-Dideoxy-2,6,6,6-tetrafluoro-α-L-talopyranosyl)adriamycinone of the aforesaid formula (C-b) may also be produced by such a method which comprises providing adriamycinone; protecting the 14-hydroxyl group of adriamycinone with tert-butyldimethylsilyl group (abbreviated as TBS) as an appropriate hydroxyl-protecting group; thereby preparing 14-O-tert-butyldimethylsilyl-adriamycinone; condensing the 7-hydroxyl group of the latter compound with the aforesaid Compound 40, namely 3,4-di-O-acetyl-2,6-dideoxy-2,6,6,6-tetrafluoro-L-talopyranosyl iodide; and then eliminating the remaining hydroxyl-protecting group (TBS) from the resultant condensation product.

In the above-mentioned method for the preparation of the adriamycinone derivative of the formula (C-b), it is convenient that the condensation reaction of the above 14-O-TBS-adriamycinone with Compound 40 (the sugar iodide) is carried out by dissolving these two compounds in an organic solvent such as dichloroethane, adding to the resulting organic solution catalytic amounts of mercuric iodide or bromide, yellow-colored mercuric oxide and Molecular Sieve 3A, and effecting said condensation reaction in the presence of the above-mentioned catalyst, and that the α-L-condensation product so formed is recovered from the reaction solution and then subjected to a deprotecting treatment for removal of the hydroxyl-protecting acetyl group therefrom by an ester-exchange reaction and further to a deprotecting treatment for removal of the silyl group (TBS) by hydrolysis, thereby affording the target compound of the formula (C-b) see Referential Example 3 described hereinafter.

(K) 7-O-(2,6-Dideoxy-6,6,6-trifluoro-α-L-lyxo-hexopyranosyl)adriamycinone of the formula (D) given hereinbefore, which is employed as the starting compound for the production of the adriamycinone derivatives of the general formula (II-2a), general formula (II-2b) and general formula (II-2c) according to the second aspect of this invention, is also a new compound.

For the preparation of the 7-O-(2,6-dideoxy-6,6,6-trifluoro-α-L-lyxo-hexopyranosyl)adriamycinone of the formula (D), it is necessary to use 1-O-acetyl derivative of 2,6-dideoxy-6,6,6-trifluoro-α-L-lyxo-hexopyranose or 3,4-di-O-protected derivative thereof, or a 3,4-di-O-protected-2,6-dideoxy-6,6,6-trifluoro-α-L-lyxo-hexopyranosyl iodide or bromide which are new sugar compounds. The respective steps (1') to (12') involved in the method for the synthesis of these new sugar compounds are explained below firstly in brief. However, Referential Example 2 given hereinafter will be referred to as detailed descriptions of the reactions which are effected in the respective steps of said synthetic method.

Step (1'): A known compound, methyl 4-deoxy-β-L-erythro-pentopyranoside [Compound 65] of the formula

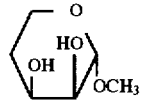

is employed and the 2- and 3-hydroxyl groups of Compound 65 are benzylated by reaction with benzyl bromide, whereby there is produced methyl 2,3-di-O-benzyl-4-deoxy-β-L-erythro-pentopyranoside [Compound 66] of the formula

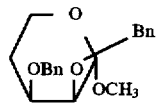

Step (2'): Compound 66 is hydrolyzed with acid to cleave the glycoside linkage at the 1-position of said compound, whereby there is produced 2,3-di-O-benzyl-4-deoxy-L-erythro-pentopyranose [Compound 67] of the formula

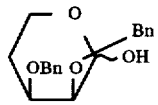

Step (3'): Compound 66 is reacted with 1,3-propanedithiol in the presence of boron trifluoride-ethyl ether to cleave the sugar ring of Compound 66, whereby there is produced 2,3-di-O-benzyl-4-deoxy-L-erythro-pentose trimethylene dithioacetal [Compound 68] of the formula

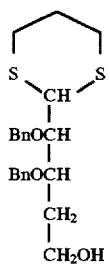

as a straight-chain compound of the dithioacetal type.

Step (4'): The primary hydroxyl group of Compound 68 is acetylated with acetic anhydride to produce 5-O-acetyl-2,3-di-O-benzyl-4-deoxy-L-erythro-pentose trimethylene dithioacetal [Compound 69] of the formula

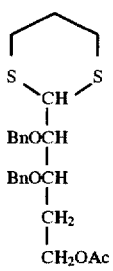

Step (5'): Compound 69 is reacted with mercury perchlorate in aqueous tetrahydrofuran in the presence of calcium carbonate to cleave the dithioacetal ring of Compound 69, whereby there is produced 5-O-acetyl-2,3-di-O-benzyl-4-deoxy-aldehyde-L-erythro-pentose [Compound 70] of the formula

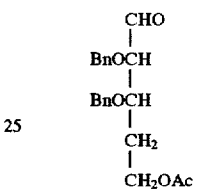

as an aldehyde-type compound.

Step (6'): Compound 70 is then reacted with trifluoromethyltrimethylsilane in anhydrous tetrahydrofuran in the presence of tetrabutylammonium fluoride. Thereby, there are produced 6-O-acetyl-3,4-di-O-benzyl-1,5-dideoxy-1,1,1-trifluoro-L-arabino-hexitol [Compound 71] of the formula

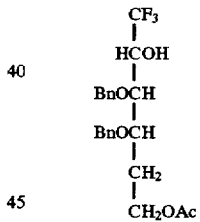

as an L-arabino-hexitol derivative having a trifluoromethyl group incorporated therein and its 2-epimer [Compound 72] of the formula:

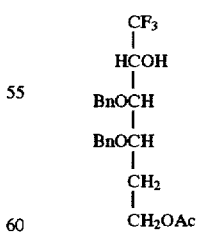

Step (7'): Compound 71 is treated with a methanolic solution of sodium methoxide to remove the acetyl group from Compound 71. There is thus produced 3,4-di-O-benzyl-1,5-dideoxy-1,1,1-trifluoro-L-arabino hexitol [Compound 73] of the formula

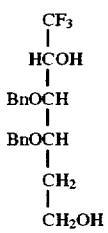

as a diol.

Step (8'): Reactions of oxidizing selectively the primary hydroxyl group of Compound 73 and forming simultaneously the ring of a pyranose are then conducted. For this purpose, the 2- and 6-hydroxyl groups of Compound 73 are trimethylsilylated, followed by effecting Collin's oxidation of the resulting trimethylsilylated product. Thus, the primary trimethylsilyloxy group of the resulting trimethylsilylated product is subjected to selective oxidation to afford an aldehyde product. This aldehyde product is then hydrolyzed with acid to remove the remaining trimethylsilyl group and concurrently bring about the cyclization reaction, whereby there is produced 3,4-di-O-benzyl-2,6-dideoxy-6,6,6-trifluoro-L-lyxo-hexopyranose [Compound 74] of the formula

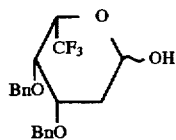

as a 2,6-dideoxy-6,6,6-trifluoro-L-lyxo-hexopyranose derivative.

Step (9'): The 1-hydroxyl group of Compound 74 is then acetylated with acetic anhydride to produce 1-O-acetyl-3,4-di-O-benzyl-2,6-dideoxy-6,6,6-trifluoro-L-lyxo-hexopyranose [Compound 75] of the formula

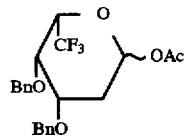

Step (10'): The benzyl groups at the 3- and 4-positions of Compound 75 are removed therefrom by catalytic reduction to produce 1-O-acetyl-2,6-dideoxy-6,6,6-trifluoro-L-lyxo-hexopyranose [Compound 76] of the formula

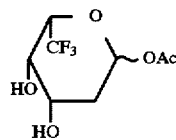

Step (11'): The hydroxyl groups at the 3- and 4-positions of Compound 76 are acetylated with acetic anhydride, whereby there is produced 1,3,4-tri-O-acetyl-2,6-dideoxy-6,6,6-trifluoro-L-lyxo-hexopyranose [Compound 77] of the formula

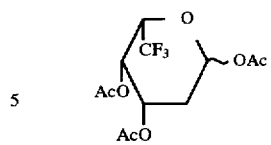

as a tri-O-acetylated product. When this Compound 77 is subjected to a silica gel column chromatograpehy as developed with dichloromethane, Compound 77 can be isolated separately into the α-anomer [Compound (77-a)] and the β-anomer [Compound (77-b)].

Step (12'): Compound 77 (the mixture of the aforesaid anomers) is brominated in its solution in hydrogen bromide-acetic acid by a conventional method, whereby there is obtained 3,4-di-O-acetyl-2,6-dideoxy-6,6,6-trifluoro-α-L-lyxo-hexopyranosyl bromide [Compound 78 of the formula

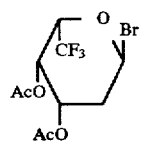

as a 1-bromo sugar. While, when Compound 77 is reacted with iodotrimethylsilane in anhydrous toluene, there is produced a corresponding 1-iodo sugar.

The adriamycinone derivative of the aforesaid formula (D) may also be prepared by such a method which comprises condensing the 7-hydroxyl group of the aforesaid 14-O-TBS-adriamycinone with the above Compound 78, namely 3,4-di-O-acetyl-2,6-dideoxy-6,6,6-trifluoro-α-L-lyxo-hexopyranosyl bromide in the same manner as described in the foregoing item (J), and then removing the hydroxyl-protecting TBS group from the resulting condensation product.

Next, descriptions are made of Referential Example 1 and Referential Example 2 which illustrate the synthesis of the aforesaid 2,6-dideoxy-2,6,6,6-tetrafluoro-α-L-talopyranose derivatives and the synthesis of the aforesaid 2,6-dideoxy-6,6,6-trifluoro-L-lyxo-hexopyranose derivatives, respectively, as well as Referential Example 3 and referential Example 4 which illustrate the synthesis of the aforesaid new adriamycinone derivative of the formula (C-b) and the synthesis of the aforesaid new adriamycinone derivative of the formula (D), respectively. In these Referential Examples 1 to 4, Bn denotes benzyl group and Ac denotes acetyl group in the different formulae shown therein.

REFERENTIAL EXAMPLE 1

(1) Preparation of methyl 4-deoxy-4-fluoro-β-L-ribopyranoside (Compound 51)

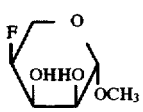

Methyl α-D-lyxopyranoside (Compound 50) (see F. P. Phelps et. al. "Journal of American Chemical Society" Vol. 48, pp. 503–507, 1926) (8.27 g) was suspended in anhydrous dichloromethane (167 ml) and the suspension was cooled to −40° C. To the suspension was added diethyl aminosulfur trifluoride (26.8 ml), and then the reaction mixture was stirred at room temperature for 1 hour to conduct the fluorination reaction.

The resulting reaction solution was cooled to −20° C., to which methanol (170 ml) was added and the resulting mixture was stirred at room temperature for 15 hours. The reaction solution was neutralized with addition of sodium hydrogen carbonate (105 g) and the insoluble matters was removed by filtration. The filtrate was concentrated under a reduced pressure and the residue so obtained was purified by a silica gel column chromatography (developer: chloroform-acetone, 7:1), affording the titled Compound 51 as a syrup (7.54 g, yield 90%).

$^1$H-NMR spectrum (in deutero-chloroform):
δ4.79 (1H, d, H-1)
4.74 (1H, br d, H-4)
3.42 (3H, s, OCH$_3$)

$^{19}$F-NMR spectrum (in deutero-chloroform, CFCl$_3$ as internal standard):
δ−203.0 (ddddd, $J_{3,F}$=30, $J_{4,F}$=49, $J_{5ax,F}$=38, $J_{5eq,F}$=15.5, $J_{F,OH-2}$=8 Hz)

(2) Preparation of methyl 2,3-di-O-benzyl-4-deoxy-4-fluoro-β-L-ribopyranoside (Compound 52)

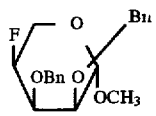

Compound 51 obtained in the above item (1) (7.44 g) was dissolved in anhydrous N,N-dimethylformamide (DMF) (72 ml), to which was then added a 60% sodium hydride (9.4 g) in oil. The mixture was stirred at room temperature for 1 hour. To the reaction mixture was added benzyl bromide (16 ml) under ice-cooling, and the resulting mixture was tirred at room temperature for 2 hours to conduct the O-benzylation.

The reaction solution was poured into a 3% aqueous acetic acid solution (500 ml) and the resulting mixture was extracted with chloroform. The chloroform solution obtained was washed with a saturated aqueous sodium hydrogen carbonate solution and a saturated aqueous sodium chloride solution in order. Thereafter, the solution thus washed was dried over anhydrous sodium sulfate and concentrated under a reduced pressure. The resulting residue was purified by a silica gel column chromatography (developer: toluene-ethyl acetate, 30:1), affording the titled compound 52 as a syrup (12.61 g, yield 81%).

$^1$H-NMR spectrum (in deutero-chloroform):
δ7.2–7.4 (10H, m, aromatic proton)
4.74 (1H, d, H-1)
4.66 (1H, ddt, H-4)
3.40 (3H, s, OCH$_3$)

$^{19}$F-NMR spectrum (in deutero-chloroform, CFCl$_3$ as internal standard):
δ−202.3 (dddd, $J_{3,F}$=23.5, $J_{4,F}$=48.5, $J_{5ax,F}$=24, $J_{5eq,F}$=10 Hz)

(3) Preparation of 2,3-di-O-benzyl-4-deoxy-4-fluoro-L-ribopyranose (compound 53)

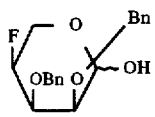

Compound 52 obtained in the above item (2) (3.06 g) was dissolved in 0.4N hydrogen chloride-80% aqueous acetic acid solution (31 ml), and the solution was allowed to stand at 80° C. for 3.5 hrs. to conduct the reaction (for the cleavage of the glycoside linkage by hydrolysis).

The resulting reaction solution was poured into water (200 ml) containing sodium hydrogen carbonate (38 g), and the mixture thus obtained was extracted with chloroform. Then, the chloroform solution obtained was washed with a saturated aqueous sodium hydrogen carbonate solution and a saturated aqueous sodium chloride solution in order. The solution thus washed was dried over anhydrous sodium sulfate and the dried solution was concentrated under a reduced pressure. The resulting residue was purified by a silica gel column chromatography (developer: hexane-ethyl acetate, 5:2), thus yielding the titled Compound 53 which was a mixture of α-anomer and β-anomer as a syrup (2.58 g, yield 88%).

$^{19}$F-NMR spectrum (in deutero-chloroform):
δ−202.6 (dddd, F-4 of β-anomer)
−199.2 (br d, F-4 of α-anomer)

(4) Preparation of 2,3-di-O-benzyl-4-deoxy-4-fluoro-L-ribose trimethylene dithioacetal (Compound 54)

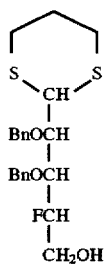

Compound 53 obtained in the item (3) (4.12 g) was dissolved in anhydrous dichloromethane (76 ml). To the solution were added 1,3-propanedithiol (2.1 ml) and boron trifluoride-diethyl ether (0.53 ml). The resulting reaction mixture was stirred at room temperature for 2 hrs. to conduct the reaction.

The reaction solution was diluted with chloroform, washed with a 5% aqueous sodium hydroxide solution and water in order and dried over anhydrous sodium sulfate. The solution thus dried was concentrated under a reduced pressure. The resulting residue was purified by a silica gel column chromatography (developer: toluene-ethyl acetate, 12:1→4:1, by gradient method), thus giving the titled compound 54 as a syrup (3.92 g, yield 75%).

$^1$H-NMR spectrum (in deutero-chloroform):
δ4.42 (1H, d, H-1)
2.5–2.9 (4H, m, thioacetal)
2.0–2.15 (1H, m, thioacetal)
1.8–2.0 (1H, m, thioacetal)

$^{19}$F-NMR spectrum (in deutero-chloroform, CFCl$_3$ as internal standard):
δ−195.6 (ddt, $J_{3,F}$=14, $J_{4,F}$=46, $J_{5a,F}$=$J_{5b,F}$=24 Hz)

(5) Preparation of 5-O-acetyl-2,3-di-O-benzyl-4-deoxy-4-fluoro-L-ribose trimethylene dithioacetal (Compound 55)

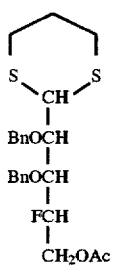

Compound 54 obtained in the item (4) (2.40 g) and acetic anhydride (2.7 ml) were dissolved in anhydrous pyridine (24 ml) and the solution was allowed to stand at room temperature for 3 hrs. to conduct the O-acetylation reaction.

The reaction solution was poured into water (250 ml) and the mixture was stirred for 1.5 hrs. and then extracted with chloroform. The resulting chloroform solution was washed with a 20% aqueous potassium hydrogen sulfate solution, a saturated aqueous sodium hydrogen carbonate solution and water in order. Then, the solution thus washed was dried over anhydrous sodium sulfate and concentrated under a reduced pressure, thereby yielding the titled Compound 55 as a syrup (2.64 g) which was a quantitative yield.

$^1$H-NMR spectrum (in deutero-chloroform):

δ4.2–4.4 (2H, m, H-5a, 5b)
2.05 (3H, s, OAc)

$^{19}$F-NMR spectrum (in deutero-chloroform, CFCl$_3$ as internal standard):
δ–193.0 (dddd).

(6) Preparation of 5-O-acetyl-2,3-di-O-benzyl-4-deoxy-4-fluoro-aldehyde-L-ribose (Compound 56)

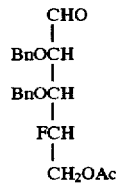

Compound 55 obtained in the item (5) (2.58 g) was dissolved in a mixture (34 ml) of tetrahydrofuran (THF)-water (10:3). To the solution was added a THF solution (20 ml) of calcium carbonate (10.24 g) and mercury perchlorate trihydrate (6.01 g). The mixture was stirred at room temperature for 2 hrs. To the reaction solution was further added a THF solution (6 ml) of mercury perchlorate trihydrate (0.57 g), and the resultant mixture was stirred for 30 minutes to conduct the oxidation reaction.

The resulting reaction mixture was filtered to remove insoluble matters and the filtrate was diluted with dichloromethane. A saturated aqueous sodium hydrogen carbonate solution was added to the resulting dichloromethane solution and the mixture was vigorously shaked. The insoluble matters so deposited were removed by filtration. Thereafter, the filtrate was washed with a 10% aqueous potassium iodide solution and water in order, dried over anhydrous sodium sulfate and then concentrated under a reduced pressure, thus affording the titled Compound 56 as a syrup (1.92 g, yield 92%).

$[\alpha]_D^{23}$–62° (c 1, chloroform)

$^1$H-NMR spectrum (in deutero-chloroform):

δ9.65 (1H, br d, H-1)
2.01 (3H, s, OAc)

$^{19}$F-NMR spectrum (in deutero-chloroform, CFCl$_3$ as internal standard:
δ–194.7 (ddddd, J$_{1,F}$=4, J$_{3,F}$=6, J$_{4,F}$=46, J$_{5a,F}$=29, J$_{5b,F}$=26 Hz).

(7) Preparation of 6-O-acetyl-3,4-di-O-benzyl-1,5-dideoxy-1,1,1,5-tetrafluoro-L-altritol (Compound 57)

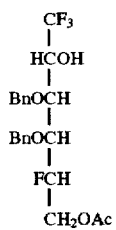

Compound 56 obtained in the item (6) (1.87 g) and trifluoromethyltrimethylsilane (1.2 ml) were dissolved in anhydrous THF (15 ml), to which was added a THF solution (3.6 ml) of tetrabutylammonium fluoride trihydrate (160 mg) under ice cooling. The resulting mixture was allowed to stand at room temperature for 1 hour (for the introduction reaction of trifluoromethyl group).

After concentrating, the reaction solution was diluted with chloroform, and the diluted solution was washed with water, dried over anhydrous sodium sulfate and concentrated under a reduced pressure. The syrup thus obtained was dissolved in an 80% aqueous acetic acid (20 ml) and the solution was allowed to stand at 50° C. for 3 hrs, whereby the trimethylsilyloxy group as formed during the above-mentioned reaction was converted into hydroxyl group. The resulting reaction solution was concentrated under a reduced pressure to leave a residue which was then subjected to a silica gel column chromatography (developer: toluene-ethyl acetate, 30:1) for the isolation and purification of the desired compound. There were thus obtained the titled Compound 57 (0.65 g, yield 29%) and its 2-epimer (Compound 58 (0.87 g, yield 39%) each as a syrup.

$[\alpha]_D^{19}$–21° (c 1.4, chloroform)

$^1$H-NMR spectrum (in deutero-chloroform):

δ4.92 (1H, ddt, H-5)
4.17 (1H, dq, H-2)
2.08 (3H, s, OAc)

$^{19}$F-NMR spectrum (in deutero-chloroform, CFCl$_3$ as internal standard):
δ–193.3 (1F, m, F-5)
–77.0 (3F, d, CF$_3$).

(8a) Preparation of 3,4-di-O-benzyl-1,5-dideoxy-1,1,1,5-tetrafluoro-L-altritol (Compound 59)

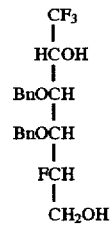

Compound 57 obtained in the item (7), i.e. 6-O-acetyl-3,4-di-O-benzyl-1,5-dideoxy-1,1,1,5-tetrafluoro-L-altritol, (0.62 g) was dissolved in a methanolic solution (17 ml) of 0.02N sodium methoxide. The solution obtained was allowed to stand at room temperature for 20 minutes to conduct the reaction for elimination of O-acetyl group.

After neutralizing the reaction solution by addition of a strongly acidic ion exchange resin, Dowex 50W (H$^+$ type), to the solution, the resin was filtered off and the filtrate was concentrated under a reduced pressure. The resulting residue was recrystallized from chloroform-hexane to afford the titled Compound 59 as needles (0.52 g, yield 93%).

Melting point 64°–65° C.

$[\alpha]_D^{23}$ −29° (c 1, chloroform)

(8b) Preparation of 1,5-dideoxy-1,1,1,5-tetrafluoro-L-altritol (Compound 59')

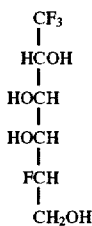

Compound 59 obtained in the item (8a), i.e. 3,4-di-O-benzyl-1,5-dideoxy-1,1,1,5-tetrafluoro-L-altritol (0.11 g) was dissolved in a mixture of dioxane-acetic acid-water (10:1:1) (3 ml), to which palladium black was added and then hydrogen gas was blown into the solution to effect the catalytic reduction for 3 hrs.

The reaction mixture was filtered and the filtrate was concentrated under a reduced pressure, yielding the titled Compound 59' as a solid, quantitatively (0.06 g).

$^{19}$F-NMR spectrum (in deutero-methanol, CFCl$_3$ as internal standard):

δ−195 (1F, F-5)
−77 (3F, CF$_3$)

(9) Preparation of 3,4-di-O-benzyl-2,6-dideoxy-2,6,6,6-tetrafluoro-α-L-talopyranose (Compound 60)

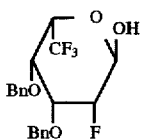

Compound 59 obtained in the item (8a) (0.73 g), chlorotrimethylsilane (1.4 ml) and 4-dimethylaminopyridine (0.12 g) were dissolved in anhydrous pyridine (7 ml). The resulting solution was allowed to stand at room temperature for 15 hrs. to effect the trimethylsilylation reaction of the 2- and 6-hydroxyl groups. The reaction solution obtained was diluted with ethyl acetate, washed with water, dried over anhydrous sodium sulfate and then concentrated under a reduced pressure, affording 2,6-di-O-trimethylsilylated product as a syrup (994 mg).

The next step was to conduct the selective oxidation reaction of the 6-trimethylsilyloxy group. Thus, anhydrous chromic acid (1.29 g) was suspended in a mixture of anhydrous dichloromethane (36 ml) and anhydrous pyridine (2.2 ml) and the suspension was stirred at room temperature for 30 minutes. The reddish yellow liquid so obtained was cooled with ice. To the ice-cooled liquid was added a dichloromethane solution (5 ml) of the above-mentioned syrup, and the mixture obtained was stirred under ice-cooling for 2 hrs. The resulting reaction mixture was filtered through a short column packed with silica gel. The column was washed with ethyl acetate and the eluate from the column was concentrated under a reduced pressure to give a syrup (0.68 g).

Then, in order to remove the remaining trimethylsilyl group and to cause the cyclization reaction, the resulting syrup (0.68 g) was dissolved in a mixture (8 ml) of dioxane and water (9:1) containing 0.1N hydrogen chloride. The resulting solution was allowed to stand at room temperature for 1.5 hrs. to conduct the reaction. To the reaction solution was added a saturated aqueous solution of sodium hydrogen carbonate, and the resulting mixture was extracted with dichloromethane. The dichloromethane solution so obtained was washed with water, dried over anhydrous sodium sulfate and then concentrated under a reduced pressure, affording the titled Compound 60 as a syrup (0.48 g, yield 64%).

$^1$H-NMR spectrum (in deutero-chloroform):

δ5.55 (1H, br d, H-1)
4.72 (1H, br d, H-2)

$^{19}$F-NMR spectrum (in deutero-chloroform-heavy water, CFCl$_3$ as internal standard):

δ−203.5 (1F, ddd, F-2, $J_{1,F}$=9, $J_{2,F}$=49 $J_{3,F}$=32 Hz), −73.5 (3F,d, CF$_3$)

(10) Preparation of 1-O-acetyl-3,4-di-O-benzyl-2,6-dideoxy- 2,6,6,6-tetrafluoro-α-L-talopyranose (Compound 61)

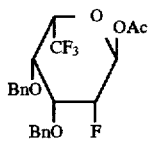

Compound 60 obtained in the item (9) (0.48 g) and acetic anhydride (0.56 ml) were dissolved in anhydrous pyridine (10 ml), and the resulting solution was allowed to stand at room temperature for 40 minutes to conduct the acetylation.

Water (0.6 ml) was added to the resulting reaction solution and the resultant mixture was concentrated to a half volume under a reduced pressure and then diluted with chloroform. The diluted solution was washed successively with a 20% aqueous potassium hydrogen sulfate solution, a saturated aqueous sodium hydrogen carbonate solution and water. Then, the solution was dried over anhydrous sodium sulfate and concentrated under a reduced pressure, to afford the titled Compound 61 as a syrup (0.47 g, yield 87%).

$^1$H-NMR spectrum (in deutero-chloroform):

δ6.46 (1H, dd, H-1)
4.69 (1H, ddt, H-2)
2.08 (3H, s, OAc)

(11) Preparation of 1-O-acetyl-2,6-dideoxy-2,6,6,6-tetrafluoro-α-L-talopyranose (Compound 62)

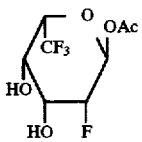

Compound 61 obtained in the item (10) (0.47 g) was dissolved in a mixture of dioxane-acetic acid-water (10:1:1) (15 ml). To the solution was added palladium black and then hydrogen gas was blown into the solution to conduct the catalytic reduction of Compound 61 for 4.5 hrs.

The reaction solution obtained was filtered and the filtrate was concentrated under a reduced pressure to yield Compound 62 quantitatively as a solid (0.28 g).

$^1$H-NMR spectrum (in deutero-chloroform):

δ6.21 (1H, dd, H-1)
4.50 (1H, dddd, H-2)
2.03 (3H, s, OAc)

(12) Preparation of 1,3,4-tri-O-acetyl-2,6-dideoxy-2,6,6,6-tetrafluoro-α-L-talopyranose (Compound 63)

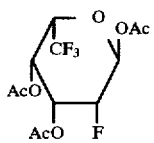

Compound 62 obtained in the item (11) (0.27 g) and acetic anhydride (1 ml) were dissolved in anhydrous pyridine (5 ml), and the solution was allowed to stand at room temperature for 20 hrs. to effect the O-acetylation reaction.

Post treatment of the reaction solution was carried out in the same manner as in Referential Example 1 (10), whereby the titled Compound 63 was obtained as a syrup (0.32 g, yield 89%).

$^1$H-NMR spectrum (in deutero-chloroform):
δ6.48 (1H, br d, H-1)
5.67 (1H, br d, H-4)
5.19 (1H, dt, H-3)
2.18, 2.15, 2.12 (each 3H, s, OAc)

(13) Preparation of 3,4-di-O-acetyl-2,6-dideoxy-2,6,6,6-tetrafluoro-L-talopyranosyl iodide (Compound 64)

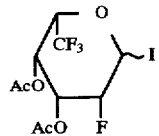

Compound 63 obtained in the item (12), i.e. 1,3,4-tri-O-acetyl-2,6-dideoxy-2,6,6,6-tetrafluoro-α-L-talopyranose (195 mg) was dissolved in anhydrous toluene (4 ml). To the solution was added iodotrimethylsilane (0.5 ml), and the resultant mixture was allowed to stand in a dark place at 80° C. for 15 hrs. to conduct the iodination reaction.

The reaction solution so obtained was diluted with toluene, washed with a 10% aqueous sodium thiosulfate solution, a saturated aqueous sodium hydrogen carbonate solution and water in order. The reaction solution so washed was dried over anhydrous sodium sulfate and concentrated under a reduced pressure. The residue obtained was purified by a flash silica gel column chromatography (developer: hexane-ethyl acetate, 6:1), to give the titled Compound 64 as a syrup (132 mg, yield 58%).

$^1$H-NMR spectrum (in deutero-chloroform):
δ7.01 (1H, br d, H-1)
2.14, 2.11 (each 3H, s, OAc)

$^{19}$F-NMR spectrum (in deutero-chloroform, CFCl$_3$ as internal standard):
δ–173.6 (1F, ddd, F-2)
–73.8 (3F, d, CF$_3$)

REFERENTIAL EXAMPLE 2

(1) Preparation of methyl 2,3-di-O-benzyl-4-deoxy-β-L-erythro-pentopyranoside (Compound 66)

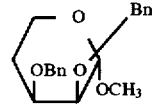

A 60% sodium hydride (7.7 g) in oil was suspended in anhydrous N,N-dimethylformamide (DMF) (13 ml). To the suspension was added methyl 4-deoxy-β-L-erythro-pentopyranoside (Compound 65) (P. W. Kent and P. F. V. Ward, "Journal of the Chemical Society" pp. 416–418,
1953) (5.63 g) in an anhydrous DMF solution (20 ml). After the resulting mixture was stirred at room temperature for 50 minutes, benzyl bromide (13.6 ml) was added under ice-cooling, and the mixture so obtained was further stirred at room temperature for 40 minutes to conduct the reaction (for O-benzylation).

To the resulting reaction solution, acetic acid (13.6 ml) and then water (300 ml) were added, and the solution thus diluted was extracted with chloroform. The chloroform solution obtained was washed with a saturated aqueous sodium hydrogen carbonate solution and water, successively, and then dried over anhydrous sodium sulfate and concentrated under a reduced pressure. Xylene was added to the resulting residue and the resulting solution was concentrated under a reduced pressure. Repetition of this step was made for the removal of DMF. The residue so obtained was purified by a silica gel column chromatography (developer: toluene-acetone, 30:1), to afford the titled Compound 66 as a syrup (10.1 g, yield 81%).

$[\alpha]_D^{23}$+35° (c 1.9, chloroform)

Elemental analysis (for C$_{20}$H$_{24}$O$_4$): Calculated: C, 73.15; H, 7.37% Found: C, 73.08 ; H, 7.24%

(2) Preparation of 2,3-di-O-benzyl-4-deoxy-L-erythro-pentopyranose (Compound 67)

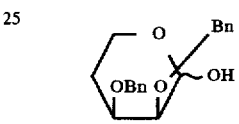

Compound 66 obtained in the above item, (1) i.e. methyl 2,3-di-O-benzyl-4-deoxy-β-L-erythro-pentopyranoside (4.81 g) was dissolved in a mixture (48 ml) of 2N hydrochloric acid-acetic acid (1:4), and the solution obtained was allowed to stand at 80° C. for 40 minutes to effect the hydrolysis (for the cleavage of the glycoside bond).

The resulting reaction solution was poured into water (400 ml) containing sodium hydrogen carbonate (74 g), and the mixture obtained was extracted with chloroform. The chloroform solution thus obtained was washed with a saturated sodium hydrogen carbonate solution and water, successively, and then dried over anhydrous sodium sulfate and concentrated under a reduced pressure. The resulting residue was purified by a silica gel column chromatography (developer: toluene-acetone, 12:1). The titled Compound 67 was obtained in the form of a mixture of α-anomer and β-anomer as a syrup (3.78 g, yield 82%).

$^1$H-NMR spectrum (in deutero-chloroform):
δ5.07 (0.5H, br s, H-1)
5.20 (0.5H, t, H-1 of the other anomer)

(3) Preparation of 2,3-di-O-benzyl-4-deoxy-L-erythro-pentose trimethylene dithioacetal (Compound 68)

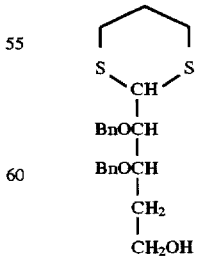

Compound 67 obtained in the item (2), i.e. 2,3-di-O-benzyl-4-deoxy-L-erythro-pentopyranose (10.28 g) was dissolved in anhydrous dichloroethane (60 ml). To the solution were added 1,3-propanedithiol (5.9 ml) and boron trifluoride-diethylether (1.2 ml). The resulting reaction mixture was stirred at 60° C. for 3.5 hrs. to conduct the reaction. The reaction solution thus obtained was diluted with chloroform, washed with a 5% aqueous sodium hydroxide solution and water, successively, and then dried over anhydrous sodium sulfate and concentrated under a reduced pressure. The resulting residue was purified by a silica gel column chromatography (developer: toluene-acetone, 12:1), to yield the titled Compound 68 as a syrup (8.50 g, yield 64%).

$[\alpha]_D^{25}$ –39° (c 1, chloroform)

Elemental analysis (for $C_{22}H_{28}O_3S_2$): Calculated: C, 65.41 ; H, 6.98 ; S, 15.85% Found: C, 65.41 ; H, 6.95 ; S, 15.78%

(4) Preparation of 5-O-acetyl-2,3-di-O-benzyl-4-deoxy-L-erythropentose trimethylene dithioacetal (Compound 69)

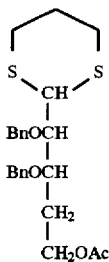

Compound 68 obtained in the item (3), i.e. 2,3-di-O-benzyl-4-deoxy-L-erythro-pentose trimethylene dithioacetal (1.03 g) and acetic anhydride (0.4 ml) were dissolved in anhydrous pyridine (8 ml), and the solution thus obtained was allowed to stand at room temperature for 23 hrs. to effect the O-acetylation. Then, water (0.4 ml) was added to the reaction solution, and the mixture was allowed to stand for 2 hrs. and then concentrated under a reduced pressure.

To the residue obtained was added a 20% aqueous potassium hydrogen sulfate solution, and the mixture was extracted with chloroform. The chloroform solution obtained was washed with a saturated aqueous sodium hydrogen carbonate solution and water, successively, and then dried over anhydrous sodium sulfate and concentrated under a reduced pressure, to afford the titled Compound 69 as a syrup (1.09 g, yield 97%).

$[\alpha]_D^{21}$ –38° (c 0.7, chloroform)

$^1$H-NMR spectrum (in deutero-chloroform):
δ1.98 (3H, s, OAc)

(5) Preparation of 5-O-acetyl-2,3-di-O-benzyl-4-deoxy-aldehyde-L-erythro-pentose (Compound 70)

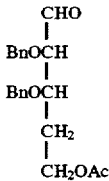

Compound 69 obtained in the item (4) above, i.e. 5-O-acetyl-2,3-di-O-benzyl-4-deoxy-L-erythro-pentose trimethylene dithioacetal (1.09 g) was dissolved in a mixture (15 ml) of tetrahydrofuran (THF)-water (10:3). To the resultant solution were added calcium carbonate (4.7 g) and a THF solution (9 ml) of mercury perchlorate trihydrate (2.9 g). The resultant the mixture was stirred at room temperature for 1 hour.

The reaction solution was diluted with addition of dichloromethane (50 ml) and a saturated aqueous sodium hydrogen carbonate solution (20 ml), and the mixture obtained was filtered through Celite to remove insoluble matters to obtain the filtrate. The residue was further washed with dichloromethane three times (30 ml each) and the washings were combined with the filtrate above.

The solution combined was washed with a saturated sodium hydrogen carbonate solution (10 ml) added. The dichloromethane solution thus obtained was washed with a 10% aqueous potassium iodide solution and water, in order, and then dried over anhydrous sodium sulfate and concentrated under a reduced pressure, to yield the titled Compound 70 (0.87 g), quantitatively.

$[\alpha]_D^{20}$ –71° (c 1, chloroform)

$^1$H-NMR spectrum (in deutero-chloroform):
δ9.71 (1H, d, CHO)

(6) Preparation of 6-O-acetyl-3,4-di-O-benzyl-1,5-dideoxy-1,1,1-trifluoro-L-arabino-hexitol (Compound 71)

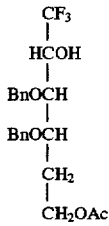

Compound 70 obtained in the item (5) above, i.e. 5-O-acetyl-2,3-di-O-benzyl-4-deoxy-aldehyde-L-erythro-pentose (0.81 g) and trifluoromethyltrimethylsilane (0.5 ml) were dissolved in THF (8 ml), to which was then added a THF solution (2 ml) of tetrabutylammonium fluoride trihydrate (71 mg) under ice-cooling. The resulting mixture was allowed to stand at room temperature for 1.5 hrs. to conduct the reaction (for the introduction of trifluoromethyl group).

The reaction soution was concentrated under a reduced pressure and was diluted with chloroform, washed with water, dried over anhydrous sodium sulfate and concentrated under a reduced pressure. The resulting syrup was dissolved in an 80% aqueous acetic acid (4 ml) and the solution was allowed to stand at 50° C. for 1.5 hrs. so that the 2-trimethylsilyloxy group as formed during the above reaction was converted into hydroxyl group. The resulting reaction solution was concentrated under a reduced pressure and the residue thus obtained was subjected to a silica gel column chromatography (developer: toluene-ethyl acetate, 25:1) for the purpose of separation and purification, to afford the titled (Compound 71) (0.36 g, yield 37%) and 2-epimer thereof (Compound 72) (0.36 g, yield 37%), respectively, as a syrup.

$[\alpha]_D^{24}$ –24° (c 1, chloroform)

$^{19}$F-NMR spectrum (in deutero-chloroform, CFCl$_3$ as internal standard):

δ–77.6 (d, CF$_3$)

(7) Preparation of 3,4-di-O-benzyl-1,5-dideoxy-1,1,1-trifluoro-L-arabino-hexitol (Compound 73)

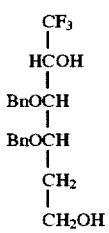

```
    CF₃
    |
   HCOH
    |
   BnOCH
    |
   BnOCH
    |
    CH₂
    |
   CH₂OH
```

Compound 71 obtained in the item (6) above, i.e. 6-O-acetyl-3,4-di-O-benzyl-1,5-dideoxy-1,1,1-trifluoro-L-arabino-hexitol (296 mg) was dissolved in a methanolic solution (5 ml) of 0.025N sodium methoxide. The resulting solution was allowed to stand at room temperature for 1 hour to effect the elimination of the O-acetyl group. The reaction solution obtained was neutralized with addition of a strongly acidic ion exchange resin, Dowex 50W (H⁺ form),thereto, and the resin used was filtered off. The resulting filtrate was concentrated under a reduced pressure, to afford the titled Compound 73 as a syrup (266 mg, yield 99%).

$[\alpha]_D^{21} -17°$ (c 0.7, chloroform)

¹⁹F-NMR (deutero-chloroform, CFCl₃ as internal standard):

δ-75.7 (d, CF₃)

(8) Preparation of 3,4-di-b-benzyl-2,6-dideoxy-6,6,6-trifluoro-L-lyxo-hexopyranose (Compound 74)

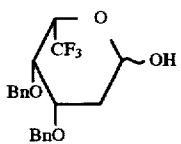

Compound 73 obtained in the item (7) above, i.e. 3,4-di-O-benzyl-1,5-dideoxy-1,1,1-trifluoro-L-arabinohexitol (1.46 g), chlorotrimethylsilane (1.7 ml) and 4-dimethylaminopyridine (0.18 g) were dissolved in anhydrous pyridine (15 ml). The resulting solution was allowed to stand at room temperature for 15 hrs. to effect the trimethylsilylation of the 2- and 6-hydroxyl groups. The resulting reaction solution was concentrated under a reduced pressure, and the concentrate obtained was diluted with ethyl acetate and washed with water. The solution so washed was dried over anhydrous sodium sulfate and concentrated under a reduced pressure, to afford the 2,6-di-O-trimethylsilylated product as a syrup (2.07 g).

The next step was to carry out the selective oxidation reaction of the 6-trimethylsilyloxy group of the trimethylsilylation product obtained as above. Thus, anhydrous chromic acid (1.82 g) suspended in a mixture of anhydrous dichloromethane (25 ml) and anhydrous pyridine (3 ml), and the resulting suspension was stirred at room temperature for 30 minutes. The resulting red liquid was cooled with ice, to which was added a dichloromethane solution (3.5 ml) of the syrupy trimethylsilylated product above. The mixture was stirred under ice-cooling for 40 minutes. The resulting reaction solution was diluted with ethyl acetate and filtered through a glass filter packed with silica gel to obtain the filtrate. The filter used was washed with ethyl acetate, and said filtrate and the washings were combined together and the mixture was concentrated under a reduced pressure. To the residue was added ethyl acetate, and the resulting insoluble matters were filtered and washed in the same manner as above. The resulting filtrate and washings were combined and the mixture was concentrated under a reduced pressure, thus yielding a syrup (1.83 g) which was an aldehyde.

The next step was to remove the remaining trimethylsilyl group and also to effect the cyclization reaction. Thus, the syrup obtained as above (1.83 g) was dissolved in a mixture (18 ml) of dioxane-water (10:1) (18 ml) containing 0.1N hydrogen chloride. The resultant solution was allowed to stand at room temperature for 50 minutes to conduct the reaction. To the reaction solution was added a saturated aqueous sodium hydrogen carbonate solution (60 ml), and the mixture was extracted with dichloromethane. The resulting dichloromethane solution was washed with water, dried over anhydrous sodium sulfate and concentrated under a reduced pressure, to afford the titled Compound 74 as a syrup (1.42 g, yield 98%).

$[\alpha]_D^{21} -72°$ (c 0.23, chloroform)

(as determined at a time of 24 hours after the sample was dissolved in chloroform)

¹H-NMR spectrum (in deutero-chloroform):

δ5.54 (br, d, H-1 of α-anomer)

¹⁹F-NMR spectrum (in deutero-chloroform, CFCl₃ as internal standard):

δ-74.0 (-2.7F, CF₃ of α-anomer)

-73.6 (-0.3F, CF₃ of β-anomer)

(9) Preparation of 1-O-acetyl-3,4-di-O-benzyl-2,6-dideoxy-6,6,6-trifluoro-L-lyxo-hexopyranose (Compound 75)

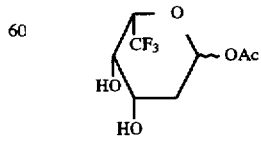

Compound 74 obtained in the item (8) above, i.e. 3,4-di-O-benzyl-2,6-dideoxy-6,6,6-trifluoro-L-lyxo-hexopyranose (1.34 g) and acetic anhydride (0.5 ml) were dissolved in anhydrous pyridine (10 ml), and the solution was allowed to stand at room temperature for 2.5 hrs. to conduct the acetylation.

Water (0.5 ml) was added to the resulting reaction solution and the mixture obtained was concentrated under a reduced pressure. The residue was diluted with chloroform and the resulting solution was washed with a 20% aqueous potassium hydrogen sulfate solution, a saturated aqueous sodium hydrogen carbonate solution and water, in order. The resulting solution so washed was dried over anhydrous sodium sulfate and concentrated under a reduced pressure, to afford the titled Compound 75, in the form of a mixture of α-anomer and β-anomer, as a syrup (1.31 g, yield 88%).

¹H-NMR spectrum (in deutero-chloroform):

δ2.07, 2.11 (3H in combination, each s, OAc)

5.71 (-0.3H, dd, H-1 of β-anomer)

6.38 (-0.7H, br d, H-1 of α-anomer)

¹⁹F-NMR spectrum (in deutero-chloroform, CFCl₃ as internal standard):

δ-74.1 (d, CF₃ of α-anomer)

-73.5 (d, CF₃ of β-anomer)

(10) Preparation of 1-O-acetyl-2,6-dideoxy-6,6,6-trifluoro-L-lyxo-hexopyranose (Compound 76)

Compound 75 obtained in the item (9) above, i.e. 1-O-acetyl-3,4-di-O-benzyl-2,6-dideoxy-6,6,6-trifluoro-L-lyxohexopyranose (1.31 g) was dissolved in a mixture (30 ml) of dioxane-acetic acid-water (10:1:1). The solution, after the addition of palladium black thereto, was subjected to catalytic reduction by blowing hydrogen gas therein for 5 hrs. (for the debenzylation). The reaction solution obtained was filtered and the filtrate was concentrated under a reuced pressure, to afford the titled Compound 76 as a partially solidified syrup (736 mg, yield 98%).

$^1$H-NMR spectrum (in deutero-methanol):

δ5.66 (~0.3H, dd, H-1 of β-anomer)
6.15 (~0.7H, br d, H-1 of α-anomer)

$^{19}$F-NMR spectrum (in deutero-chloroform, CFCl$_3$ as internal standard):
δ−73.9 (d, CF$_3$ of α-anomer)
−73.4 (d, CF$_3$ of β-anomer)

(11) Preparation of 1,3,4-tri-O-acetyl-2,6-dideoxy-6,6,6-trifluoro-L-lyxo-hexopyranose (Compound 77)

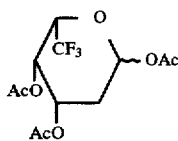

Compound 76 obtained in the item (10) above, i.e. 1-O-acetyl-2,6-dideoxy-6,6,6-trifluoro-L-lyxo-hexopyranose (0.74 g) and acetic anhydride (0.7 ml) were dissolved in anhydrous pyridine (6 ml), and the solution obtained was allowed to stand at room temperature for 20 hrs. to conduct the O-acetylation. The post-treatment of the reaction solution was carried out in the same manner as in the item (9) above, affording the titled Compound 77 in the form of a mixture of a-anomer and β-anomer, quantitatively as a syrup (1.02 g). The Compound 77 could be separated into the α-anomer (Compound 77-a) and the β-anomer (Compound 77-b) as below.

(i) α-anomer, i.e. 1,3,4-tri-O-acetyl-2,6-dideoxy-6,6,6-trifluoro-α-L-lyxo-hexopyranose (Compound 77-a):

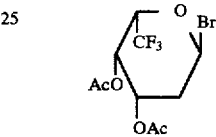

Needle crystals having melting point of 91.5°–92.5° C.

$[\alpha]_D^{19}$ −100° (c 0.6, chloroform)

$^1$H-NMR spectrum (in deutero-chloroform):

δ2.02, 2.14, 2.15 (each 3H, s, OAc)
6.44 (1H, br d, H-1)

$^{19}$F-NMR (in deutero-chloroform, CFCl$_3$ as internal standard):
δ−75.0 (d)

Elemental analysis (for C$_{12}$H$_{15}$F$_3$O$_7$): Calculated: C, 43.91 ; H, 4.61 ; F, 17.36% Found: C, 43.78 ; H, 4.67 ; F, 17.41%

(ii) β-anomer, i.e. 1,3,4-tri-O-acetyl-2,6-dideoxy-6,6,6-trifluoro-β-L-lyxo-hexopyranose (Compound 77-b):

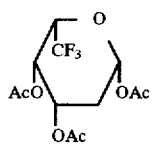

A syrup having $[\alpha]_D^{21}$ −26° (c 0.8, chloroform)

$^1$H-NMR spectrum (in deutero-chloroform):

δ2.03 (3H, s, OAc)
2.16 (6H, s, OAc×2)
5.85 (1H, dd, H-1)

$^{19}$F-NMR spectrum (in deutero-chloroform, CFCl$_3$ as internal standard):
δ−74.4 (d)

(12) Preparation of 3,4-di-O-acetyl-2,6-dideoxy-6,6,6-trifluoro-α-L-lyxo-hexopyranosyl bromide (Compound 78)

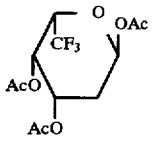

Compound 77 (the anomer mixture) as obtained in the item (11) above, i.e. 1,3,4-tri-O-acetyl-2,6-dideoxy-6,6,6-trifluoro-L-lyxo-hexopyranose (89 mg) was dissolved in a 30% hydrogen bromide-acetic acid solution (0.9 ml), and the solution obtained was allowed to stand at room temperature for 5 hrs. to conduct the bromination reaction. The reaction solution was diluted with chloroform, then washed with water, a saturated aqueous sodium hydrogen carbonate solution and water, successively, and subsequently dried over anhydrous magnesium sulfate and concentrated under a reduced pressure, to yield the titled Compound 78 as a syrup (85 mg, yield 90%)

$^1$H-NMR spectrum (in deutero-chloroform):

δ2.02, 2.14 (each 3H, s, OAc)
6.72 (1H, br d, H-1)

$^{19}$F-NMR spectrum (in deutero-chloroform, CFCl$_3$ as internal standard):
δ−74.3 (d)

Furthermore, the synthesis of the adriamycinone derivative of the formula (C-b) given hereinbefore, as well as the synthesis of the adriamycinone derivative of the formula (D) given hereinbefore are illustrated with reference to the following Referential Examples 3 and 4, respectively.

REFERENTIAL EXAMPLE 3

(1) Preparation of 7-O-(3,4-di-O-acetyl-2,6-dideoxy-2,6,6,6-tetrafluoro-α-L-talopyranosyl)-14-O-tert-butyldimethylsilyladriamycinone (Compound 79)

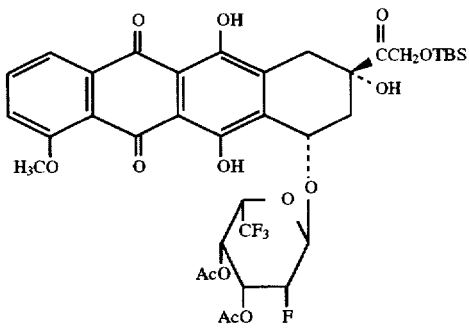

Compound 64 as obtained in Referential Example 1 (13), i.e. 3,4-di-O-acetyl-2,6-dideoxy-2,6,6,6-tetrafluoro-L-talopyranosyl iodide (105 mg), 14-O-tert-butyldimethylsilyladriamycinone (148 mg), mercuric bromide (183 mg), yellow-colored mercuric oxide (494 mg) and powder of Molecular Sieves 3A (720 mg) were suspended in anhydrous 1,2-dichloroethane (5 ml), and the resulting mixture was stirred at room temperature for 20 hrs. to effect the condensation reaction.

The resulting reaction solution was diluted with chloroform, filtered with aid of Celite to afford the filtrate. The residue from the filtration was washed with chloroform. The above filtrate was combined with the washings, and the resulting mixture was washed successively with a 30% aqueous potassium iodide solution, a saturated sodium hydrogen carbonate solution and water. The solution so washed with water was dried over anhydrous sodium sulfate and concentrated under a reduced pressure. The residue thus obtained was subjected to a silica gel column chromatography (developer: toluene-acetone, 12:1) to separate and purify the desired compound. The titled Compound 79 was obtained as a red solid (107 mg, yield 52%).

$^1$H-NMR spectrum (in deutero-chloroform):
δ5.74 (1H, d, H-1')
4.10 (3H, s, OCH$_3$)
2.14, 1.98 (each 3H, s, OAc)

(2) Preparation of 7-O-(2,6-dideoxy-2,6,6,6-tetrafluoro-α-L-talopyranosyl)adriamycinone [Compound of the formula (C-b)]

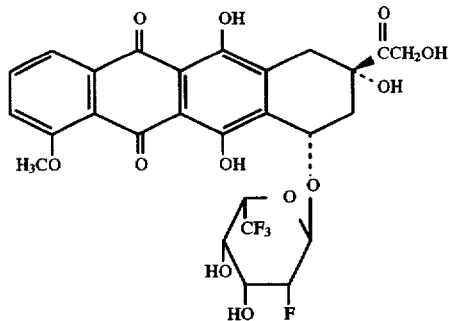

Compound 79 as obtained in the item (1) above, i.e. 7-O-(3,4-di-O-acetyl-2,6-dideoxy-2,6,6,6-tetrafluoro-α-L-talopyranosyl)-14-O-tert-butyldimethylsilyladriamycinone (98 mg) was suspended in anhydrous methanol (10 ml) and a 0.25N methanolic solution (0.3 ml) of sodium methoxide was added to the resulting suspension. The mixture obtained was stirred at room temperature for 3 hrs. to effect the elimination of the acetyl group from Compound 79. The resulting reaction solution, after addition of a small piece of dry ice thereto, was concentrated under a reduced pressure. The residue was diluted with chloroform, washed with water, dried over anhydrous sodium sulfate and concentrated under a reduced pressure. The resulting residue was dissolved in a mixture of chloroform-methanol and the solution obtained was subjected to a reprecipitation with addition of hexane, to yield the deacetylated product (67 mg) as a red solid.

The solid thus obtained was then dissolved in an 80% aqueous acetic acid solution (3 ml) and the solution was allowed to stand at 80° C. for 30 minutes (for elimination of TBS). The resulting reaction solution was concentrated under a reduced pressure and the residue was washed with water, dried under a reduced pressure, washed with toluene and then dried under a reduced pressure. The titled compound was obtained as a red solid (48 mg, yield 64%). This compound showed a specific optical rotation:

$[\alpha]_D^{24}$+114° (c 0.2, tetrahydrofuran).

REFERENTIAL EXAMPLE 4

(1) Preparation of 7-O-(3,4-di-O-acetyl-2,6-dideoxy-6,6,6-trifluoro-α-L-lyxo-hexopyranosyl)-14-O-tert-butyldimethylsilyladriamycinone (Compound 80)

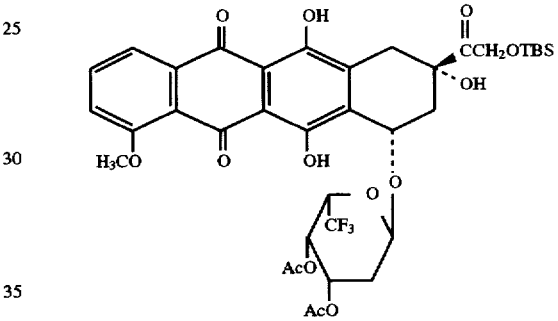

Compound 78 as obtained in Referential Example 2 (12), i.e. 3,4-di-O-acetyl-2,6-dideoxy-6,6,6-trifluoro-α-L-lyxo-hexopyranosyl bromide (85 mg), 14-O-tert-butyldimethylsilyladriamycinone [see D. Horton, W. Priebe and O. Varela, "The Journal of Antibiotics" Vol. 37, pp. 853-858 (1984)] (142 mg), mercuric bromide (174 mg), yellow-colored mercuric oxide (498 mg) and powder of Molecular Sieves 3A (696 mg) were suspended in anhydrous 1,2-dichloroethane (4 ml), and the resulting mixture was stirred at room temperature for 18 hrs. to conduct the condensation reaction.

The resulting reaction solution was diluted with chloroform, filterd with aid of Celite to give the filtrate. The residue from the filtration was washed with chloroform. The above filtrate and the washings were combined and the mixture was washed, successively, with a 30% aqueous potassium iodide solution, a saturated aqueous sodium hydrogen carbonate solution and water. The water-washed solution was dried over anhydrous sodium sulfate and concentrated under a reduced pressure. The residue so obtained was subjected twice to a silica gel column chromatography (The first developer: toluene-acetone, 10:1, and the second developer: chloroform-acetone, 30:1) to separate and purify the desired compound. The titled Compound 80 (50 mg, yield 26%) and β-anomer thereof (49 mg, yield 25%) were obtained each as a red solid.

$[\alpha]_D^{19}$+195° (c 0.1, chloroform)

$^1$H-NMR spectrum (in deutero-chloroform):
δ5.73 (1H, br d, H-1')
4.09 (3H, s, OCH$_3$)

2.16, 1.95 (each 3H, s, OAc)

$^{19}$F-NMR spectrum (in deutero-chloroform, CFCl$_3$ as internal standard):

δ−74.6 (d)

(2) Preparation of 7-O-(2,6-dideoxy-6,6,6-trifluoro-α-L-lyxo-hexopyranosyl) adriamycinone [Compound of the formula (D)]

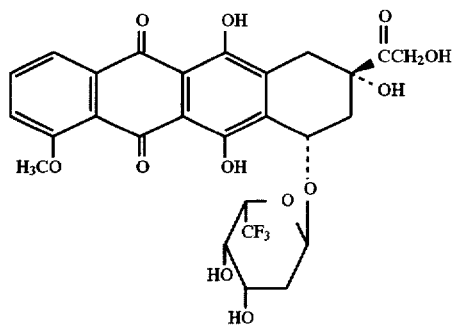

Compound 80 as obtained in the item (1) above, i.e. 7-O-(3,4-di-O-acetyl-2,6-dideoxy-6,6,6-trifluoro-α-L-lyxo-hexopyranosyl)-14-O-tert-butyldimethylsilyladriamycinone (40 mg) was suspended in anhydrous methanol (4 ml), and to the resulting suspension was added a 0.25N methanolic solution of sodium methoxide (0.13 ml). The mixture obtained was stirred at room temperature for 2.5 hrs. to effect the elimination of the acetyl group from Compound 80.

The resulting reaction solution, after a small piece of dry ice was added thereto, was concentrated under a reduced pressure. The residue obtained was diluted with chloroform, washed with water, dried over anhydrous sodium sulfate and then concentrated under a reduced pressure. The residue obtained was dissolved in a mixture of chloroform-methanol, and hexane was added to the solution to cause reprecipitation, so that the deacetylation product (27 mg) was obtained as a red solid.

This solid was then dissolved in an 80% aqueous acetic acid solution (1 ml), and the solution was allowed to stand at 80° C. for 30 minutes (for the elimination of TBS). The reaction solution obtained was concentrated under a reduced pressure, and the residue was washed with water, dried under a reduced pressure, washed with toluene and dried under a reduced pressure. Thus, there was afforded the titled compound, i.e. compound of the formula (D) (21 mg, yield 69%) as a dark red solid.

$[\alpha]_D^{21}$+188° (c 0.02, pyridine)

$^1$H-NMR spectrum (in deutero-pyridine):

δ5.95 (1H, br d, H-1')

3.98 (3H, s, OCH$_3$)

$^{19}$-NMR spectrum (in deutero-pyridine, CFCl$_3$ as internal standard):

δ−72.3 (d)

We claim:

1. A 7-O-(2,6-dideoxy-2-fluoro-3-O- or -4-O- or -3,4-di-O-aminoalkanoyl-α-L-talopyranosyl)anthracycline derivative represented by the formula

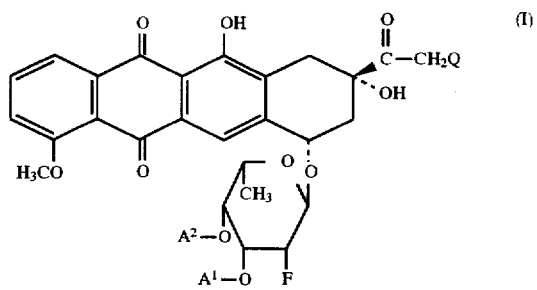

wherein Q is a hydrogen atom or a hydroxyl group, and either one or both of A$^1$ and A$^2$ is or are (i) glycyl group or a substituted glycyl group having the following formula (a):

where R is a hydrogen atom or an alkyl group of 1–8 carbon atoms, or an aryl group, or an aralkyl group, or (ii) an ω-amino acid residue having the following formula (b):

where B is a linear alkylene group of a 2–6 carbon atoms which may optionally be substituted by a (C$_1$–C$_6$) alkyl group, when A$^1$ or A$^2$ is not the glycyl group or substituted glycyl group (i) or the ω-amino acid residue (ii) it is a hydrogen atom, or a pharmaceutically acceptable acid addition salt thereof.

2. A compound as claimed in claim 1, which is a 7-O-(2,6-dideoxy-2-fluoro-3-O-aminoalkanoyl-α-L-talopyanosyl) daunomycinone derivative represented by the formula

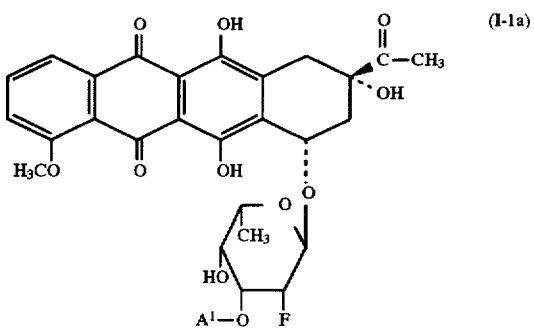

wherein A$^1$ is either (i) glycyl group or a substituted glycyl group of the formula (a) shown in claim 1, or (ii) an ω-amino acid residue of the formula (b) shown in claim 1.

3. Compound as claimed in claim 1, which is a 7-O-(2,6-dideoxy-2-fluoro-4-O-aminoalkanoyl-α-L-talopyanosyl) daunomycinone derivative represented by the formula

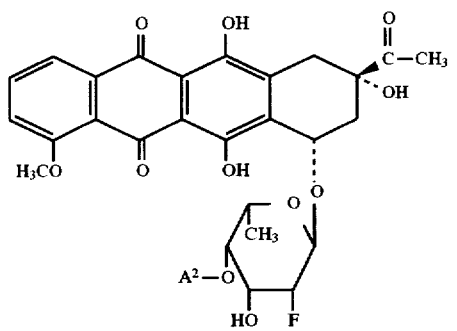

wherein $A^2$ is either (i) glycyl group or a substituted glycyl group of the formula (a) shown in claim 1, or (ii) an ω-amino acid residue of formula (b) shown in claim 1.

4. Compound as claimed in claim 1, which is a 7-O-(2,6-dideoxy-2-fluoro-3,4-di-O-aminoalkanoyl-α-L-talopyranosyl) daunomycinone derivative represented by the formula

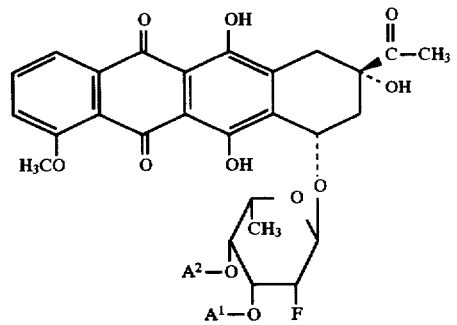

wherein both of $A^1$ and $A^2$ each are either (i) glycyl group or a substituted glycyl group of the formula (a) shown in claim 1, or (ii) an ω-amino acid residue of the formula (b) shown in claim 1.

5. Compound as claimed in claim 1, which is a 7-O-(2,6-dideoxy-2-fluoro-3-O-aminoalkanoyl-α-L-talopyranosyl) adriamycinone derivative represented by the formula

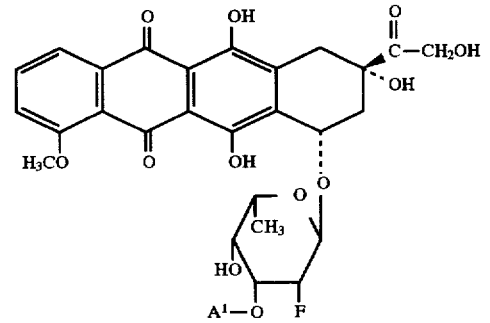

wherein $A^1$ is either (i) glycyl group or a substituted glycyl group of the formula (a) shown in claim 1, or (ii) an ω-amino acid residue of the formula (b) shown in claim 1.

6. Compound as claimed in claim 1, which is a 7-O-(2,6-dideoxy-2-fluoro-4-O-aminoalkanoyl-α-L-talopyranosyl) adriamycinone derivative represented by the formula

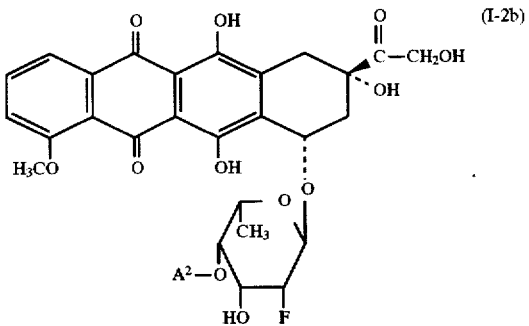

wherein $A^2$ is either (i) glycyl group or a substituted glycyl group of the formula (a) shown in claim 1, or (ii) an ω-amino acid residue of the formula (b) shown in claim 1.

7. Compound as claimed in claim 1, which is a 7-O-(2,6-dideoxy-2-fluoro-3,4-di-O-aminoalkanoyl-α-L-talopyranosyl) adriamycinone derivative represented by the formula

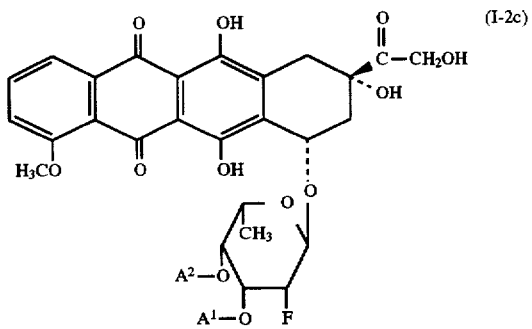

wherein both of $A^1$ and $A^2$ are either (i) glycyl group or a substituted glycyl group of the formula (a) shown in claim 1, or (ii) an ω-amino acid residue of the formula (b) shown in claim 1.

8. A 7-O-(2,6-Dideoxy-2,6,6,6-tetrafluoro-3-O- or -4-O- or -3,4-di-O-aminoalkanoyl-α-L-talopyranosyl) adriamycinone derivative or a 7-O-(2,6-dideoxy-6,6,6-trifluoro-3-O- or -4-O or -3,4-di-O-aminoalkanoyl-α-L-lyxo-hexopyranosyl) adriamycinone derivative represented by the formula

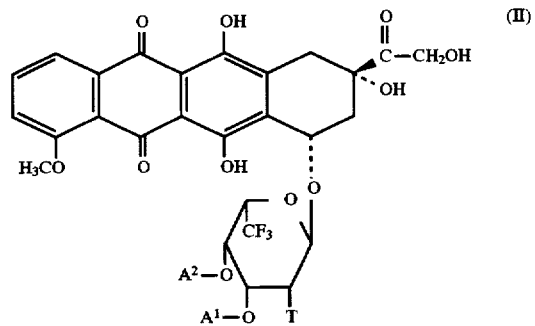

wherein T is a fluorine atom or a hydrogen atom, and either one or both of $A^1$ and $A^2$ is or are (i) glycyl group or a substituted glycyl group represented by the following formula (a):

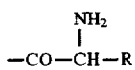

where R is a hydrogen atom or an alkyl group of 1–8 carbon atoms, or an aryl group, or an aralkyl group, or (ii) an ω-amino acid residue represented by the following formula (b):

—CO—B—NH₂ (b)

where B is a linear alkylene group of a 2–6 carbon atoms which may optionally be substituted by a ($C_1$–$C_6$) alkyl group when $A^1$ or $A^2$ is not the glycyl group or substituted glycyl group (i) or the ω-amino acid residue (ii) it is a hydrogen atom, or a pharmaceutically acceptable acid addition salt thereof.

9. Compound as claimed in claim 8, which is a 7-O-(2,6-dideoxy-2,6,6,6-tetrafluoro-3-O-aminoalkanoyl-α-L-talopyranosyl) adriamycinone derivative represented by the formula

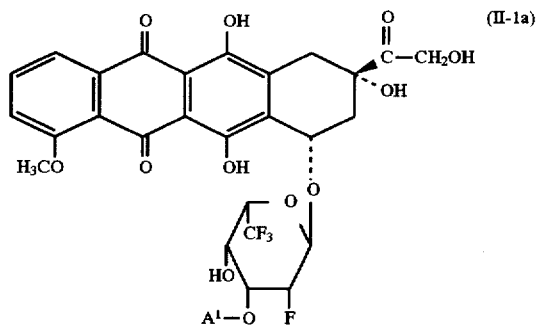

wherein $A^1$ is either (i) glycyl group or a substituted glycyl group of the formula (a) shown in claim 8, or (ii) an ω-amino acid residue of the formula (b) shown in claim 8.

10. Compound as claimed in claim 8, which is a 7-O-(2,6-dideoxy-2,6,6,6-tetrafluoro-4-O-aminoalkanoyl-α-L-talopyranosyl) adriamycinone derivative represented by the formula

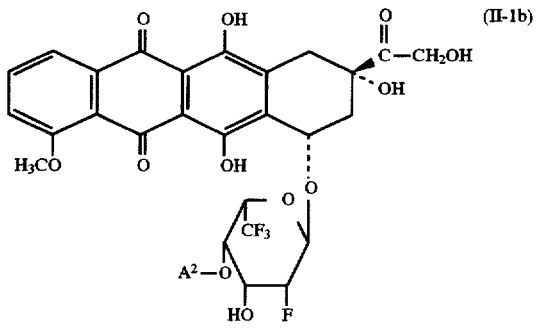

wherein $A^2$ is either (i) glycyl group or a substituted glycyl group of the formula (a) shown in claim 8, or (ii) an ω-amino acid residue of the formula (b) shown in claim 8.

11. Compound as claimed in claim 8, which is a 7-O-(2,6-dideoxy-2,6,6,6-tetrafluoro-3,4-di-O-aminoalkanoyl-α-L-talopyranosyl)adriamycinone derivative represented by the formula

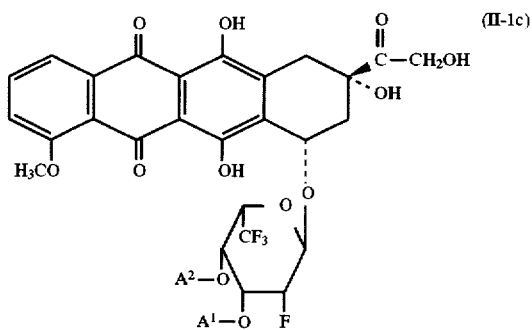

wherein both of $A^1$ and $A^2$ each are either (i) glycyl group or a substituted glycyl group of the formula (a) shown in claim 8, or (ii) an ω-amino acid residue of the formula (b) shown in claim 8.

12. Compound as claimed in claim 8, which is a 7-O-(2,6-dideoxy-6,6,6-trifluoro-3-O-aminoalkanoyl-α-L-lyxo-hexopyranosyl)adriamycinone derivative represented by the formula

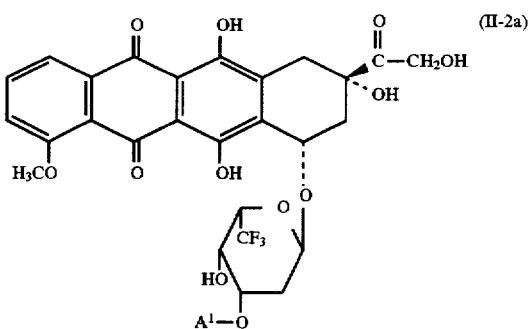

wherein $A^1$ is either (i) glycyl group or a substitued glycyl group of the formula (a) shown in claim 8, or (ii) an ω-amino acid residue of formula (b) shown in claim 8.

13. Compound as claimed in claim 8, which is a 7-O-(2,6-dideoxy-6,6,6-trifluoro-4-aminoalkanoyl-α-L-lyxo-hexopyranosyl) adriamycinone derivative represented by the formula

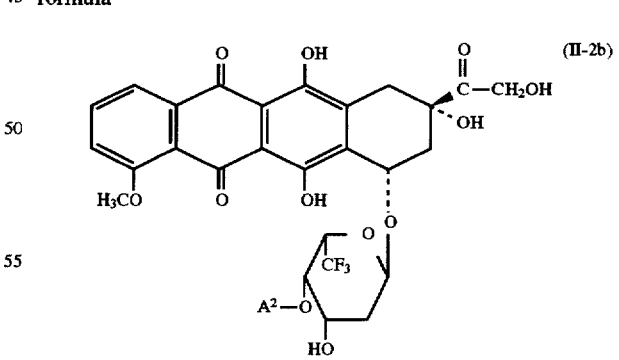

wherein $A^2$ is either (i) glycyl group or a substituted glycyl group of the formula (a) shown in claim 8, or (ii) an ω-amino acid residue of the formula (b) shown in claim 8.

14. Compound as claimed in claim 8, which is a 7-O-(2,6-dideoxy-6,6,6-trifluoro-3,4-di-O-aminoalkanoyl-α-L-lyxo-hexopyranosyl)adriamycinone derivative represented by the formula

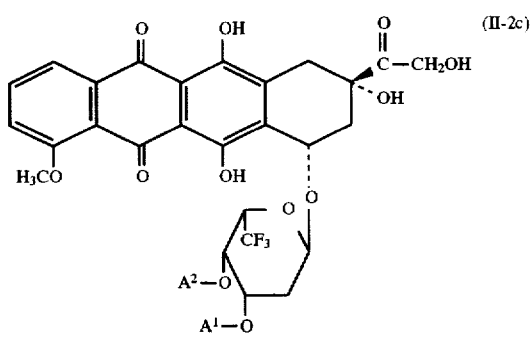
(II-2c)

wherein both of $A^1$ and $A^2$ each are either (i) glycyl group or a substituted glycyl group of the formula (a) shown in claim 8, or (ii) an ω-amino acid residue of the formula (b) shown in claim 8.

15. Compound as claimed in claim 1, wherein $A^1$ or $A^2$ in the formula (I) shown in claim 1, respectively, is glycyl group or a substituted glycyl group which is L-alanyl group, L-valyl group, L-leucyl group, L-isoleucyl group or L-phenylalanyl group.

16. Compound as claimed in claim 1, wherein $A^1$ or $A^2$ in the formula (I), shown in claim 1 is a 3-amino-propionyl group, a 4-aminobutyryl group or a 4-amino-2,2-dimethylbutyryl group, as the ω-amino acid residue of the formula —CO—B—$NH_2$ in which B has the meanings as defined above.

17. An antitumor composition characterized in that the composition contains as an active ingredient an anthracycline derivative having the formula (I) as defined in claim 1, or a pharmaceutically acceptable acid addition salt thereof in association with a pharmaceutically acceptable carrier.

18. Compound as claimed in claim 8, wherein $A^1$ or $A^2$ in the formula (II) shown in claim 8, is glycyl group or a substituted glycyl group which is L-alanyl group, L-valyl group, L-leucyl group, L-isoleucyl group or L-phenylalanyl group.

19. Compound as claim in claim 8, wherein $A^1$ or $A^2$ in the general formula (II) shown in claim 8, is 3-aminopropionyl group, 4-aminobutyryl group or 4-amino-2,2-dimethylbutyryl group, as the ω-amino acid residue of the formula —CO—B—$NH_2$ in which B has the meanings as defined above.

20. An antitumor composition characterized in that the composition contains as an active ingredient an adriamycinone derivative having the formula (II) as defined in claim 8, or a pharmaceutically acceptable acid addition salt thereof.

* * * * *